US 7,998,482 B2

(12) United States Patent
Wong et al.

(10) Patent No.: US 7,998,482 B2
(45) Date of Patent: *Aug. 16, 2011

(54) METHODS AND REAGENTS FOR THE ANALYSIS AND PURIFICATION OF POLYSACCHARIDES

(75) Inventors: Chi-Huey Wong, Rancho Santa Fe, CA (US); Shie-Liang Hsieh, Taipei (TW); Tsui-Ling Hsu, Taipei (TW); Shih-Chin Cheng, Nantou (TW); Szu-Ting Chen, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 12/533,086

(22) Filed: Jul. 31, 2009

(65) Prior Publication Data

US 2010/0055096 A1  Mar. 4, 2010

Related U.S. Application Data

(62) Division of application No. 11/469,270, filed on Aug. 31, 2006, now abandoned.

(60) Provisional application No. 60/713,463, filed on Aug. 31, 2005.

(51) Int. Cl.
*A61K 39/395* (2006.01)
*C12N 7/00* (2006.01)
*A61K 39/285* (2006.01)

(52) U.S. Cl. .............. 424/143.1; 424/133.1; 424/130.1; 435/235.1; 530/387.1; 530/388.1; 530/388.15

(58) Field of Classification Search .................. None
See application file for complete search history.

(56) References Cited

OTHER PUBLICATIONS

Chen et al., CLEC5A is critical for dengue-virus-induced lethal disease, 2008, Nature, vol. 453, pp. 672-676.*
Divangahi et al., Critical Negative Regulation of Type 1 T Cell Immunity and Immunopathology by Signaling Adaptor DAP12 during Intracellular Infection, 2007, Journal of Immunology, vol. 179, pp. 4015-4026.*
Aoki, et al., "Differential Regulation of DAP12 and Molecules Associated with DAP12 during Host Responses to Mycobacterial Infection", *Infection and Immunity*, May 2004, p. 2477-2483, vol. 72, No. 5.
Bakker, et al., "Myeloid DAP12-associating lectin (MDL)-1 is a cell surface receptor involved in the activation of myeloid cells", *Proc. Natl. Acad. Sci. USA* vol. 96, pp. 9792-9796, Aug. 1999.
Bouchon, et al., "Cutting Edge: Inflammatory Responses Can be Triggered by TREM-1, a Novel Receptor Expressed on Neutrophils and Monocytes", *The Journal of Immunology*, 2000, 164: 4991-4995.
Galustian, et al., "High and Low Affinity Carbohydrate Ligands Revealed for Murine SIGN-R1 by Carbohydrate Array and Cell Binding Approaches, and Differing Specificities for SIGN-R3 and Langerin", *International Immunology*, vol. 16, No. 6, pp. 853-866, Jun. 2, 2004.
Law, et al., "Ig Domains 1 and 2 of Murine CD22 Constitute the Ligand-Binding Domain and Bind Multiple Sialylated Ligands Expressed on B and T Cells", *The Journal of Immunology*, vol. 155, Issue 7, 3368-3376, 1995.
LeBouder, et al., "Soluble Forms of Toll-Like Receptor (TLR)2 Capable of Modulating TLR2 Signaling are Present in Human Plasma and Breast Milk", *The Journal of Immunology*, 2003, 171:6680-6689.
Linehan, et al., "Endogenous Ligands of Carbohydrate Recognition Domains of the Mannose Receptor in Murine Macrophages, Endothelial Cells and Secretory Cells; Potential Relevance to Inflammation and Immunity", *Eur. J. Immunol.* 2001:31:1857-1866.

* cited by examiner

*Primary Examiner* — Mary E Mosher
*Assistant Examiner* — Benjamin P Blumel
(74) *Attorney, Agent, or Firm* — Occhiuti Rohlicek & Tsao LLP

(57) ABSTRACT

The disclosure provides fusion proteins comprising a carbohydrate recognition domain of an innate immunity receptor and a heterologous polypeptide. The fusion proteins of the disclosure may be used, for example, to fingerprint polysaccharide compositions and to purify polysaccharide compositions. Polysaccharide compositions include those isolated from *Ganoderma lucidum* (Reishi). The methods and reagents of the disclosure may also be used to identify innate immunity receptors and cell types that bind to polysaccharide compositions (including polysaccharide compositions associated with pathogens), whereupon modulators of the identified receptors can then be obtained. The fusion proteins also may be used to inhibit the interaction between a polysaccharide composition and an innate immunity receptor on a cell surface. The methods and reagents of the disclosure are used in one example to determine that the DLVR1 innate immunity receptor on macrophages interacts with Dengue virus (DV), and that DLVR1 is responsible for DV-mediated secretion of proinflammatory cytokines from macrophages. The disclosure also provides DVLR1 antibodies that prevent the secretion of proinflammatory cytokines by DV-infected macrophages.

4 Claims, 29 Drawing Sheets

| No | Probe | Binding with GLPS F3 | Binding with GLPS F3C |
|---|---|---|---|
| 1 | CLEC1A/CLEC-1 | - | - |
| 2 | CLEC2B/AICL | - | - |
| 3 | CLEC4A/DCIR | - | - |
| 4 | CLEC4C/BDCA-2 | - | - |
| 5 | CLEC4D/CLEC-6 | - | - |
| 6 | CLEC4E/MINCLE | - | - |
| 7 | CLEC4F/KCLR | +++ | +++ |
| 8 | CLEC4H2/HBVxAgBP | - | - |
| 9 | CLEC4K/Langerin | - | - |
| 10 | CLEC4L/DC-SIGN | - | - |
| 11 | CLEC4M/DC-SIGNR | ++++ | ++++ |
| 12 | CLEC5A/MDL1 | - | - |
| 13 | CLEC6A/Dectin-2 | - | - |
| 14 | CLEC7A/Dectin-1 | +++++ | ++++ |
| 15 | CLEC12A/CLL-1 | - | - |
| 16 | CLEC13A/BIMLEC | - | - |
| 17 | MAFAL | - | - |
| 18 | NKG2D | - | - |
| 19 | Siglec11 | - | - |
| 20 | TLT-1 | - | - |
| 21 | TLT-2 | ++++ | - |
| 22 | TREM-1 | - | - |
| 23 | TREM-2 | - | - |
| 24 | mTLT1 | - | - |
| 25 | mTLT4 | - | - |
| 26 | mTREM1 | - | - |
| 27 | mTREM2 | - | - |
| 28 | hIgG1 | - | - |

FIGURE 3

| No | Polysaccharides sample | Dectin-1.Fc | DC-SIGNR.Fc | mKCR.Fc | TLT-2.Fc | hIgG1 |
|---|---|---|---|---|---|---|
| 1 | F3 | +++++ | +++++ | +++++ | +++++ | - |
| 2 | Reishi 1 | +++ | + | - | - | - |
| 3 | Reishi 2 | +++ | ++ | + | - | - |
| 4 | Reishi 3 | + | + | + | ++ | - |
| 5 | Crude extract | ++ | + | - | - | - |
| 6 | *Dendrobiun huoshanense* polysaccharide | - | - | - | - | - |
| 7 | *Cordyceps sinensis* polysaccharide | +++ | + | + | - | - |
| 8 | Mushroom polysaccharides L | + | +++ | - | - | - |
| 9 | Mushroom polysaccharides M | ++ | + | - | - | - |
| 10 | dH$_2$O | - | - | - | - | - |

SEQUENCE LISTING

```
<160> NUMBER OF SEQ ID NOS: 39

<210> SEQ ID NO 1
<211> LENGTH: 27
<212> TYPE: DNA
<213> ORGANISM: Artificial sequence
<220> FEATURE:
<223> OTHER INFORMATION: Synthetic DNA primer sequence

<400> SEQUENCE: 1
gaatcctttc agtactacca gctctcc                                  27

<210> SEQ ID NO 2
<211> LENGTH: 27
<212> TYPE: DNA
<213> ORGANISM: Artificial sequence
<220> FEATURE:
<223> OTHER INFORMATION: Synthetic DNA primer sequence

<400> SEQUENCE: 2
gaattctcag tcaccttcgc ctaatgt                                  27

<210> SEQ ID NO 3
<211> LENGTH: 24
<212> TYPE: DNA
<213> ORGANISM: Artificial sequence
<220> FEATURE:
<223> OTHER INFORMATION: Synthetic DNA primer sequence

<400> SEQUENCE: 3
ggatccctgg ggatttggtc tgtc                                     24

<210> SEQ ID NO 4
<211> LENGTH: 24
<212> TYPE: DNA
<213> ORGANISM: Artificial sequence
<220> FEATURE:
<223> OTHER INFORMATION: Synthetic DNA primer sequence

<400> SEQUENCE: 4
gaattcttaa ggtagttggt ccac                                     24

<210> SEQ ID NO 5
<211> LENGTH: 24
<212> TYPE: DNA
<213> ORGANISM: Artificial sequence
<220> FEATURE:
<223> OTHER INFORMATION: Synthetic DNA primer sequence

<400> SEQUENCE: 5
```

```
ggatcctctc agagtttatg cccc                                          24
```

<210> SEQ ID NO 6
<211> LENGTH: 24
<212> TYPE: DNA
<213> ORGANISM: Artificial sequence
<220> FEATURE:
<223> OTHER INFORMATION: Synthetic DNA primer sequence

<400> SEQUENCE: 6

```
ggatccccc attatcttag acat                                           24
```

<210> SEQ ID NO 7
<211> LENGTH: 30
<212> TYPE: DNA
<213> ORGANISM: Artificial sequence
<220> FEATURE:
<223> OTHER INFORMATION: Synthetic DNA primer sequence

<400> SEQUENCE: 7

```
ggatcctttc aaaaatattc tcagcttctt                                    30
```

<210> SEQ ID NO 8
<211> LENGTH: 28
<212> TYPE: DNA
<213> ORGANISM: Artificial sequence
<220> FEATURE:
<223> OTHER INFORMATION: Synthetic DNA primer sequence

<400> SEQUENCE: 8

```
gaattctcat aagtggatct tcatcatc                                      28
```

<210> SEQ ID NO 9
<211> LENGTH: 30
<212> TYPE: DNA
<213> ORGANISM: Artificial sequence
<220> FEATURE:
<223> OTHER INFORMATION: Synthetic DNA primer sequence

<400> SEQUENCE: 9

```
ggatccttta tgtatagcaa aactgtcaag                                    30
```

<210> SEQ ID NO 10
<211> LENGTH: 30
<212> TYPE: DNA
<213> ORGANISM: Artificial sequence
<220> FEATURE:
<223> OTHER INFORMATION: Synthetic DNA primer sequence

<400> SEQUENCE: 10

```
gaattcttat atgtagatct tcttcatctt                                    30
```

<210> SEQ ID NO 11
<211> LENGTH: 27
<212> TYPE: DNA
<213> ORGANISM: Artificial sequence
<220> FEATURE:
<223> OTHER INFORMATION: Synthetic DNA primer sequence

<400> SEQUENCE: 11

```
gaatcccatc acaactttc acgctgt                                        27
```

<210> SEQ ID NO 12
<211> LENGTH: 27
<212> TYPE: DNA
<213> ORGANISM: Artificial sequence
<220> FEATURE:

-continued

<223> OTHER INFORMATION: Synthetic DNA primer sequence

<400> SEQUENCE: 12
gaattcctag ttcaatgttg ttccagg                                27

<210> SEQ ID NO 13
<211> LENGTH: 29
<212> TYPE: DNA
<213> ORGANISM: Artificial sequence
<220> FEATURE:
<223> OTHER INFORMATION: Synthetic DNA primer sequence

<400> SEQUENCE: 13
gaagatctac atttcgcatc tttcaaacc                              29

<210> SEQ ID NO 14
<211> LENGTH: 27
<212> TYPE: DNA
<213> ORGANISM: Artificial sequence
<220> FEATURE:
<223> OTHER INFORMATION: Synthetic DNA primer sequence

<400> SEQUENCE: 14
gcggttaaag agattttcct ttgttca                                27

<210> SEQ ID NO 15
<211> LENGTH: 24
<212> TYPE: DNA
<213> ORGANISM: Artificial sequence
<220> FEATURE:
<223> OTHER INFORMATION: Synthetic DNA primer sequence

<400> SEQUENCE: 15
ggatcccggt ttatgggcac cata                                   24

<210> SEQ ID NO 16
<211> LENGTH: 24
<212> TYPE: DNA
<213> ORGANISM: Artificial sequence
<220> FEATURE:
<223> OTHER INFORMATION: Synthetic DNA primer sequence

<400> SEQUENCE: 16
ggatcctcac ggttctgatg ggac                                   24

<210> SEQ ID NO 17
<211> LENGTH: 26
<212> TYPE: DNA
<213> ORGANISM: Artificial sequence
<220> FEATURE:
<223> OTHER INFORMATION: Synthetic DNA primer sequence

<400> SEQUENCE: 17
ggatccaagg tccccagctc cataag                                 26

<210> SEQ ID NO 18
<211> LENGTH: 23
<212> TYPE: DNA
<213> ORGANISM: Artificial sequence
<220> FEATURE:
<223> OTHER INFORMATION: Synthetic DNA primer sequence

<400> SEQUENCE: 18
gaattcctac gcaggagggg ggt                                    23

<210> SEQ ID NO 19

<211> LENGTH: 24
<212> TYPE: DNA
<213> ORGANISM: Artificial sequence
<220> FEATURE:
<223> OTHER INFORMATION: Synthetic DNA primer sequence

<400> SEQUENCE: 19
ggatcctcca aggtccccag ctcc                                              24

<210> SEQ ID NO 20
<211> LENGTH: 26
<212> TYPE: DNA
<213> ORGANISM: Artificial sequence
<220> FEATURE:
<223> OTHER INFORMATION: Synthetic DNA primer sequence

<400> SEQUENCE: 20
gaattcctat tcgtctctga agcagg                                            26

<210> SEQ ID NO 21
<211> LENGTH: 26
<212> TYPE: DNA
<213> ORGANISM: Artificial sequence
<220> FEATURE:
<223> OTHER INFORMATION: Synthetic DNA primer sequence

<400> SEQUENCE: 21
agatctagta acgatggttt caccac                                            26

<210> SEQ ID NO 22
<211> LENGTH: 27
<212> TYPE: DNA
<213> ORGANISM: Artificial sequence
<220> FEATURE:
<223> OTHER INFORMATION: Synthetic DNA primer sequence

<400> SEQUENCE: 22
gaattcctgt gatcatttgg cattctt                                           27

<210> SEQ ID NO 23
<211> LENGTH: 24
<212> TYPE: DNA
<213> ORGANISM: Artificial sequence
<220> FEATURE:
<223> OTHER INFORMATION: Synthetic DNA primer sequence

<400> SEQUENCE: 23
ggatccacat atggtgaaac tggc                                              24

<210> SEQ ID NO 24
<211> LENGTH: 21
<212> TYPE: DNA
<213> ORGANISM: Artificial sequence
<220> FEATURE:
<223> OTHER INFORMATION: Synthetic DNA primer sequence

<400> SEQUENCE: 24
gaattccatc agtcgatggg c                                                 21

<210> SEQ ID NO 25
<211> LENGTH: 27
<212> TYPE: DNA
<213> ORGANISM: Artificial sequence
<220> FEATURE:
<223> OTHER INFORMATION: Synthetic DNA primer sequence

<400> SEQUENCE: 25
ggatccacca tggctatttg gagatcc                                    27

<210> SEQ ID NO 26
<211> LENGTH: 30
<212> TYPE: DNA
<213> ORGANISM: Artificial sequence
<220> FEATURE:
<223> OTHER INFORMATION: Synthetic DNA primer sequence

<400> SEQUENCE: 26
gaattcttac attgaaaact tcttctcaca                                 30

<210> SEQ ID NO 27
<211> LENGTH: 27
<212> TYPE: DNA
<213> ORGANISM: Artificial sequence
<220> FEATURE:
<223> OTHER INFORMATION: Synthetic DNA primer sequence

<400> SEQUENCE: 27
ggatcctcca aatttcagag ggacctg                                    27

<210> SEQ ID NO 28
<211> LENGTH: 25
<212> TYPE: DNA
<213> ORGANISM: Artificial sequence
<220> FEATURE:
<223> OTHER INFORMATION: Synthetic DNA primer sequence

<400> SEQUENCE: 28
gaattctcag tgactctcct ggctg                                      25

<210> SEQ ID NO 29
<211> LENGTH: 30
<212> TYPE: DNA
<213> ORGANISM: Artificial sequence
<220> FEATURE:
<223> OTHER INFORMATION: Synthetic DNA primer sequence

<400> SEQUENCE: 29
ggatccgtaa ctttgaagat agaaatgaaa                                 30

<210> SEQ ID NO 30
<211> LENGTH: 28
<212> TYPE: DNA
<213> ORGANISM: Artificial sequence
<220> FEATURE:
<223> OTHER INFORMATION: Synthetic DNA primer sequence

<400> SEQUENCE: 30
gaatcctcat gcctccctaa aatatgta                                   28

<210> SEQ ID NO 31
<211> LENGTH: 23
<212> TYPE: DNA
<213> ORGANISM: Artificial sequence
<220> FEATURE:
<223> OTHER INFORMATION: Synthetic DNA primer sequence

<400> SEQUENCE: 31
ggatcctcat gctccgggcc gcg                                        23

<210> SEQ ID NO 32
<211> LENGTH: 27
<212> TYPE: DNA
<213> ORGANISM: Artificial sequence
<220> FEATURE:

```
<223> OTHER INFORMATION: Synthetic DNA primer sequence

<400> SEQUENCE: 32
gaattcgcta gcaatcacca atgctga                                        27

<210> SEQ ID NO 33
<211> LENGTH: 20
<212> TYPE: DNA
<213> ORGANISM: Artificial sequence
<220> FEATURE:
<223> OTHER INFORMATION: Synthetic DNA primer sequence

<400> SEQUENCE: 33
agaggtgaca gaggatccca                                                20

<210> SEQ ID NO 34
<211> LENGTH: 24
<212> TYPE: DNA
<213> ORGANISM: Artificial sequence
<220> FEATURE:
<223> OTHER INFORMATION: Synthetic DNA primer sequence

<400> SEQUENCE: 34
gaattcgtga tcccatcaca gtcc                                           24

<210> SEQ ID NO 35
<211> LENGTH: 22
<212> TYPE: DNA
<213> ORGANISM: Artificial sequence
<220> FEATURE:
<223> OTHER INFORMATION: Synthetic DNA primer sequence

<400> SEQUENCE: 35
ggatcctgcc agggctccaa ct                                             22

<210> SEQ ID NO 36
<211> LENGTH: 19
<212> TYPE: DNA
<213> ORGANISM: Artificial sequence
<220> FEATURE:
<223> OTHER INFORMATION: Synthetic DNA primer sequence

<400> SEQUENCE: 36
atgacagatc tgagggtca                                                 19

<210> SEQ ID NO 37
<211> LENGTH: 19
<212> TYPE: DNA
<213> ORGANISM: Artificial sequence
<220> FEATURE:
<223> OTHER INFORMATION: Synthetic DNA primer sequence

<400> SEQUENCE: 37
cagccttgga gacctgagt                                                 19

<210> SEQ ID NO 38
<211> LENGTH: 17
<212> TYPE: DNA
<213> ORGANISM: Artificial sequence
<220> FEATURE:
<223> OTHER INFORMATION: Synthetic DNA primer sequence

<400> SEQUENCE: 38
tagcctactc tggccgc                                                   17

<210> SEQ ID NO 39
```

```
<211> LENGTH: 18
<212> TYPE: DNA
<213> ORGANISM: Artificial sequence
<220> FEATURE:
<223> OTHER INFORMATION: Synthetic DNA primer sequence

<400> SEQUENCE: 39
ttgttggaat gaccttat                                                    18
```

METHODS AND REAGENTS FOR THE ANALYSIS AND PURIFICATION OF POLYSACCHARIDES

This application is a divisional application of U.S. patent application Ser. No. 11/469,270, filed Aug. 31, 2006, which claims the benefit of U.S. Provisional Patent Application Ser. No. 60/713,463, filed Aug. 31, 2005. The contents of both prior applications are incorporated herein by reference in their entirety.

This work was supported by grant 94F008-5, NSC 95-2320-B-010-010 and NSC 95-3112-B-010-017 from the National Sciences Council, Taiwan. This work was also supported by grant 94M002-1 from the Academia Sinica, Taiwan, and by grant 95A-CT8G02 from the National Yang-Ming University.

BACKGROUND

Citation to any reference in this specification is not, and should not be taken as, an acknowledgment or any form of suggestion that this reference forms part of the common general knowledge or of the prior art in any country. All references cited herein are specifically incorporated herein by reference in their entirety.

The immune system enables a host organism to discriminate self from non-self antigens, as well as to recognize and eradicate invasive pathogens. The adaptive immunity system relies on highly polymorphic molecules, such as class I and class II antigens of the major histocompatibility complex (MHC), T cell receptors, and B cell receptors, to present antigens to T cells and B cells, thus leading to the activation of immune system. The mechanism by which the innate immunity system can recognize these diverse antigens remained unsolved until the emergence of the concept of 'pattern recognition receptors (PPRs)' proposed by Janeway (Janeway, 1989, Cold Spring Harb Symp Quant Biol 54 Pt 1, 1-13). This hypothesis was later proved correct by the identification of pathogen-associated molecular patterns (PAMPs) which are recognized by TOLL-like receptors (Aderem and Ulevitch, 2000 Nature 406, 782-7; Akira and Takeda, 2004, Nat Rev Immunol 4, 499-511; Athman and Philpott, 2004, Curr Opin Microbiol 7, 25-32), lectin receptors (Cambi and Figdor, 2003, Curr Opin Cell Biol 15, 539-46), immunoglobulin-like (Ig-like) receptors (Daws et al., 2003, J immunol 171, 594-9), and NOD proteins (Athman and Philpott, 2004, Curr Opin Microbiol 7, 25-32), and others (Liu et al., 2001, J Biol Chem 276, 34686-94; McDonald et al., 2005, J Biol Chem 280, 20177-80).

In addition to the well characterized PAMPs recognized by TOLL-like receptors (Akira and Takeda, 2004, Nat Rev Immunol 4, 499-511), recent study indicates that the host immune system can recognize invasive pathogens through specific carbohydrate antigens. For example, mannose receptors can recognize the high mannose sugar moiety expressed on the surface of pathogens (Stahl and Ezekowitz, 1998, Curr Opin Immunol 10, 50-5), while the Dectin-1 receptor can bind specifically to β-glucan, the major backbone of polysaccharides on fungus walls (Brown and Gordon, 2001, Nature 413, 36-7; Herre et al., 2004, Mol Immunol 40, 869-76). This suggests that the carbohydrate structures associated with pathogens are one of the targets recognized by the innate immunity receptors of immune cells.

*Ganoderma* species and *Cordyceps* species are groups of medical fungus which are the most popular herbal drugs taken in China. Polysaccharides extracted from *Ganoderma lucidum* (also known as Ling zhi, Reishi) have been used in traditional Chinese medicine (TCM) as anti-tumor agents and as immuno-modulating agents (Lien, 1990, Prog Drug Res 34, 395-420; Wang et al., 2002, Bioorg Med Chem 10, 1057-62; Shiao, 2003, Chem Rec 3, 172-80), while those extracted from *Cordyceps sinensis* (*Cordyceps*, Caterpillar fungus) have been shown to alter apoptotic homeostasis, and to improve respiratory, renal and cardiovascular functions (Buenz et al., 2005, J Ethnopharmacol 96, 19-29; Zhu et al., 1998, J Altern Complement Med 4, 289-303; Zhu et al., 1998, J Altern Complement Med 4, 429-57), as well as to increase whole body sensitivity to insulin (Balon et al., 2002, J Altern Complement Med 8, 315-23). However, the polysaccharide composition of the extracts vary when they the polysaccharides are extracted from different sources, from different strains, and under different growing conditions.

Analytical methods relying on high-performance liquid chromatography (HPLC) and proton-nuclear magnetic resonance have been applied to investigate the components of polysaccharides isolated from *Ganoderma lucidum* and *Cordyceps sinensis* (He and Seleen, 2004, Int. J. Med. Mushrooms 6, 253). However, the HPLC chromatogram is based on the comparison with ganoderic acid A and C (two major triterpenes of *Ganoderma lucidum*) or adenosine. It is still difficult to know whether the extracts contain the active components of polysaccharides based on the mass spectrum.

SUMMARY

In one series of embodiments, the disclosure provides a fusion protein comprising a carbohydrate recognition domain of an innate immunity receptor; and a heterologous polypeptide. In one embodiment, the heterologous polypeptide comprises an immunoglobulin, such as human IgG, or a fragment of an immunoglobulin, such as human IgG Fc, or a variant of human IgG Fc that does not bind to Fc receptors. The fusion protein may further comprise a linker peptide between the carbohydrate recognition domain and the heterologous polypeptide.

In some embodiments, the innate immunity receptor from which the carbohydrate recognition domain is derived may be a C-type lectin, such as a C-type lectin selected from the group consisting of ASGR1, ASGR2, CD207 (CLEC4K), CD209, CD302, CLEC1A, CLEC1B, CLEC2A, CLEC2B, CD69, CLEC2D, CLEC2L, CLEC3A, CLEC3B, CLEC3O, CLEC3Q, CLEC4A, CLEC4C, CLEC4D, CLEC4E, CLEC4F, CLEC4G, CLEC4M, CD209, CLEC5A, CLEC6A, CLEC7A, CLEC9A, CLEC10A, CLEC11A, CLEC12A, CLEC14A, FCER2, KLRB1, KLRF1, LY75, MRC1, MRC1L1, MRC2, OLR1, PLA2R1, mKCR, and COLEC10.

In some embodiments, the innate immunity receptor from which the carbohydrate recognition domain is derived may be an immunoglobulin-like receptor.

In some embodiments the innate immunity receptor from which the carbohydrate recognition domain is derived is selected from the group consisting of CD300 Antigen Like Family Member B (CD300LB), CD300 Antigen Like Family Member G (CD300LG), TREM1, TREM2, TREML1, TREML2, TREML3, and TREML4.

In some embodiments the innate immunity receptor from which the carbohydrate recognition domain is derived is selected from the group consisting of TLR1, TLR2, TLR3, TLR4, TLR5, TLR6, TLR7, TLR8, TLR9, TLR10, TLR11, TLR12, TLR13, TICAM1, and TICAM2.

In some embodiments the innate immunity receptor from which the carbohydrate recognition domain is derived is selected from the group consisting of CD22, CD33, Myelin Associated Glycoprotein (MAG), SIGLEC5, SIGLEC6, SIGLEC7, SIGLEC8, SIGLEC9, SIGLEC10, SIGLEC11, SIGLEC12, SIGLEC13, and Sialoadhesin (SN).

In another aspect, the disclosure provides a method for determining whether a specific carbohydrate component is present in a composition comprising a polysaccharide. The method comprises contacting the polysaccharide with a fusion protein comprising:
 (i) a carbohydrate recognition domain of an innate immunity receptor, wherein the carbohydrate recognition domain is capable of binding to the specific carbohydrate component; and
 (ii) a heterologous polypeptide; and
and then determining whether the fusion protein has bound to the polysaccharide.

In some embodiments, the aforementioned method may be performed wherein the composition comprising the polysaccharide is immobilized on a solid support. The determination of binding between the fusion protein and the polysaccharide is accomplished by determining whether the heterologous polypeptide is present on said solid support, wherein the presence of the heterologous polypeptide is indicative of the presence of the specific carbohydrate in the composition.

The heterologous polypeptide may be, for example, an immunoglobulin or a fragment of an immunoglobulin. In some embodiments, the heterologous polypeptide is conjugated to at least one biotin, which allows detection of the heterologous polypeptide using, for example, a streptavidin-conjugated enzyme. In other embodiments, the heterologous polypeptide is detected using an antibody that binds to the polypeptide. In further embodiments, the heterologous polypeptide is labelled with a detectable moiety, such as an enzyme or a fluorophore.

In another aspect, the disclosure provides a kit comprising one of the aforementioned fusion proteins and further comprising reagents for detecting the presence of said heterologous polypeptide on said solid support.

In another aspect, the disclosure provides a method for isolating a composition comprising a polysaccharide from a mixture, wherein the polysaccharide comprises a specific carbohydrate component, the method comprising providing a solid support comprising an immobilized fusion protein (comprising a carbohydrate recognition domain of an innate immunity receptor, wherein the carbohydrate recognition domain is capable of binding to the specific carbohydrate component; and a heterologous polypeptide); contacting the solid support with the mixture wherein the specific carbohydrate component binds to said carbohydrate recognition domain; washing the solid support; and dissociating the specific carbohydrate component from the fusion protein, whereby the composition comprising the polysaccharide may be isolated. In some embodiments, the composition comprising a polysaccharide is a peptidoglycan. In other embodiments, the composition comprising a polysaccharide is a fungal cell. In still further embodiments, the composition comprising a polysaccharide is a glycoprotein.

In another aspect, the disclosure provides a method for determining whether an innate immunity receptor binds to a pathogen, the method comprising: contacting the pathogen with a fusion protein comprising:
 (i) a carbohydrate recognition domain of the innate immunity receptor, wherein the carbohydrate recognition domain is capable of binding to a specific carbohydrate component; and
 (ii) a heterologous polypeptide;
and determining whether the fusion protein has bound to the pathogen.

In some embodiments, the pathogen is immobilized on a solid support, such as a microtiter plate, and the presence of the heterologous polypeptide on the solid support is indicative of the binding of the fusion protein to the pathogen. The pathogen may be immobilized on the solid support using an antibody specific for the pathogen.

In another embodiment, the fusion protein is immobilized on a solid support, and determining whether the fusion protein has bound to the pathogen is accomplished by using an antibody specific for the pathogen.

The pathogen can be, without limitation, a virus, a fungal cell, or a bacterial cell. The virus can be, without limitation, an enveloped virus such as a flu virus. The virus may be a virus from the Flaviviridae family, more specifically a member of the *Flavivirus* genus, such as, but not limited to, Dengue virus.

In another aspect, the disclosure provides a method of inhibiting the interaction between an innate immunity receptor on the surface of a cell and a polysaccharide that binds to a carbohydrate recognition domain of the innate immunity receptor. The method comprises contacting the cell with a fusion protein comprising:
 (a) the carbohydrate recognition domain of the innate immunity receptor; and
 (b) a heterologous polypeptide.

In some embodiments of this method, the heterologous polypeptide is a variant of human IgG Fc that does not bind to Fc receptors. The method may be performed by administering the fusion protein to an organism as a pharmaceutical composition. The pharmaceutical may comprise, in addition to the fusion protein, one or more pharmaceutically acceptable excipients. Accordingly, the disclosure also provides pharmaceutical compositions comprising any of the aforementioned fusion proteins and one or more pharmaceutically acceptable excipients.

In another aspect, the disclosure provides a method of inhibiting the interaction between an innate immunity receptor on the surface of a cell and a pathogen-associated polysaccharide that binds to a carbohydrate recognition domain of the innate immunity receptor. The method involves contacting the cell with an antibody antagonist of the innate immunity receptor. The antibody may be a monoclonal antibody, or fragment thereof. The antibody may also be a humanized antibody. The pathogen may be, without limitation, a virus (including enveloped viruses), a bacterial cell, or a fungal cell.

In another aspect, the disclosure provides a method of treating an organism (such as a human) infected with an enveloped virus, the method comprising administering to the organism an agent that inhibits the activity of Dengue Virus Lectin Receptor 1 (DVLR1). The virus in this method may be, for example, influenza virus. In some embodiments, the virus is a member of the Flaviridae family, such as a *Flavivirus* genus member (including, but not limited to, West Nile Virus, Japanese encephamyelitis virus, yellow fever virus, tick-borne encephamyelitis virus, and Dengue virus) or a *Hepacivirus* genus member (including, but not limited to, Hepatitis C).

In some embodiments, the agent that inhibits the activity of DVLR1 is an antibody against DVLR1. The antibody may be a monoclonal antibody, including a humanized monoclonal antibody. The antibody may be a fragment of an antibody against DVLR1.

In further embodiments, the agent that inhibits the activity of DVLR1 is a mediator of RNA inteference, such as an siRNA comprising sequence from DVLR1. The siRNA may be administered to the organism, or a construct may be administered to the organism that is transcribed in vivo to yield an siRNA (for example, a shRNA).

In another aspect, the disclosure provides an isolated antibody that binds to DVLR1 on CD14+ macrophages and which inhibits Dengue virus-mediated TNF-α secretion from CD14+ macrophages.

In a further aspect, the disclosure provides a purified monoclonal antibody, or epitope-binding fragment thereof, which binds to a DVLR1 epitope bound by a monoclonal antibody selected from the group consisting of 3E12A2, 3E12C1, 3E12G9, 9B12, and 8H8F5, wherein the antibody or fragment thereof inhibits TNF-α secretion by macrophages after infection with Dengue virus.

In a further aspect, the disclosure provides a monoclonal antibody, or epitope-binding fragment thereof, the monoclonal antibody being selected from the group consisting of monoclonal antibodies 3E12A2, 3E12C1, 9B12, 3E1209, and 8H8F5.

The disclosure also provides pharmaceutical compositions comprising any of the aforementioned DVLR1 monoclonal antibodies and a pharmaceutically acceptable excipient.

BRIEF DESCRIPTION OF THE DRAWINGS

FIG. 3 shows a semi-quantitative analysis of dot blots of membrane-immobilized GLPS F3 and GLPS F3C contacted with 27 different fusion proteins, each comprising the extracellular domain of the listed innate immunity receptor coupled to IgG1 Fc.

DETAILED DESCRIPTION

Figure 1A:
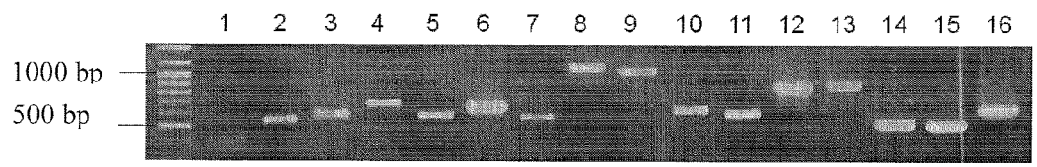
FIG. 1A shows DNA fragments of innate immunity receptors amplified by RT-PCR, then fractionated on 0.8% agarose and visualized by ethidium bromide staining.

In one implementation, the disclosure provides fusion proteins comprising a carbohydrate recognition domain of an innate immunity receptor and a heterologous polypeptide. By innate immunity receptor is meant:

1) receptors encoded by genes within the leukocyte receptor complex (LRC) and LRC-related genes on human chromosome 19, including, but not limited to, the CD66 family (CEACAM1 and PSG1), the SIGLEC family, NGK7, FCGRT, the ILT/LILRA/LILRB (CD85) family, the LAIR family, the KIR (CD158) family (including the KIR2DL subfamily, KIR2DS subfamily, and KIR3DL subfamily), FCAR (CD89), NKp46 (NCR1), and GPVI (GP6); and 2) receptors encoded by genes within the natural killer receptor complex (NKC) on human chromosome 12, including but not limited to MAFA-L (KLRG1), A2M, NKR-P1A (KLRB1), LLt1 (CLEC2D), CD69 (CLEC2C), KLRF1, AICL (CLEC2B), CLEC-2 (CLECFS2), Lox-1 (OLR1), CD94 (KLRD1), NKG2-D (KLRK1), NKG2-F (KLRC4), NKG2-E (KLRC3), NKG2-C (KLRC2), NKG2-A (KLRC1), Ly49L (KLRA1) and PRB3; and 3) all human C-type lectin (CLEC) family genes, all human Sialic Acid Binding Ig-Like (SIGLEC) genes, all human Triggering Receptor Expressed on Myeloid Cells (TREM) genes, all human TREM-like (TREML/TLT) genes, all human Toll-Like Receptor (TLR) genes, and all human Fc Receptor-like (including FCRL1 through FCLR6, and also FCLRM1 and FCLRM2) genes found on human chromosomes.

Additional genes within these groupings that may be used in the methods of the disclosure may be found using the Human Genome Organization (HUGO) search engine website. See also the locus descriptions in Immunological Reviews 2001 Vol. 181: 20-38, incorporated herein by reference in its entirety.

Orthologues of any of the aforementioned genes from non-human species may be also be used in the methods of the disclosure.

C-type lectin genes that are contemplated for use in the present disclosure include, but are not limited to the following human genes: ASGR1, ASGR2 (CLEC4H2), CD207 (CLEC4K/Langerin), CD209 (DC-SIGN/CLEC4L), CD302 (CLEC13A), CLEC1A, CLEC1B (CLEC-2), CLEC2A, CLEC2B, CD69, CLEC2D, CLEC2L, CLEC3A, CLEC3B, CLEC3O, CLEC3Q, CLEC4A, CLEC4C, CLEC4D (CLEC-6), CLEC4E, CLEC4F (KCLR), CLEC4G, CLEC4M (DC-SIGNR), CD209, CLEC5A, CLEC6A (Dectin-2), CLEC7A (Dectin-1), CLEC9A, CLEC10A, CLEC11A, CLEC12A, CLEC14A, FCER2, KLRB1, KLRF1, LY75 (DEC205), MRC1, MRC1 L1, MRC2 (Endo180), OLR1, PLA2R1, DCAL1, and COLEC10. Homologues of any of these genes are also contemplated, as are orthologues from other animal species such as mice and rats. Homologues and orthologues may be 50%, 70%, 80%, 80.6%, 83%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to any of the enumerated C-type lectin genes. A specifically contemplated orthologue is the Kupffer Cell Receptor (mKCR) gene in mice (homologous to human CLEC4F).

TREM genes and TREML genes that are contemplated for use in the present disclosure include, but are not limited to the following human genes: CD300 Antigen Like Family Member B (CD300LB), CD300 Antigen Like Family Member G (CD300LG), TREM1, TREM2, TREML1 (TLT1), TREML2 (TLT2), TREML3 (TLT3), and TREML4 (TLT4). Homologues of any of these genes are also contemplated, as are orthologues from other animal species such as mice and rats. Homologues and orthologues may be 50%, 70%, 80%, 80.6%, 83%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to any of these enumerated genes. Specifically contemplated orthologues include mTREM1, mTREM2, mTLT1, and mTLT4 from mouse.

TLR genes that are contemplated for use in the present disclosure include, but are not limited to, the following human genes: TLR1, TLR2, TLR3, TLR4, TLR5, TLR6, TLR7, TLR8, TLR9, TLR10, TLR11, TLR12, and TLR13. Homologues of any of these genes are also contemplated, as are orthologues from other animal species such as mice and rats. Homologues and orthologues may be 50%, 70%, 80%, 80.6%, 83%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to any of the enumerated TLR genes.

SIGLEC genes that are contemplated for use in the present disclosure include, but are not limited to, the following human genes: CD22, CD33, Myelin Associated Glycoprotein (MAG), SIGLEC5, SIGLEC6, SIGLEC7, SIGLEC8, SIGLEC9, SIGLEC10, SIGLEC11, SIGLEC12, SIGLEC13, and Sialoadhesin (SN). Homologues of any of these genes are also contemplated, as are orthologues from other animal species such as mice and rats. Homologues and orthologues may be 50%, 70%, 80%, 80.6%, 83%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to any of the enumerated SIGLEC genes.

Other innate immunity receptors suitable for use in the instant disclosure include those recited in the Examples below.

The fusion protein may comprise the entire extracellular domain of the innate immunity receptor, including a carbohydrate recognition domain, or it may comprise a portion of the extracellular domain, including a carbohydrate recognition domain, or it may comprise only a carbohydrate recognition domain.

The heterologous polypeptide may comprise any polypeptide to which a carbohydrate recognition domain of an innate immunity receptor may be fused such that the heterologous polypeptide does not interfere with the binding of a carbohydrate domain to its cognate specific carbohydrate, either in vivo or in vitro. Preferably, the heterologous polypeptide is an immunoglobulin, such as human IgG1, IgG2a, IgG2b, IgG3, IgG4, IgM, IgE, IgD, IgAa, and IgA2, or an immunoglobulin from other animal species. Preferably, a fragment of an immunoglobulin is used as the heterologous polypeptide, for example an Fc fragment of an IgG. In preferred embodiments, the heterologous polypeptide is an immunoglobulin variant that does not bind to human Fc receptors. Such variants are well known in the art. For example, a human IgG1 Fc variant comprising the following mutations may be used: L234A, L235E, G237A, and P331S.

The heterologous polypeptides may further comprise one or more functional domains that permit the fusion polypeptide to be immobilized on a solid support, or purified from a complex mixture. By way of example, the heterologous polypeptide may comprise a His6 tag to permit attachment of the fusion protein to a Ni-NTA solid support according to methods well known in the art. Also by way of example, the heterologous polypeptide may comprise a glutathione-S-transferase domain so that the resulting fusion protein can be adsorbed onto, for example, glutathione beads or glutathione derivatized microtiter plates.

The heterologous polypeptide may also comprise one or more biotins, or biotin derivatives. In this way, fusion proteins may be immobilized to streptavidin-conjugated solid supports, or a streptavidin-conjugated enzyme may be bound to the fusion protein.

The fusion protein may optionally further comprise a linker between the heterologous polypeptide and a carbohydrate recognition domain of the innate immunity receptor. The linker may be a peptide linker, or it may be a non-peptidic linker, such as a polyethylene glycol.

The carbohydrate recognition domain may be C-terminal relative to the heterologous polypeptide or it may be N-terminal relative to the heterologous polypeptide in the fusion protein.

The fusion proteins of the disclosure may be prepared by any method known in the art for the production of proteins. Preferably, the fusion proteins are prepared using recombinant DNA technology and protein expression technology well known in the art. For example, DNA encoding the carbohydrate recognition domain of an innate immunity receptor may be obtained by reverse-transcriptase PCR (RT-PCR) of mRNA using primers specific for the carbohydrate recognition domain of the particular innate immunity receptor of interest. The resulting DNA may then be cloned into an expression vector in frame with DNA encoding the heterologous polypeptide sequence. Expression vectors useful in the present disclosure typically contain an origin of replication, a promoter located 5' to (i.e., upstream of) and followed by the DNA sequence coding for the fusion protein, transcription termination sequence, and the remaining vector. The expression vectors may also include other DNA sequence known in the art, for example, stability leader sequences that provide for stability of the expression product, secretory leader sequences which provide for secretion of the expression product, and sequences which allow expression of the fusion protein to be modulated or induced. The expression vector may also contain viral sequences that allow the fusion protein to be expressed using a viral expression system, such as the baculovirus expression system well known in the art. The expression vector may be introduced into host cells, such as microbial cells, yeast cells, mammalian cells, or insect cells. The expression vector may be introduced into cells as naked DNA, or it may be encapsulated within a virus (such as a baculovirus). The expression vector may be maintained within the host cell, or it may integrate into the host cell genome.

Preferably, the expression vector comprises DNA sequence that lead to the addition of a secretory leader sequence on the fusion protein, thereby causing the fusion protein to be secreted into the medium surrounding the host cells. The fusion protein can then be purified from the medium using techniques known in the art. By way of example, if the fusion protein comprises IgG as the heterologous polypeptide, then a Protein A column may be used to bind to the fusion protein to permit the fusion protein to be partitioned from other proteins in the surrounding medium.

Fusion proteins may also be produced by in vitro translation of a mRNA encoding the fusion protein using an in vitro expression system, such as a *Xenopus* oocyte expression system.

In an embodiment, the fusion proteins are produced separately and then coupled to one another using chemical techniques known in the art. For example, the carbohydrate recognition domain and the heterologous polypeptide may be produced separately and then coupled to one another using glutaraldehyde.

Following production of the fusion protein, the fusion protein may be labeled with a detectable label, such as a fluorophore, radiolabel, an enzyme, an enzyme substrate, a dye, a chemiluminescent agent, a magnetic particle, a quantum dot, or any other moiety that produces, directly or indirectly, a detectable signal. Many methods for the conjugation of such detectable labels to proteins are known in the art. By way of example only, an N-hydroxysuccinimide-activated dye, most preferably an N-hydroxysuccinimide-activated fluorophore, may be conjugated to the fusion protein by reaction with primary amines on the fusion protein.

In some embodiments, the fusion protein is biotinylated using methods known in the art such that the fusion protein comprises one or more biotins, or one or more biotin derivatives. In this way, the fusion protein may be attached to a streptavidin-detectable moiety conjugate, such as an enzyme-streptavidin conjugate.

In one series of embodiments, the fusion proteins of the disclosure are used to determine whether a specific carbohydrate component is present in a composition that comprises a polysaccharide. The methods involve contacting the polysaccharide with a fusion protein that binds to a specific carbohydrate component of a polysaccharide, and then determining whether the fusion protein has bound to polysaccharide in the composition. For example, it is known that the carbohydrate recognition domain of CLEC7A (also known as Dectin-1), can interact with β-1,3-D-glycans (see Brown, G. D. and Gordon, S., 2001, Nature 413, 36-7, incorporated herein by reference in its entirety). Binding of a fusion protein comprising the carbohydrate recognition domain of CLEC7A to a polysaccharide composition therefore indicates that the polysaccharide composition comprises β-1,3 glucan. Similarly, since the rodent Kupffer cell receptor (KCR; homologous to human CLEC4F) has high affinity to D-galactose and N-acetylgalactosamine, and is able to clear D-galactose and D-fucose terminated glycoproteins from serum (see Fadden, A. J., Holt, O. J. and Drickamer, K. (2003), Glycobiology 13, 529-37, incorporated herein by reference in its entirety), binding of a fusion protein comprising the carbohydrate recognition domain of KCR to a polysaccharide composition therefore indicates that the polysaccharide composition comprises D-galactose and/or N-acetylgalactosamine and/or D-galactose terminated glycoproteins and/or D-fucose terminated glycoproteins. In addition, CD209 (also known as DC-SIGN and CLEC4L) and CLEC4M (also known as DC-SIGNR and L-SIGN) can both bind to $Man_9GlcNAc_2Asn$ glycopeptide, but only CD209 and not CLEC4M can bind to glycans with a terminal fucose residue (see Guo et al (2004) Nat Struct Mol Biol 11, 591-8); therefore, fusion proteins of CD209 and CLEC4M can discriminate between polysaccharide compositions comprising these carbohydrate components. The methods and reagents of the disclosure may therefore be used to determine the identity of the carbohydrate components of a polysaccharide composition and to determine the relative amounts of those carbohydrate components e.g. to "fingerprint" a polysaccharide composition. For example, the methods and reagents of the disclosure may be used to determine the carbohydrate components of a polysaccharide composition that has immunomodulatory activity.

In addition, if one knows the identity of the cells that express the innate immunity receptors from which the carbohydrate recognition domain of the fusion protein is derived, then the assays disclosed herein reveal the identity of the cells in the body that bind to the polysaccharide under investigation. Such knowledge, for example, can help reveal the mechanism by which a particular polysaccharide composition (such as polysaccharides isolated from *Ganoderma lucidum*) exerts beneficial or deleterious effects on an organism which comes into contact with the polysaccharide. It is not necessary to know the identity of the carbohydrate component bound by the carbohydrate recognition domain in this embodiment.

The binding of the fusion proteins of the disclosure to their cognate carbohydrate component can be performed by immobilizing the composition comprising the polysaccharide to a solid support, and then contacting the solid support with a fusion protein. Binding of the fusion protein may be detected by detecting the presence of the fusion protein on the surface of the solid support, for example, by detecting the presence of the heterologous polypeptide on the surface of the solid support or by detecting the presence of the carbohydrate recognition domain on the surface of the solid support. For example, if the heterologous polypeptide is conjugated to a fluorophore, then the presence of the fluorophore, following washing, on the surface of the solid support is indicative of the presence of the fusion protein, which in turn is indicative of the presence of a polysaccharide comprising the specific carbohydrate component recognized by the carbohydrate recognition domain of the fusion protein.

As used herein, "solid support" is defined as any surface to which molecules may be attached through either covalent or non-covalent bonds. This includes, but is not limited to, membranes (for example, polyvinylidene fluoride (PVDF) membranes), plastics (for example, microtiter plates), paramagnetic beads, charged paper, nylon, Langmuir-Bodgett films, functionalized glass, germanium, silicon, PTFE, polystyrene, gallium arsenide, gold and silver. Any other material known in the art that is capable of having functional groups such as amino, carboxyl, thiol or hydroxyl incorporated on its surface, is also contemplated. This includes surfaces with any topology, including, but not limited to, spherical surfaces, grooved surfaces, and cylindrical surfaces e.g., columns.

The composition comprising a polysaccharide (also referred to herein as a "polysaccharide composition") can be, without limitation, any composition that includes a polysaccharide including, for example, a glycoprotein (including a proteoglycan), a glycolipid, peptidoglycan, a microbial cell wall, a viral particle, and a fungal cell wall. In other embodiments, the composition comprising a polysaccharide is a polysaccharide free in solution e.g. a polysaccharide that is not attached to a protein or lipid. As used herein, a "polysaccharide" means a carbohydrate molecule that comprises two or more monosaccharides.

Immobilization of the composition comprising a polysaccharide on a solid support may be achieved, for example, by biotinylating the polysaccharides in the composition, and then immobilizing on a streptavidin-conjugated solid support. In addition, polysaccharides may be immobilized on, for example, methanol-activated PVDF membranes. It is specifically contemplated that the methods of the disclosure can be performed in a "dot blot" format using dots of polysaccharide immobilized on a PVDF membrane.

In some embodiments, binding of the fusion protein to an immobilized polysaccharide is detected by binding a secondary reagent to the fusion protein, preferably to the heterologous polypeptide, and then detecting the presence of the secondary reagent. For example, a biotinylated fusion protein may be attached to a streptavidin-conjugated enzyme, and the presence of the enzyme detected by adding a substrate that yields a detectable product. A non-biotinylated fusion protein may be detected using, for example, an antibody that binds to the heterologous polypeptide (such as an anti-IgG antibody if the heterologous polypeptide is IgG, or a IgG Fc), which secondary antibody is conjugated to an enzyme. For example, if the enzyme is horseradish peroxidase (HRP), then detection of fusion protein binding may be performed using the Enhanced Chemiluminescence (ECL) technique well known in the art. The secondary reagent may also, or alternatively, be conjugated to a detectable label such as a fluorophore or a radionuclide. Many other techniques are known in the art which may be used to detect the binding of the disclosed fusion proteins to a solid support.

It is specifically contemplated that the aforementioned assays may be carried out in a multiplexed array format. For example, a solid support may be partitioned into a plurality of spatially discrete addresses onto which a plurality of different compositions may be bound. Then the solid support may be contacted with a fusion protein, and the binding of the fusion protein detected. In this way, it can be determined which, if any, of the immobilized polysaccharide compositions comprises the particular carbohydrate component bound by the carbohydrate recognition domain of the fusion protein.

In another embodiment, a single composition is immobilized on a solid support which is partitioned into a plurality of spatially discrete addresses. Each address is then contacted with a different fusion protein, each different fusion protein comprising a different carbohydrate recognition domain. Following washing to remove non-specifically bound material, binding of the fusion proteins may then be detected as described above; the spatial address of each binding reaction detected reveals the identity of the fusion protein that has bound. In this way, the composition can be probed with a number of different fusion proteins in parallel. In this embodiment, each fusion protein may comprise the same heterologous polypeptide, thereby allowing a single secondary reagent to simultaneously detect binding at each address. For example, if each fusion protein comprises IgG Fc as the heterologous polypeptide, then either an anti-IgG antibody, or Protein A, or Protein G, may be used to detect binding of the fusion protein.

The fusion proteins and methods of the disclosure may be used to "fingerprint" any composition which comprises polysaccharides, including, but not limited to, polysaccharide compositions obtained from herbal preparations, such as polysaccharide-containing fractions isolated from the fungi Reishi (*Ganoderma lucidim*), *Cordyceps sinensis*, and *Lentinus edodes*; and from the plant *Dendrobium huoshanense*. In particular, it is specifically contemplated that the methods used herein are used to determine the carbohydrate components of the F3 polysaccharide fraction of Reishi polysaccharide (see Wang, et al (2002) Bioorg Med Chem 10, 1057-62; Chen, et al (2004) Bioorg Med Chem 12, 5595-601; Chien, et al (2004) Bioorg Med Chem 12, 5603-9.; and Hsu et al (2004)

J Immunol 173, 5989-99, each of which is specifically incorporated herein by reference in its entirely).

The methods provided herein can be used to "fingerprint" complex mixtures that include a number of different polysaccharide compositions, or they can be used on preparations that contain only a single polysaccharide species e.g. a single glycoprotein or a single polysaccharide.

If one knows the identity of the cells that express the innate immunity receptor from which the carbohydrate recognition domain is derived, then the aforementioned assays reveal which cells in the body bind to the polysaccharide upon introduction of the polysaccharide composition into the body. It is then possible to obtain agents that modulate the activity of the identified innate immunity receptor. For example, agents that mimic the structure of the polysaccharide or that potentiate the interaction of the polysaccharide with the innate immunity receptor may be generated if interaction of the innate immunity receptor with the polysaccharide leads to beneficial effects in the body. See the section below entitled "Modulators."

In another series of embodiments, the methods and fusion proteins of the disclosure are used to determine the identity of polysaccharides displayed on the surface of a pathogen, such as a fungal cell, a bacterial cell, or a virus, such as an enveloped virus, including but not limited to influenza virus, and also including but not limited to viruses from the Flaviviridae family. Flaviviridae viruses suitable for use in the methods disclosed herein include, but are not limited to, members of the genus *Flavivirus* (such as, for example, Dengue virus, West Nile Virus, Japanese encephamyelitis virus (JEV), yellow fever virus, and tick-borne encephamyelitis virus) and members of the genus *Hepacivirus* (such as, for example, Hepatitis C virus). In one such embodiment, a fusion protein is immobilized on a solid support (for example, using a Protein A derivatized solid support if the heterologous polypeptide is IgG or a fragment thereof), and the solid support is this contacted with a composition comprising the pathogen of interest. Following washing, the binding of the pathogen is then detected using, for example, a secondary reagent that binds specifically to the pathogen in a manner that does not compete with the binding of the fusion protein. For example, a secondary antibody that is specific for the pathogen may be used. Binding of the secondary reagent is then detected as described above (for example using HRP-conjugated secondary antibody), or it may be detected using a tertiary reagent that binds to the secondary reagent (for example, using an anti-IgG antibody conjugated to HRP if the secondary reagent is an anti-pathogen IgG). If binding of the secondary reagent is detected, then this reveals that the pathogen comprises a polysaccharide that comprises the specific carbohydrate component recognized by the carbohydrate recognition domain of the fusion protein.

Alternatively, the assay may be performed by immobilizing a reagent that binds specifically to the pathogen on a solid support. For example, an antibody which binds to the pathogen can be immobilized on a solid support, then contacted with a composition comprising the pathogen. The solid support is then contacted with the fusion protein(s), and the binding of the fusion proteins is then detected as described above (preferably, the fusion protein does not compete for pathogen binding with the immobilized reagent). For example, if the heterologous polypeptide of the fusion protein is IgG Fc, then an anti-IgG antibody can detect binding of the fusion protein to the pathogen; alternatively, if the fusion protein is conjugated to a detectable label, then detection of the label is used to detect binding.

It is expressly contemplated that the aforementioned pathogen assays can be carried out in a multiplexed format using, for example, a plurality of different fusion proteins simultaneously. For example, an antibody that binds to the pathogen may be immobilized at a plurality of discrete addresses on a solid support; then the solid support is contacted with a composition comprising the pathogen; and then each specific address is contacted with a different fusion protein, each different fusion protein comprising a different carbohydrate recognition domain. If each fusion protein comprises the same heterologous polypeptide, then binding of the fusion protein may be detected using a single reagent that binds to the heterologous polypeptide. For example, if the heterologous polypeptide is IgG Fc, then an anti-IgG antibody can be used to detect binding of the fusion protein(s). The spatial address of each binding reaction then reveals the identity of the fusion protein. Alternatively, a multiplexed assay may be carried out using a plurality of different fusion proteins immobilized on the solid support at spatially discrete addresses, by contacting the solid support with the composition comprising the pathogen, followed by contacting the solid support with a secondary reagent that binds specifically to the pathogen. For example, if the pathogen is Dengue virus, then the secondary reagent may be an antibody against the E envelope protein. As in all the preceding assays, washing may be used to remove non-specifically bound material from the solid support.

Using the methods disclosed herein, it has been discovered that Dengue virus binds to DVLR1/MDL-1 on the surface of CD14+ macrophages. See Example 11. It has further been shown that DVLR1/MDL-1 binding to Dengue virus results in the activation of DAP12, which in turn leads to the release of the proinflammatory cytokines TNF-α, MIP-1 α, IFN-α, and IL-8 from macrophages. See Example 12. The release of these cytokines is implicated in the development of Dengue hemorrhagic fever (DHF) and Dengue shock syndrome (DSS).

Knowledge of the identity of the innate immunity receptor(s) that interact with a pathogen may then be used to develop agents that modulate the activity of the innate immunity receptor. For example, modulators that activate an identified innate immunity receptors may be obtained in order to augment the immune response to a particular pathogen. In cases where interaction of an innate immunity receptor to a particular polysaccharide composition is detrimental to the body (for example, when a pathogen causes excessive inflammation), modulators may be obtained that reduce the activity of the innate immunity receptors. For example, agents (such as antibodies) that block the binding of a pathogen to an innate immunity receptor may be used to prevent the occurrence of an undesirable proinflammatory reaction to infection with said pathogen. Similarly, if the screening methods disclosed herein reveal that a particular pathogen (such as a virus) uses an innate immunity receptor to gain entry into a cell, then an agent that blocks the binding of the pathogen to the innate immunity receptor will prevent entry of the pathogen into the cell.

In another series of embodiments, the fusion proteins of the disclosure are used to disrupt or prevent the interaction between a polysaccharide and an innate immunity receptor on a cell surface. In this series of embodiments, the fusion protein comprises the carbohydrate recognition domain of the innate immunity receptor that is expressed on the cell surface. The cell expressing the innate immunity receptor is then contacted with the fusion protein, either in vivo or in vitro, whereby the fusion protein competes with the polysaccharide for binding to the innate immunity receptor.

If interaction of the polysaccharide with the innate immunity receptor on the cell surface leads to deleterious effects in an organism, then a therapeutically effective amount of the fusion protein may be administered to the organism in a pharmaceutical composition to prevent or diminish the interaction. Preferably, the heterologous polypeptide of the administered fusion protein does not bind to an any cell surface receptor. For example, the heterologous polypeptide may be comprised of a mutated variant of IgG Fc that does not bind to Fc receptors on cell surfaces.

Purification

In another series of embodiments, the fusion proteins are used to at least partially purify or isolate polysaccharides that comprise the specific carbohydrate component recognized by the carbohydrate recognition domain of the fusion protein. For example, the fusion protein may be immobilized on a solid support, and a composition suspected of containing, or known to contain, a polysaccharide composition is contacted with the solid support. If the composition comprises a polysaccharide that can bind to the carbohydrate recognition domain of the fusion protein, then that polysaccharide will bind to the fusion protein. The solid support can then be washed to remove non-specifically bound components of the composition, and the bound polysaccharide may then be eluted by dissociating the interaction with the fusion protein, and collected. For example, if the fusion protein comprises the carbohydrate recognition domain of a lectin receptor, then the interaction may be dissociated using EDTA to chelate $Ca^{2+}$. In this way, it is possible to purify specific polysaccharide compositions from complex mixtures. In preferred embodiments, this method is used to purify polysaccharides isolated from *Ganoderma lucidum* (Reishi).

For the aforementioned purification method, the solid support may comprise, for example, a column to which the fusion protein is bound. Suitable columns include Sepharose Protein A columns, to which fusion proteins comprising IgG as the heterologous polypeptide may be bound via interaction with of the IgG domain of the fusion protein with Protein A. Alternatively, CNBr activated column media may be bound to fusion proteins.

The present disclosure also provides kits that can be used in any of the above methods. In one embodiment, a kit comprises a fusion protein according to the disclosure, in one or more containers. The kit may also comprise a secondary reagent, such as an antibody that specifically binds to the heterologous polypeptide domain of the fusion protein e.g. an anti-IgG antibody if the heterologous polypeptide is IgG, or a fragment thereof. The kit may also comprise reagents and buffers for detecting the binding of a fusion protein to a polysaccharide. For example, in embodiments where a HRP-conjugated secondary antibody is used to detect the binding of a fusion protein to a polysaccharide, the kit may comprise the reagents necessary to establish an enhanced chemiluminescence reaction e.g. one or more containers comprising luminol, p-coumaric acid, Tris buffer, and hydrogen peroxide. The kit may also comprise one or more positive control polysaccharides. The kit may also comprise one or more solid supports for use in the aforementioned methods, for example, one or more PVDF membranes or one or more multiwell microtiter plates.

Modulators

As described above, the methods of the disclosure identify innate immunity receptor(s) that interact with a particular polysaccharide. This information then allows one to obtain modulators of the identified innate immunity receptor. A modulator can be an agonist, an antagonist (including competitive and non-competitive antagonists), or an inverse agonist of an innate immunity receptor. A modulator may, without limitation: inhibit the binding of a polysaccharide to an innate immunity receptor; potentiate the binding of a polysaccharide to an innate immunity receptor; or function as a mimetic of a polysaccharide that binds to an innate immunity receptor, thereby activating the innate immunity receptor even in the absence of the polysaccharide.

Modulators of innate immunity receptors include antibodies. For example, an antagonistic antibody against an innate immunity receptor can prevent binding of a pathogen to the innate immunity receptor. In some cases, such an antibody is a neutralizing antibody as it prevents the entry of the pathogen into the cell that expresses the innate immunity receptor. Alternatively, an agonistic antibody may function as a mimetic of a polysaccharide composition that exerts a beneficial effect on a cell. An antagonistic antibody may also bind to an innate immunity receptor in such a way as to block the downstream signaling by the receptor upon pathogen binding. Antibodies may be, without limitation, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies, and epitope-binding fragments of any of the above. The term “antibody,” as used herein, refers to immunoglobulin molecules and immunologically active portions of immunoglobulin molecules, i.e., molecules that contain an antigen binding site that immunospecifically binds an antigen. The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term “antibody” (Ab) or “monoclonal antibody” (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. 24: 316-325 (1983)). Methods for producing antibody agonists are described in, for example, PCT publication WO 96/40281; U.S. Pat. No. 5,811,097; Deng et al., Blood 92 (6): 1981-1988 (1998); Chen et al., Cancer Res. 58 (16): 3668-3678 (1998); Harrop et al., J. Immunol. 161 (4): 1786-1794 (1998); Zhu et al., Cancer Res. 58 (15): 3209-3214 (1998); Yoon et al., J. Immunol. 160 (7): 3170-3179 (1998); Prat et al., J. Cell. Sci. 111 (Pt2): 237-247 (1998); Pitard et al., J. Immunol. Methods 205 (2): 177-190 (1997); Liautard et al., Cytokine 9 (4): 233-241 (1997); Carlson et al., J. Biol. Chem. 272 (17): 11295-11301 (1997); Taryman et al., Neuron 14 (4): 755-762 (1995); Muller et al., Structure 6 (9): 1153-1167 (1998); Bartunek et al., Cytokine 8 (1): 14-20 (1996); Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (which are all incorporated by reference herein in their entireties).

The disclosure provides non-limiting specific examples of anti-DVLR1 monoclonal antibodies that prevent TNF-α release from macrophages following DV infection. See Example 15. These antibodies can be used in the pharmaceutical compositions and the methods of treatment specified herein, particularly in compositions and methods for the treatment or prophylaxis of DV infection in humans.

Modulators of innate immunity receptors also include small molecules identified by high throughput screening methods. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that bind to the innate immunity receptor of interest. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, Int. J. Pept. Prot. Res., 37: 487-493; and Houghton et al., 1991, Nature, 354: 84-88). Other chemistries for generating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, Proc. Natl. Acad. Sci. USA, 90: 6909-6913), vinylogous polypeptides (Hagihara et al., 1992, J. Amer. Chem. Soc., 114: 6568), nonpeptidal peptidomimetics with glucose scaffolding (Hirschmann et al., 1992, J. Amer. Chem. Soc., 114: 9217-9218), analogous organic synthesis of small compound libraries (Chen et al., 1994, J. Amer. Chem. Soc., 116: 2661), oligocarbamates (Cho et al., 1993, Science, 261: 1303), and/or peptidyl phosphonates (Campbell et al., 1994, J. Org. Chem., 59: 658), nucleic acid libraries (for example, see U.S. Pat. No. 5,270,163 describing the generation of nucleic acid ligands, also known as "aptamers"), peptide nucleic acid libraries (U.S. Pat. No. 5,539,083), antibody libraries (e.g., Vaughn et al., 1996, Nature Biotechnology, 14 (3): 309-314) and PCT/US96/10287), carbohydrate libraries (e.g., Liang et al., 1996, Science, 274-1520-1522) and U.S. Pat. No. 5,593,853), small organic molecule libraries (e.g., benzodiazepines, Baum C & EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

Pharmaceutical Compositions

The instant disclosure also provides pharmaceutical compositions. In some embodiments, the pharmaceutical compositions comprise the fusion proteins of the disclosure. In other embodiments, the pharmaceutical compositions comprise a modulator of an innate immunity receptor (for example antibodies against an innate immunity receptor such as DVLR1, including the antibodies exemplified in Example 15). In such pharmaceutical compositions, the fusion protein or the innate immunity receptor modulator form the "active compound." In some embodiment, the pharmaceutical compositions are administered to a subject in order to treat or prevent diseases or disorders characterized by the binding of a polysaccharide to an innate immunity receptor on the surface of a cell in that subject. In other embodiments, the pharmaceutical compositions are administered to a subject to activate an innate immunity receptor in circumstances where increasing the activity of that receptor is beneficial to the subject. In still other embodiments, the pharmaceutical compositions are administered to a subject to potentiate the binding of a polysaccharide composition to an innate immunity receptor.

In addition to active compound, the pharmaceutical compositions preferably comprise at least one pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Subject as used herein refers to humans and non-human primates (e.g. guerilla, macaque, marmoset), livestock animals (e.g. sheep, cow, horse, donkey, pig), companion animals (e.g. dog, cat), laboratory test animals (e.g. mouse, rabbit, rat, guinea pig, hamster), captive wild animals (e.g. fox, deer) and any other organisms who can benefit from the agents of the present disclosure. There is no limitation on the type of animal that could benefit from the presently described agents. The most preferred subject of the present disclosure is a human. A subject regardless of whether it is a human or non-human organism may be referred to as a patient, individual, animal, host or recipient.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in subjects. The dosage of such compounds lies preferably within a range of circulating concentrations that include the ED50 with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in subjects. Levels in plasma can be measured, for example, by high performance liquid chromatography.

As defined herein, a therapeutically effective amount of an active compound of the disclosure may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. Without limitation, the active compound can be administered between one time per week and three or more times per day, for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a pharmaceutical composition of the disclosure can include a single treatment or, preferably, can include a series of treatments.

Gene Therapy and RNAi

Constructs encoding the fusion proteins of the disclosure can be used as a part of a gene therapy protocol to deliver therapeutically effective doses of a receptor fusion protein to a subject. A preferred approach for in vivo introduction of nucleic acid into a cell is by use of a viral vector containing nucleic acid, encoding a fusion protein of the disclosure. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous nucleic acid molecules encoding fusion proteins in vivo. These vectors provide efficient delivery of nucleic acids into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) Blood 76:27 1). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10-9.14 and other standard laboratory manuals.

Another useful viral gene delivery system uses adenovirus-derived vectors. The genome of an adenovirus can be manipulated such that it encodes and expresses a gene product of interest but is inactivated in terms of its ability to replicate in a normal lytic viral life cycle. See, for example, Berkner et al., BioTechniques 6:616 (1988); Rosenfeld et al., Science 252: 431-434 (1991); and Rosenfeld et al., Cell 68:143-155 (1992). Suitable adenoviral vectors derived from the adenovirus strain Ad type 5 d1324 or other strains of adenovirus (e.g., Ad2, Ad3, Ad7 etc.) are known to those skilled in the art. Recombinant adenoviruses can be advantageous in certain circumstances in that they are not capable of infecting non-dividing cells and can be used to infect a wide variety of cell types, including epithelial cells (Rosenfeld et al., (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated, into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., cited supra; Haj-Ahmand et al., J. Virol. 57:267 (1986)).

In another embodiment, non-viral gene delivery systems of the present disclosure rely on endocytic pathways for the uptake of the subject nucleotide molecule by the targeted cell. Exemplary gene delivery systems of this type include liposomal derived systems, poly-lysine conjugates, and artificial viral envelopes. In a representative embodiment, a nucleic acid molecule encoding a fusion protein of the disclosure can be entrapped in liposomes bearing positive charges on their surface (e.g., lipofectins) and (optionally) which are tagged with antibodies against cell surface antigens of the target tissue (Mizuno et al. (1992) No Shinkei Geka 20:547-551; PCT publication WO91/06309; Japanese patent application 1047381; and European patent publication EP-A43075).

Gene delivery systems for a gene encoding a fusion protein of the disclosure can be introduced into a subject by any of a number of methods. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3 054-3057). The pharmaceutical preparation of the gene therapy construct can consist essentially of the gene delivery system in an acceptable diluent, or can comprise a slow release matrix in which the gene delivery vehicle is imbedded. Where the fusion protein can be produced intact from recombinant cells, e.g. retroviral vectors, the pharmaceutical preparation can comprise one or more cells which produce the fusion protein.

In another embodiment, the expression of an innate immunity receptor that is identified according to the methods disclosed herein as being involved in the pathogenesis is reduced or completely inhibited using RNA interference (RNAi). RNAi is well known in the art and may be accomplished using small interfering RNA (siRNA). siRNAs according to the invention could have up to 29 bps, 25 bps, 22 bps, 21 bps, 20 bps, 15 bps, 10 bps, 5 bps or any integer thereabout or therebetween. Such siRNAs can be administered, e.g., in a form encoded by a vector (for example, a vector encoding a small hairpin RNA (shRNA)) or as a liposome nucleic acid complex. The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787). Accordingly, the present disclosure also provides pharmaceutical compositions comprising RNA molecules that are capable of mediating RNA interference of an innate immunity receptor when administered to a subject.

The present disclosure provides a non-limiting example of the RNAi-mediated "knock down" of the DVLR1 gene in macrophages. The attenuation of DVLR1 in this manner significantly reduces the secretion of proinflammatory cytokines in DV-infected macrophages, thereby indicating that RNAi-mediated attenuation of DVLR1 will be useful for the treatment of DV.

It is specifically contemplated that siRNA or shRNA that attenuates expression of DVLR1 is used for the RNAi-mediated treatment of subjects infected with Dengue virus. Methods for designing, synthesizing, and administering shRNA and siRNA in order to attenuate the expression of a specific gene are well known in the art and are described in, for example, U.S. Pat. No. 7,022,828. Non-limiting examples of agents suitable for formulation with the shRNA constructs and siRNA molecules of the disclosure include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, for example the CNS (Jolliet-Riant and Tillement, 1999, Fundam. Clin. Pharmacol., 13, 16 26); biodegradable polymers, such as poly (DL-lactide-coglycolide) microspheres for sustained release delivery after implantation (Emerich, D F et al, 1999, Cell Transplant, 8, 47 58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941949, 1999). Other non-limiting examples of delivery strategies, including CNS delivery of the nucleic acid molecules of the instant disclosure include material described in Boado et al., 1998, J. Pharm. Sci., 87, 1308 1315; Tyler et al, 1999, FEBS Lett., 421, 280 284; Pardridge et al., 1995, PNAS USA., 92, 5592 5596; Boado, 1995, Adv. Drug Delivery Rev., 15, 73 107; Aldrian-Herrada et al., 1998, Nucleic Acids Res., 26, 4910 4916; and Tyler et al., 1999, PNAS USA., 96, 7053 7058. All these references are hereby incorporated herein by reference. In addition, compositions comprising surface-modified liposomes containing poly (ethylene glycol) lipids (PEG-modified, or long-circulating liposomes or stealth liposomes) may also be used with the nucleic acids of the disclosure. Nucleic acid molecules of the disclosure can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601 2627; Ishiwata et al., Chem. Pharm. Bull. 1995, 43, 1005 1011). Such liposomes have been shown to accumulate selectively in tumors, presumably by extravasation and capture in the neovascularized target tissues (Lasic et al., Science 1995, 267, 1275 1276; Oku et al., 1995, Biochim. Biophys. Acta, 1238, 86 90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864 24870; Choi et al., International PCT Publication No. WO 96/10391 Ansell et al., International PCT Publication No. WO 96/10390; Holland et al., International PCT Publication No. WO 96/10392; all of which are incorporated by reference herein). Long-circulating liposomes are also likely to protect drugs from nuclease degradation to a greater extent compared to cationic liposomes, based on their ability to avoid accumulation in metabolically aggressive MPS tissues such as the liver and spleen.

EXAMPLES

The present disclosure is further described by the following non-limiting examples:

Example 1

Preparation of Innate Immunity Receptor:Fc Fusion Protein

Cell Culture 293F cells (Invitrogen, R790-07) were cultured in serum-free 293 FREESTYLE 203 expression medium (Invitrogen, 12338-018) in a 125 mL flask on an orbital shaker (125 rpm) at 37° C. in a $CO_2$ incubator.

Construction of Receptor.Fc Fusion Genes

The extracellular domains of lectin receptors, TREMs and TLTs were cloned by the reverse-transcriptase polymerase chain reaction (RT-PCR), followed by subcloning into a yT&A vector and then into a pcDNA3.1 (+)hIgG1.Fc expression vector. The resulting receptor.Fc construct encodes recombinant proteins that are fused with a mutated human IgG1 Fc portion, which does not bind to human Fc receptors. The mutations in the IgG1 Fc portion are L234A, L235E, G237A, and P331S. The sequences of the primers used to RT-PCR amplify the extracellular domains are:

```
CLEC1A/CLEC-1
sense primer
5'-GAATCCTTTCAGTACTACCAGCTCTCC-3'    SEQ ID NO: 1 antisense primer
5'-GAATTCTCAGTCACCTTCGCCTAATGT-3'    SEQ ID NO: 2

CLEC1B/CLEC-2
sense primer
5'-GGATCCCTGGGGATTTGGTCTGTC-3'       SEQ ID NO: 3 antisense primer
5'-GAATTCTTAAGGTAGTTGGTCCAC-3'       SEQ ID NO: 4

CLEC2B/AICL
sense primer
5'-GGATCCTCTCAGAGTTTATGCCCC-3'       SEQ ID NO: 5 antisense primer
5'-GGATCCCCCCATTATCTTAGACAT-3'       SEQ ID NO: 6

CLEC4A/DCIR
sense primer
5'-GGATCCTTTCAAAAATATTCTCAGCTTCTT-3' SEQ ID NO: 7 antisense primer
5'-GAATTCTCATAAGTGGATCTTCATCATC-3'   SEQ ID NO: 8

CLEC4C/BDCA-2
sense primer
5'-GGATCCTTTATGTATAGCAAAACTGTCAAG-3' SEQ ID NO: 9 antisense primer
5'-GAATTCTTATATGTAGATCTTCTTCATCTT-3' SEQ ID NO: 10

CLEC4D/CLEC-6
sense primer
5'-GAATCCCATCACAACTTTTCACGCTGT-3'    SEQ ID NO: 11
```

-continued antisense primer
5'-GAATTCCTAGTTCAATGTTGTTCCAGG-3'   SEQ ID NO: 12

CLEC4E/MINCLE
sense primer
5'-GAAGATCTACATTTCGCATCTTTCAAACC-3'   SEQ ID NO: 13 antisense primer
5'-GCGGTTAAAGAGATTTTCCTTTGTTCA-3'   SEQ ID NO: 14

CLEC4K/Langerin
sense primer
5'-GGATCCCGGTTTATGGGCACCATA-3'   SEQ ID NO: 15 antisense primer
5'-GGATCCTCACGGTTCTGATGGGAC-3'   SEQ ID NO: 16

CLEC4L/DC-SIGN
sense primer
5'-GGATCCAAGGTCCCCAGCTCCATAAG-3'   SEQ ID NO: 17 antisense primer
5'-GAATTCCTACGCAGGAGGGGGT-3'   SEQ ID NO: 18

CLEC4M/DC-SIGNR/L-SIGN
sense primer
5'-GGATCCTCCAAGGTCCCCAGCTCC-3'   SEQ ID NO: 19 antisense primer
5'-GAATTCCTATTCGTCTCTGAAGCAGG-3'   SEQ ID NO: 20

CLEC5A/MDL-1
sense primer
5'-AGATCTAGTAACGATGGTTTCACCAC-3'   SEQ ID NO: 21 antisense primer
5'-GAATTCCTGTGATCATTTGGCATTCTT-3'   SEQ ID NO: 22

CLEC6A/Dectin-2
sense primer
5'-GGATCCACATATGGTGAAACTGGC-3'   SEQ ID NO: 23 antisense primer
5'-GAATTCCATCAGTCGATGGGC-3'   SEQ ID NO: 24

CLEC7A/Dectin-1
sense primer
5'-GGATCCACCATGGCTATTTGGAGATCC-3'   SEQ ID NO: 25 antisense primer
5'-GAATTCTTACATTGAAAACTTCTTCTCACA-3'   SEQ ID NO: 26

CLEC10A/ML2
sense primer
5'-GGATCCTCCAAATTTCAGAGGGACCTG-3'   SEQ ID NO: 27 antisense primer
5'-GAATTCTCAGTGACTCTCCTGGCTG-3'   SEQ ID NO: 28

CLEC12A/CLL-1
sense primer
5'-GGATCCGTAACTTTGAAGATAGAAATGAAA-3'   SEQ ID NO: 29 antisense primer
5'-GAATTCCTCATGCCTCCCTAAAATATGTA-3'   SEQ ID NO: 30

CLEC13A/BIMLEC
sense primer
5'-GGATCCTCATGCTCCGGGCCGCG-3'   SEQ ID NO: 31 antisense primer
5'-GAATTCGCTAGCAATCACCAATGCTGA-3'   SEQ ID NO: 32

COLEC12/CL-P1
sense primer
5'-AGAGGTGACAGAGGATCCCA-3'   SEQ ID NO: 33 antisense primer
5'-GAATTCGTGATCCCATCACAGTCC-3'   SEQ ID NO: 34

MAFA-L/KLRG-1
sense primer
5'-GGATCCTGCCAGGGCTCCAACT-3'   SEQ ID NO: 35 antisense primer
5'-ATGACAGATCTGAGGGTCA-3'   SEQ ID NO: 36

Expression and Purification of Recombinant Receptor.Fc Fusion Proteins

The receptor.Fc proteins were over-expressed using the FREESTYLE 293 Expression System (Invitrogen, Carlsbad, Calif.) and purified on protein A columns. Briefly, $3 \times 10^7$ 293-F cells were spun down at 1,500 rpm, then resuspended in 28 ml FREESTYLE 293 expression medium. Then, 40 µl of 293FECTIN was mixed with 1 ml OPTI-MEM (Invitrogen, 31985-062) for 5 min at room temperature, then incubated with 30 µg plasmid DNA in 1 ml OPTI-MEM (Invitrogen, 31985-062) for another 20 min, before addition to the 293-F cells. After 48 h, the supernatant was harvested and the recombinant fusion proteins were purified by protein A columns.

Example 2

Preparation of Polysaccharide Extracts

Crude Extracts of Reishi

Crude Reishi extract (prepared via alkaline extraction, neutralization and ethanol precipitation) was obtained from Pharmanex Co. (CA, USA). Spectrapor® dialysis membrane tubing with molecular weight cut off (MWCO) 6000-8000 dalton, Thermo bio-basic SEC-1000 columns, Tosoh TSK G5000PWx1 SEC columns, and all chemicals and reagents were from Sigma, or Aldrich Co., unless indicated.

Purification of Reishi Extract

Crude Reishi powder (6 g) (obtained from Pharmanex Co.) was dissolved in 120 mL of ddH$_2$O, stirred at boiling water (100° C.) for 2 h, and centrifuged (1000 rpm) for 1 h to remove insoluble material. The resulting solution was concentrated at between about 40° C. and about 50° C. to give a small volume, and then lyophilized to generate 5 g (83%) powder of dark-brown color (*G. lucidum* polysaccharides; GLPS). This water soluble residue was stored at −20° C. until further purification.

Standardization-Isolation of the F3 Fraction of Reishi Polysaccharide

*G. lucidum* polysaccharide fraction 3 (hereinafter referred to as "GLPS F3" and "F3") was isolated from the dark powder of water soluble residue of Reishi polysaccharide. All chromatography steps were performed at 4° C. in a cold room. The sample (2.1 g) was dissolved in a small volume of Tris buffer (pH 7.0, 0.1 N) containing 0.1 N sodium azide, and purified by gel filtration chromatography using a Sephacryl S-500 column (95×2.6 cm) with 0.1 N Tris buffer (pH 7.0) as the eluent. The flow rate was set at 0.6 mL/min, and 6.0 mL per tube was collected. After chromatography, each fraction was subjected to the phenol-H$_2$SO$_4$ method to detect the content of sugar in each tube. Five fractions were collected (fraction 1-5). Fraction 3 (F3) was concentrated at about 40~50° C. in a rotary vaporizer to give a small volume which was then dialyzed using a 6000-8000 dalton MWCO membrane to remove excessive salt and sodium azide. Following dialysis, F3 was then lyophilized to give 520 mg of solid.

Preparation of Polysaccharides from *Cordyceps sinensis*

To purify the polysaccharides from *Cordyceps sinensis*, samples were chopped into 0.2 cm$^3$ pieces then incubated in deionized boiling water (100° C.) for 60 min, then cooled down to room temperature before passing through the 0.2 μm filter, followed by addition of an equal volume of ethanol to precipitate the polysaccharides. The precipitates were dried using a lyophilizer and stored at 4° C. Total sugar analysis of the polysaccharides was determined by the Phenol-$H_2SO_4$ method, by measuring OD at 485 nm, while the purity of the polysaccharides was determined by HPLC using a Thermo Bio-Basic SEC-1000 column with UV detection at 280 nm and using a RI detector.

Preparation of Polysaccharides from *Dendrobium huoshanense*

Air-dried *D. huoshanense* was crushed and ground to a powder, homogenized in distilled water, and stirred at 4° C. overnight. The insoluble material was collected by centrifugation. The supernatant was concentrated to a small volume, and then added to 1 volume of ethanol to yield a precipitate (O) and supernatant (N). A TSK G-5000 PW size exclusion column was used in high performance liquid chromatography (HPLC) for polysaccharides analysis with standard pullulan fractions having defined molecular weights. The molecular weight of polysaccharides in N was estimated as between $1.2 \times 10^5$-$4.1 \times 10^5$ daltons, and the molecular weight of polysaccharides in O was estimated as between $1.0 \times 10^6$-$2.2 \times 10^5$ daltons. The total carbohydrate content was measured by the phenol-sulfuric acid method. Polysaccharides in O were 83%, and polysaccharides in N were 77%. Both O and N test positive with an iodine reaction ($\lambda$max 440 nm, deep blue color) suggesting that the polysaccharides in these fractions are primarily α-D-glucan.

Preparation of Polysaccharides from Mushroom

Air-dried *Lentinus edodes* was crushed and ground to a powder, homogenized in distilled water, and stirred at 4° C. overnight. Residues were removed by centrifugation and supernatant was concentrated to a small volume, then lyophilized to give crude polysaccharide L. Then, 0.25N NaOH solution was added to the water insoluble residue (which was isolated by centrifugation), and the mixture was then stirred at room temperature overnight before adding 2 volume of ethanol to precipitate the polysaccharides. Distilled water was then added to the precipitated polysaccharide, followed by acetic acid to neutralize pH. The resulting solution was centrifuged and lyophilized to give polysaccharide M. HPLC using a TSK G-5000 PW size exclusion column was then performed in order to analyze the polysaccharides. The total carbohydrates content was measured by the phenol-sulfuric acid method with L comprising 79% carbohydrates, and M comprising 90% carbohydrates. A comparison with data of the fractions of polysaccharides from *Lentinus edodes* suggested that the polysaccharides L and M are primarily β-1,3-D-glucan.

Preparation of β-1,3-Glucan, D-Glucose and D-Galactose

To prepare samples for a competition assay, 100 mg of β-1,3-glucan (Fluka, Japan) was suspended in 7.5 ml of water, and 50 μl of a 40% (w/w) aqueous solution of sodium hydroxide was added. The mixture was heated under reflux for 1.5 hours, and cooled. Then, methanol was added to precipitate β-1,3-glucan. The β-1,3-glucan precipitate was dissolved in water, dialyzed with 4 L dd-H2O four times, and concentrated at reduced pressure to obtain the water-soluble β-1,3-glucan. D-Glucose (Sigma) and D-galactose (Sigma) were dissolved in dd-H2O (100 mg/ml) and stored at 4° C.

Preparation of Biotinyl-F3

Reishi polysaccharides-F3 were labeled with biotin using a "one pot" reaction. Specifically, Reishi polysaccharide-F3 (100 mg) in 0.2 N $NaHCO_3$/$Na_2CO_3$ (10 mL) was reacted with biotinamidohexanoyl-6-amino-hexanoic acid N-hydroxy-succinimide ester (biotin-XX-NHS) 1.0 mg in DMF (1 mL). The mixture was stirred at room temperature for 12 h. After completion of the reaction, the resulting solution was dialyzed using membrane tubing with a MWCO of 6000-8000 dalton (5×500 mL) at 4° C. for 48 h. After dialysis, the biotinyl-F3 was lyophilized to give a brown powder 90 mg (90%). The purification of biotinyl-F3 was monitored by HPLC and streptavidin-FITC was used for the binding assay.

Example 3

Western Blot Analysis of Purified Receptor.Fc Fusion Proteins

The purified receptor.Fc fusion proteins of Example 1 were subjected to electrophoresis, transferred onto nitrocellulose membrane (Hybond-C extra, Amersham Pharmacia Biotech) and reacted with (1:3000) peroxidase-conjugated goat anti-human IgG Ab (Jackson, Pa., USA) in TBST (5% non-fat dry milk in Tris-buffered saline with 0.02% Tween 20) buffer. After washing with TBST, blots were then incubated with enhanced chemiluminescence reagents (Amersham Pharmacia Biotech) for visualization.

Example 4

Immunosorbent Dot Binding Assay

Biotinylated F3 was blotted onto methanol-activated PVDF membranes (2 μL/dot) after 5-fold serial dilution, using a Bio-Dot Microfiltration Apparatus™ (Bio-Rad, CA, USA). After drying in air, the blot was incubated in TBST, followed by incubation with 100 μL streptavidin-conjugated horseradish peroxidase (HRP) (1:2000 dilution) (Chemicon, CA, USA). Binding reactions were visualized with enhanced chemiluminescence (ECL) reagents (Amersham Pharmacia Biotech).

Non-biotinylated polysaccharides were also immobilized onto methanol-activated PVDF membranes, followed by incubation with 100 μL receptor.Fc fusion protein (1 μg/ml, in 2 mM $CaCl_2$/TBST) on a Bio-Dot Microfiltration Apparatus™ (Bio-Rad, CA, USA) for 1 h at room temperature, then followed by reaction with (1:3000) HRP-conjugated goat anti-human IgG antibody (Jackson, Pa., USA) in TBST (5% non-fat dry milk in Tris-buffered saline with 0.02% Tween 20) buffer. After washing with TBST, the blot was incubated with enhanced chemiluminescence reagents (Amersham Pharmacia Biotech) for visualization.

Example 5

Expression of Recombinant Receptor.Fc Fusion Protein

Figure 1B:
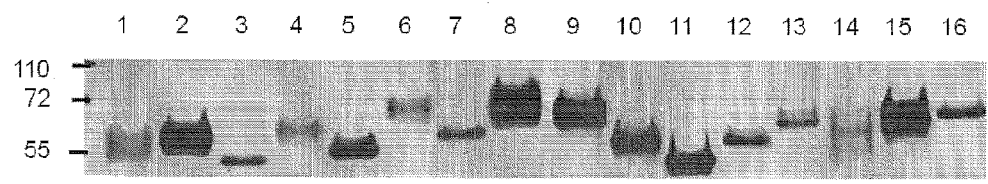
FIG. 1B shows the expressed recombinant receptor.Fc fusion proteins following electrophoresis on a 12% SDS-PAGE gel.

The extracellular domains of several innate immunity receptors from immune cells were cloned by reverse-transcription polymerase chain reaction (RT-PCR) according to the method of Example 1. The amplified DNA fragments were fused with the Fc portion of human IgG1 contained in the pcDNA3/hIgG1-mutant plasmid. The cloned fusion genes was transfected into 293 FREESTYLE mammalian cells, and the secreted proteins were purified by protein beads according to the method of Example 1. As shown in FIG. 1, sixteen C-type lectin genes were cloned (FIG. 1A). Specifically, FIG. 1A shows DNA fragments of innate immunity receptors amplified by RT-PCR, then fractionated on 0.8% agarose and visualized by ethidium bromide staining. FIG. 1B shows the expressed recombinant receptor.Fc fusion proteins following electrophoresis on a 12% SDS-PAGE gel. In both FIG. 1A and FIG. 1B, the following lane designations are used: Lane 1: CLEC2B/AICL, Lane 2: CLEC4C/BDCA-2, Lane 3: CLEC13A/BIMLEC, Lane 4: CLEC1A/CLEC-1, Lane 5: CLEC4D/CLEC-6, Lane 6: CLEC12A/CLL-1, Lane 7: CLEC4A/DCIR, Lane 8: CLEC4L/DC-SIGN, Lane 9: CLEC4M/DC-SIGNR, Lane 10: CLEC7A/Detin-1, Lane 11: CLEC6A/Detin-2, Lane 12:CLEC4H2/HBVxAgBP, Lane 13: CLEC4K/Langerin, Lane 14: KLRG/MAFAL, Lane 15: CLEC5A/MDL-1, Lane 16: CLEC4E/MINCLE. In addition, the human TREM (triggering receptor expressed on myeloid cells)-1, -2 and TREM-like transcripts (TLT)-1, -2 (Bouchon et al., 2000, J Immunol 164, 4991-5; Daws et al., 2003, J Immunol 171, 594-9; Washington et al., 2002, Blood 100, 3822-4) were also cloned and expressed by similar strategy.

Example 6

Dose-Dependent Interaction Between Immobilized Polysaccharides with Receptor.Fc Fusion Proteins The interaction between polysaccharides and the receptor.Fc fusion proteins was tested using a dot-binding assay according to the method of Example 4. The water soluble fraction 3 of Reishi polysaccharides (F3) (see Example 3) contains the active components to stimulate cell producing cytokines (Wang et al., 2002, Bioorg Med Chem 10, 1057-62; Chen et al., 2004, Bioorg Med Chem 12, 5595-601; Chien et al., 2004, Bioorg Med Chem 12, 5603-9; Hsu et al., 2004, J Immunol 173, 5989-99). Reichi saccharide was known to contain either a polysaccharide backbone with β-1,3-linkages, or a polymannose backbone with α-1,4-linkage (Usui et al., 1983, Carbohydr. Res., 273; Miyazaki and Nishijime, 1982, Carbohydr. Res. 109, 290; Bao et al., 2002, Phytochemistry 59, 175-81). The Dectin-1 receptor, a member of the C-type lectin family, has been shown to interact with β-1,3-D-glycans (Brown and Gordon, 2001, Nature 413, 36-7). Dectin-1 receptor has been shown to mediate the biological effects of beta-glucans (Brown et al., 2003, J Exp Med 197, 1119-24). Thus the F3 portion of Reishi was tested to determine whether it could interact with the Dectin-1 receptor using the dot-binding assay of Example 4.

Figure 2A:
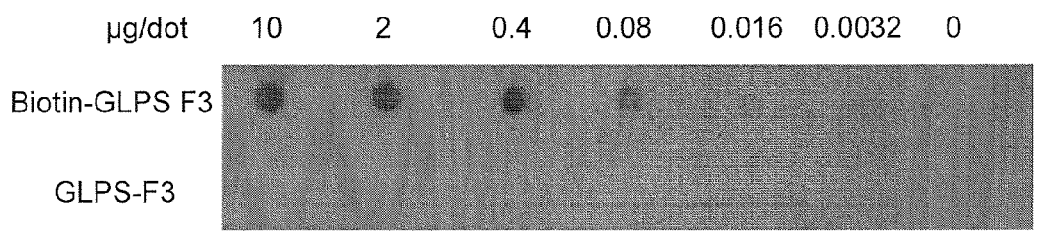
FIG. 2A shows a dot blot of membrane-immobilized biotinylated GLPS F3 contacted with streptavidin-conjugated horseradish peroxidase (HRP).

Biotinylated F3 fraction ("Biotin-GLPS F3" in FIG. 2A) (prepared according to Example 2) was immobilized on a PVDF membrane after a 5-fold serial dilution and incubated with streptavidin-conjugated HRP, and the resulting binding reaction was detected using enhanced chemiluminescence reagents (see Example 4). As shown in FIG. 2A, the sensitivity of this dot binding assay is better than about 0.08 μg. FIG. 2A also shows that no background is seen when unbiotinylated F3 ("GLPS-F3" in FIG. 2A) is immobilized on the PVDF membrane and then contacted with streptavidin-conjugated HRP.

Figure 2B:
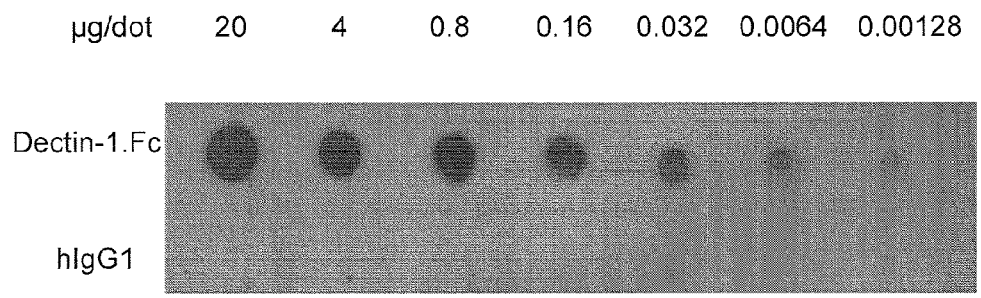
FIG. 2B shows a dot blot of membrane-immobilized non-biotinylated GLPS F3 contacted with a Dectin-1.Fc fusion protein, followed by incubation with goat HRP-conjugated anti IgG1 antibody.

Un-biotinylated F3 fraction was also immobilized on a PVDF membrane after serial dilution, and incubated with 100 μL of 1 g/mL Dectin-1.Fc fusion protein or human IgG1 (as a negative control), followed by incubation with goat HRP-conjugated anti-human IgG (see Example 4). As shown in FIG. 2B, Dectin-1 Fc can detect the presence of less than about 1 ng of F3 in the dot-binding assay. There is no visible background on the regions of the blot contacted with human IgG1 instead of Dectin-1.Fc.

Figure 2C:
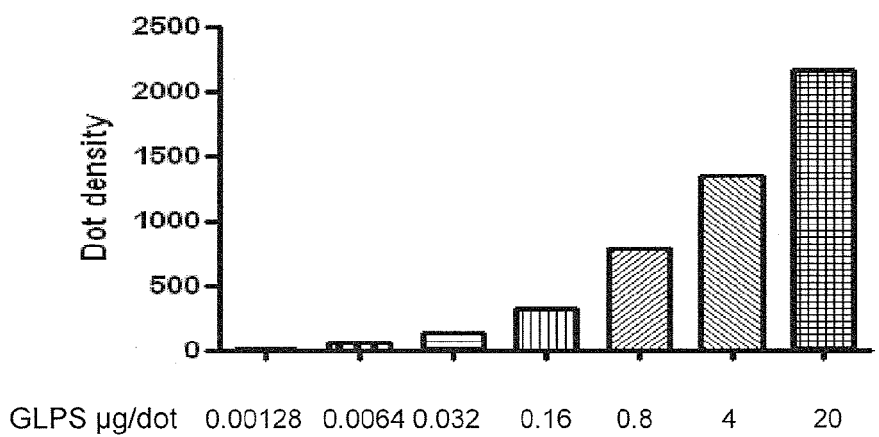
FIG. 2C shows a dot density analysis of the blot of FIG. 2B.

The dot density of the blot of FIG. 2B was determined by a densitometer (ImageQuant), and the results show that the Dectin-1.Fc binding signal increased in a dose-dependent manner (see FIG. 2C).

Figure 2D:
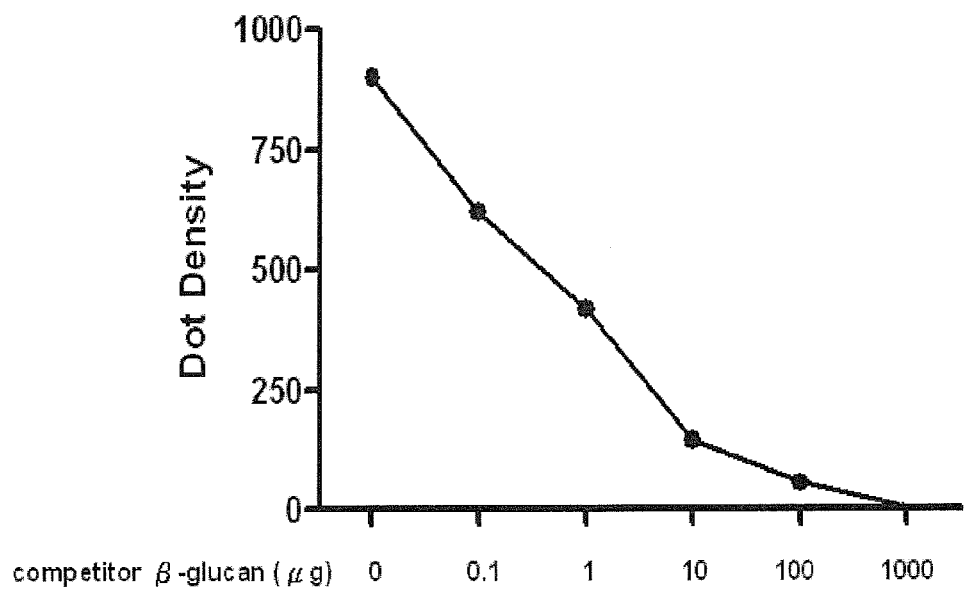
FIG. 2D shows the effects on dot density of competitor β-glucan on the binding of Dectin-1.Fc to membrane-immobilized GLPS F3.
Figure 2E:
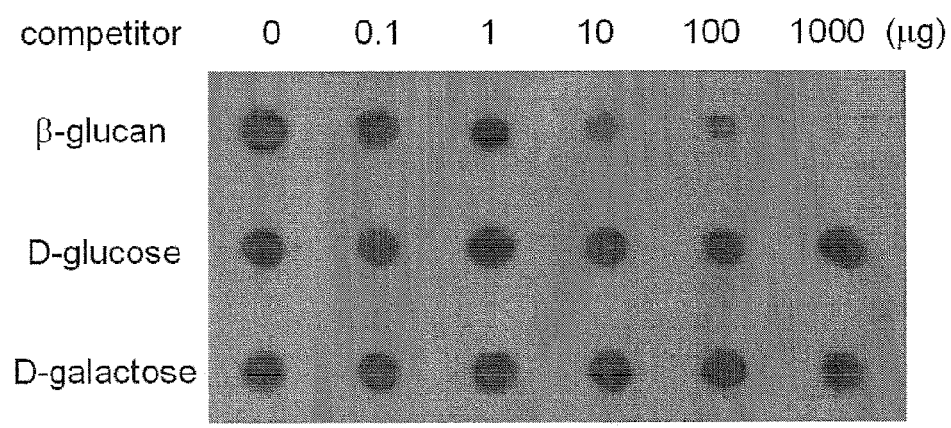
FIG. 2E shows a dot blot of immobilized GLPS F3 contacted with Dectin-1.Fc fusion protein followed by incubation with goat HRP-conjugated anti IgG1 antibody in the presence varying amounts of competitor polysaccharides (β-glucan, D-glucose, and D-galactose).

In order to determine whether other polysaccharides inhibit the interaction between F3 and Dectin-1, F3 (10 μg/dot) was immobilized on PVDF membrane and then contacted with 100 μL Dectin-1.Fc (1 μg/mL) in the presence of serially diluted solutions of β-glucan, D-glucose, and D-galactose (0.1 μg-1000 μg), followed by incubation with goat HRP-conjugated anti-human IgG. FIG. 2D shows dot density analysis of the blot for competitor β-glucan, and FIG. 2E shows a blot image for all the competitors. It can be seen that the interaction between Dectin-1.Fc and the F3 fraction is inhibited by β-1,3-glucan, but not by D-glucose or D-galactose. This indicates the interaction between Dectin-1.Fc with F3 is via recognition of β-1,3-glucan.

Example 7

Identification of Receptors Capable of Interacting with F3 Fraction

Figure 4A:
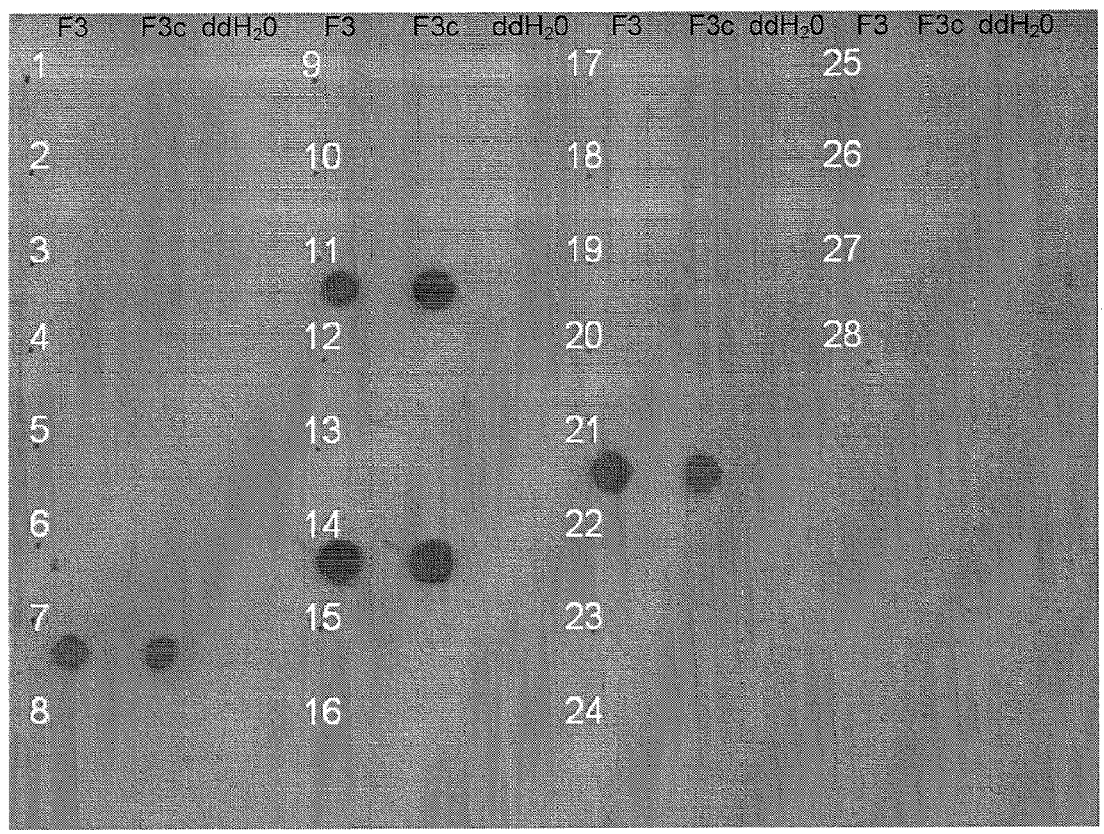
FIG. 4A shows a dot blot of membrane-immobilized GLPS F3 and GLPS F3C probed with the 27 fusion proteins listed in FIG. 3.

The interaction of F3 with other members of the C-type lectin family or with Ig-like receptors was assayed. Non-biotinylated F3 and non-biotinylated F3C (which is derived from F3 after passing through 100 kDa MWCO centrifugal tube) (10 μg/dot) was immobilized on PVDF membrane (see Example 4), then incubated with 100 μL of 1 μg/mL solutions of 25 different recombinant receptor.Fc fusion proteins (including 19 lectin receptors, and 8 members of TREM and TLT families) and human IgG1 as control. Binding was detected using goat HRP-conjugated anti-IgG antibody and ECL reagents. The results are depicted in table form in FIG. 3 (with relative dot intensities indicated by "+" symbols, and no detectable binding indicated by "−" symbol) and an image of the blot is depicted in FIG. 4A. The probe numbering system used in FIG. 3 is retained in FIG. 4A.

The results show that in addition to Dectin-1.Fc (probe no. 14 in FIG. 3 and FIG. 4A), F3 also interacted with KCR.Fc (probe no. 7 in FIG. 3 and FIG. 4A), DC-SIGNR.Fc (probe no. 11 in FIG. 3 and FIG. 4A), and TLT-2.Fc (probe no. 21 in FIG. 3 and FIG. 4A). It is interesting to note that F3C, which is derived from F3 after passing through 100 kDa MWCO centrifugal tube, has less binding affinity to TLT2. This suggests that TLT2 can differentiate the subtle difference between F3 and F3c.

Figure 4B:
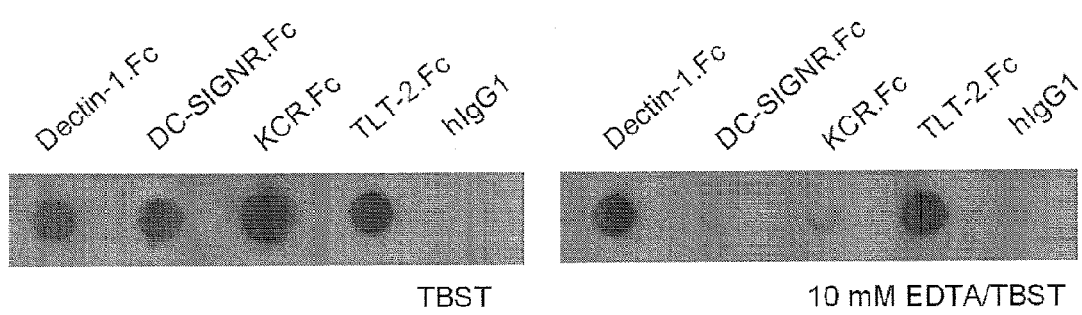
FIG. 4B shows the effect of EDTA on the binding of Dectin-1.Fc, DC-SIGNR.Fc, KCR.Fc, and TLT-2.Fc to membrane immobilized GLPS F3.

Members of the lectin receptor family rely on Ca++ for interaction; therefore, the ability of EDTA (Ethylene Diamine Tetra Acetic Acid) to inhibit binding to F3 was studied. It was found that EDTA (10 mM in TBST) completely abolished the interaction of F3 with KCR.Fc and with DC-SIGNR.Fc, but not the interaction of F3 with Dectin-1.Fc and TLT2.Fc. FIG. 4B depicts images of the blots made in the presence and absence of Ca++ (left panel is TBST only; right panel is 10 mM EDTA+TBST). Binding was detected using goat HRP-conjugated anti-IgG antibody and ECL reagents. This result agrees with previous observations that the interaction between ligands and KCR (Hoyle and Hill, 1988, J Biol Chem 263, 7487-92) and DC-SIGNR is Ca++-dependent (Soilleux et al., 2000, J Immunol 165, 293742), while Ca++ is dispensable for the interaction between Dectin-1 and β-1,3-glucan (Herre et al., 2004, Mol Immunol 40, 869-76). Thus, F3 apparently contains abundant glycans which can interact with multiple receptors on immune cells simultaneously.

Figure 4C:
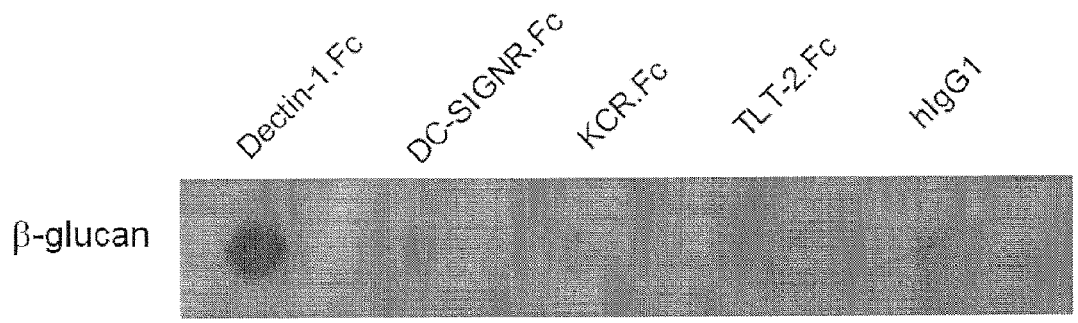
FIG. 4C shows a dot blot of membrane-immobilized β-glucan probed with Dectin-1.Fc, DC-SIGNR.Fc, KCR.Fc, and TLT-2.Fc fusion proteins.

FIG. 4C depicts a dot blot using β-glucan as polysaccharide (10 μg/dot) and using 100 μL of 1 μg/mL Dectin-1.Fc, DC-SIGN.Fc, mKCR.Fc, and TLT2.Fc. Binding was detected using goat HRP-conjugated anti-IgG antibody and ECL reagents. Of the four receptor.Fc fusion proteins tested, only Dectin-1.Fc can bind to β-1,3-glucan. This indicates that the other three receptor.Fc fusion proteins bind to sugar components other than β-1,3-glucan.

Example 8

Fingerprints of Polysaccharides from Various Sources

Figures 5A, 5B:
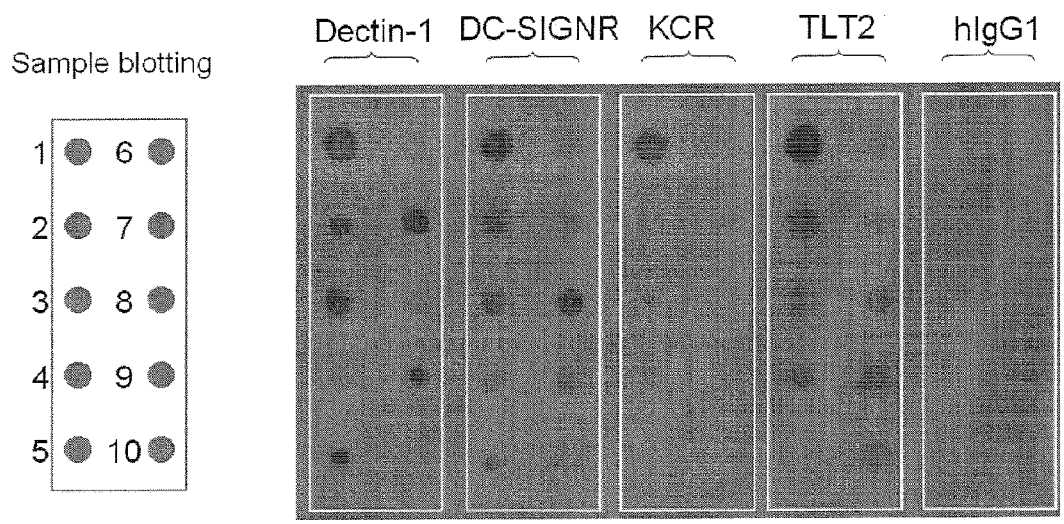
FIG. 5A shows dot blots of polysaccharide samples probed with Dectin-1.Fc, DC-SIGNR.Fc, KCR.Fc, and TLT-2.Fc fusion proteins.
FIG. 5B shows the identity of the sample numbers and provides the dot densities of FIG. 5A in semi-quantitative form.

The dot-binding assay of Example 4 was performed using Dectin1.Fc, mKCR.Fc, DC-SIGNR.Fc, and TLT2.Fc fusion proteins in order to obtain the fingerprints of polysaccharides isolated from *Cordyceps* and other resources on market. Each polysaccharide composition was immobilized on a PVDF membrane as described above and then contacted with 100 μL of a 1 μg/mL solution of the fusion protein. Binding was detected using goat HRP-conjugated anti-IgG antibody and ECL reagents. FIG. 5A shows the individual dot blots for each fusion protein and FIG. 5B shows the sample key numbers and the relative dot intensities in table form. The Reishi crude extract (spot no. 5 in FIG. 5) only interacts with Dectin-1.Fc and DC-SIGNR.Fc, while the purified F3 (spot no. 1) from the crude extract interacts with all the four receptors. This indicates that the F3 purification process enriches the components that interact with immune receptors. Polysaccharide from *Cordyceps* (spot no. 7) interacts strongly with Dectin-1.Fc, indicating that the polysaccharide contains β 1,3 glycan, but its interaction with the other three receptors is much weaker than that of F3. Polysaccharides isolated from *Dendrobium huoshanense* test positive with the iodine test reaction (see Example 2) suggesting these fractions comprise mainly α-D-glucan. In contrast to those isolated from fungi, the mixture of polysaccharides of *D. huoshanense* (spot no. 6) does not react with any of the four receptor.Fc fusion proteins. Polysaccharides isolated from mushroom polysaccharides by ddH2O (fraction L, spot no. 8) and 0.25N NaOH (fraction M, spot no. 9) (see Example 2) bind differentially to Dectin-1.Fc and DC-SIGNR.Fc. Thus, this approach can produce distinct fingerprints from polysaccharides isolated from different sources and preparations, Examples 6-8 illustrate that F3 interacts with Dectin-1.Fc, mKCR.Fc, DC-SIGNR.Fc, and TLT2.Fc. The Kupffer cell receptor (KCR) has high affinity to D-galactose and N-acetylgalactyosamine (Fadden et al., 2003, Glycobiology 13, 529-37), and is able to clear serum D-galactose- or D-fucose-terminated glycoprotein (Lehrman et al., 1986, J Biol Chem 261, 7426-32), The immunomodulatory function of F3 is dependent on the presence of fucose, and glycolytic cleavage by α1,2-fucosidase abolishes F3 activity. Thus it would be interesting to ask whether these four receptors can interact with F3 after glycolytic cleavage. DC-SIGNR/L-SIGN is structurally similar to DC-SIGN (77% identity), but it is only expressed in the endothelial cells of liver sinusoid, lymph node and placenta (Van Liempt et al., 2004, J Biol Chem 279, 33161-7). Both DC-SIGN and DC-SIGNR can bind to N-linked high-mannose oligosaccharides ($Man_9GlcNAc_2Asn$ glycopeptide). However, only DC-SIGN, and not DC-SIGNR, can bind to glycans with a terminal fucose residue (Guo et al., 2004, Nat Struct Mol Biol 11, 591-8). Even though DC-SIGNR binds relatively restricted ligands than DC-SIGN, only DC-SIGNR can interact with F3. This suggests that F3 might contain a unique structure distinct from Fucα1-4GlcNAc, Lewis$^x$, Lewis$^a$ and blood group sugar epitopes (the known ligands for DC-SIGN).

TLT-2 is a member of TREM-like transcripts family, which contain a characteristic single V-set immunoglobulin (Ig) domain and a long cytoplasmic tail with a proline-rich region and an immune receptor tyrosine-based inhibitory motif (ITIM), the latter known to be used for interactions with protein tyrosine phosphatases (Washington et al., 2002, Blood 100, 3822-4; Washington et al., 2004, Blood 104, 1042-7). Since F3 has potent immunostimulatory functions, it would be interesting to study whether the removal of TLT2.Fc. binding components from F3 by affinity chromatography could further enhance the stimulatory functions of F3 in the future. Alternatively, F3 can be further purified by affinity chromatography using Dectin-1.Fc, KCR.Fc, and DC-SIGNR.Fc to remove other components in F3.

The differential fingerprints between F3 and F3c; between F3 and Reishi 1-3; and between mushroom polysaccharides fraction L and M, suggest that these four receptor.Fc fusion proteins exemplified herein can be used to optimize purification procedures, and to monitor the variation of polysaccharides from different sources or from different fermentation conditions.

Example 9

Figure 6A:
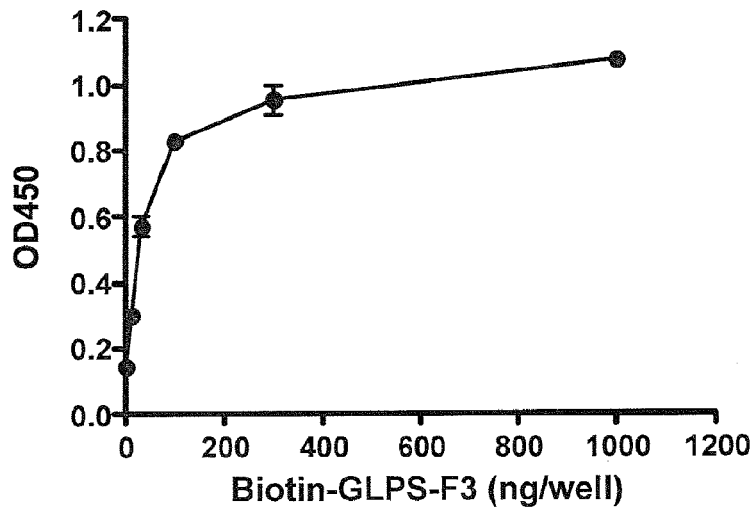
FIG. 6A shows the amount of biotinylated GLPS-F3 coated onto a microtiter plate as measured using a peroxidase-conjugated avidin assay and reading at OD450 nm to detect the yellow-colored reaction product.

Identification of Human Lectin Receptors that Interact with GLPS-F3 by Enzyme Linked Immunoassay on Microtiter Plates The interactions of polysaccharides with receptor.Fc fusion proteins was further investigated by performing an enzyme-linked immunoassay (EIA), which was based on immobilizing GLPS-F3 through both hydrophilic and hydrophobic forces onto microtiter plates (polysytrene). In this format, the number of different receptor.Fc fusions for profiling was increased in comparison to Example 7. To optimize the quantity of GLPS-F3 for immobilization, various amounts (3-1000 ng/well, diluted in 100 mM Tris buffer, pH9.5) of biotinylated-GLPS-F3 (Biotin-GLPS-F3) were coated onto MaxiSorp StarWell microtiter plates (50 μl/well; Nunc). The plates were incubated overnight at 4° C., and then the wells were washed twice with TBST, followed by blocking with 200 μL blocking buffer (2% BSA/TBST) for 1 hour at room temperature. Peroxidase-conjugated avidin (1:5000 dilution, Vector Laboratories) and TMB (tetramethylbenzidine) substrate was then used for detection of immobilized biotinylated GLPS-F3. As shown in FIG. 6A, the quantity of Biotin-GLPS-F3 for plate coating reached plateau at 100 ng/well, which was therefore chosen to use for immobilizing un-biotinylated GLPS-F3 in EIA.

Figure 6B:
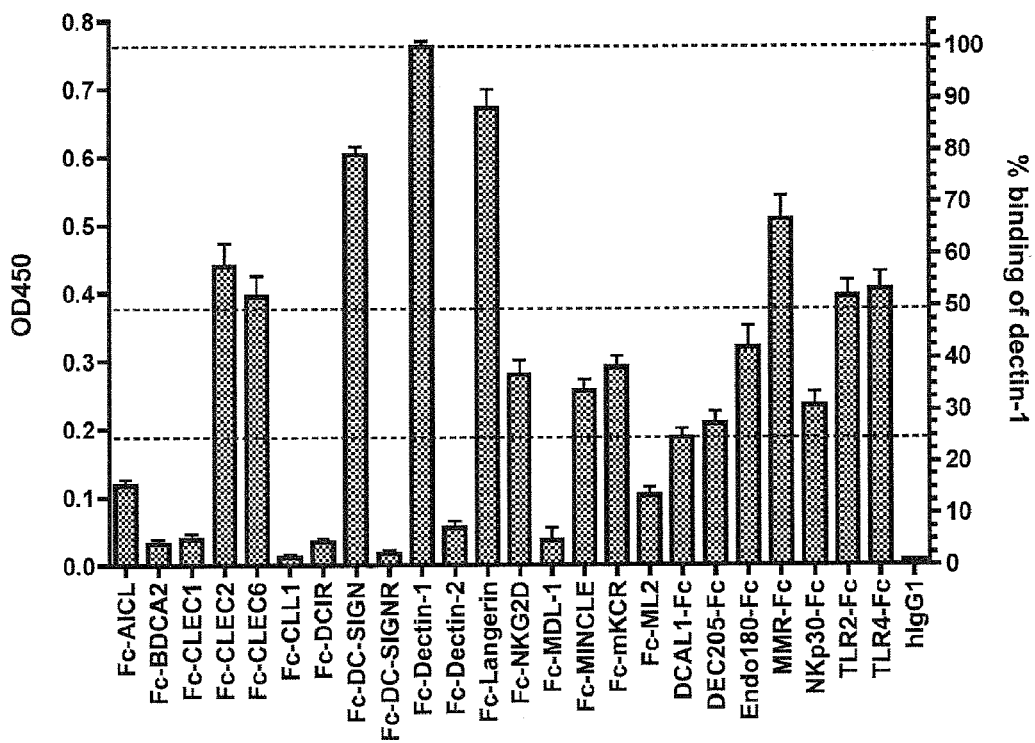
FIG. 6B depicts in graphical form the affinity of various receptor.Fc fusion proteins for GLPS-F3 immobilized on a microtiter plate. The absolute binding of each receptor.Fc fusion protein is depicted on the left Y axis (as an OD450 nm reading) and the right Y axis depicts the relative binding in comparison to the binding of Dectin-1.Fc.

The interaction between GLPS-F3 and receptor.Fc was then tested. Unbiotinylated GLPS-F3 was immobilized at 100 ng/well as described above, and 100 μL receptor.Fc fusion protein (1 μg/ml in 2 mM $MgCl_2$/2 mM $CaCl_2$/1% BSA/TBST) was added into each well and incubated for 1 hour at room temperature. After washing with TBST, wells were incubated with peroxidase-conjugated goat anti-human IgG Ab (1:5000 dilution, Jackson ImmunoResearch Laboratories) in blocking buffer at room temperature for 30 min. Wells were incubated with 100 μL TMB substrate for 15 min after TBST washing and read at 450 nm in a Fusion plate reader (Perkin Elmer). The results were normalized with respect to Fc.Dectin-1 binding (Dectin-1 is a known lectin receptor that binds to β-1,3-glucan which is the backbone found in GLPS-F3). FIG. 6B depicts in graphical form the affinity of each receptor for GLPS-F3 relative to Dectin-1. The results show that high binding affinity to GLPS-F3 was observed for Fc.Langerin, Fc.DC-SIGN, MMR.Fc, TLR2.Fc, TLR4.Fc, Fc.CLEC-2 (CLEC1B) and Fc.CLEC-6 (CLEC4D) (high binding was defined in this assay as >50% binding intensity compared to Fc.Dectin-1). It is noteworthy that TLR2 and TLR4, which have been demonstrated to play a role in GLPS-induced cell activation (Hsu et al., J Immunol 173:5989-5999 (2004); Shao et al., Biochem Biophys Res Commun 323:133-141 (2004)), bound to GLPS-F3 in the EIA format as well. There was also weaker but positive GLPS-F3 binding ability (25-50% binding intensity compared to Fc.dectin-1) found in Fc.NKG2D, Fc.MINCLE, Fc.mKCR, DCAL1.Fc, DEC205.Fc, Endo180.Fc and NKp30 (NCR3).Fc. Other lectin receptors including Fc.AICL, Fc.BDCA2, Fc.CLEC1, Fc.CLL1, Fc.DCIR, Fc.DC-SIGNR, Fc.dectin-2, Fc.MDL-1 and Fc.ML2 had minimal binding ability to GLPS-F3, as did control human IgG1.

Example 10

Competition Assay for GLPS-F3-Interacting Innate Immunity Receptors

To understand the interaction of GLPS-F3 with specific innate immunity receptors, the polysaccharides mannan and β-glucan and the monosaccharides D-mannose (Man), D-glucose (Glc), N-acetyl-glucosamine (GlcNAc), D-galactose (Gal), N-acetyl-galactosamine (GalNAc), L-fucose (Fuc) and sialic acid, were used in a competition assay. Innate immunity receptors that showed higher binding ability to GLPS-F3 were examined, including Fc.Dectin-1, Fc.Langerin, Fc.DC-SIGN, TLR4.Fc, MMR.Fc, Fc.CLEC-2 (CLEC1B) and Fc.CLEC-6 (CLEC4D). The assays were carried out as in Example 9, with the addition of 1 mg/ml of each polysaccharide or monosaccharide.

Figure 7:
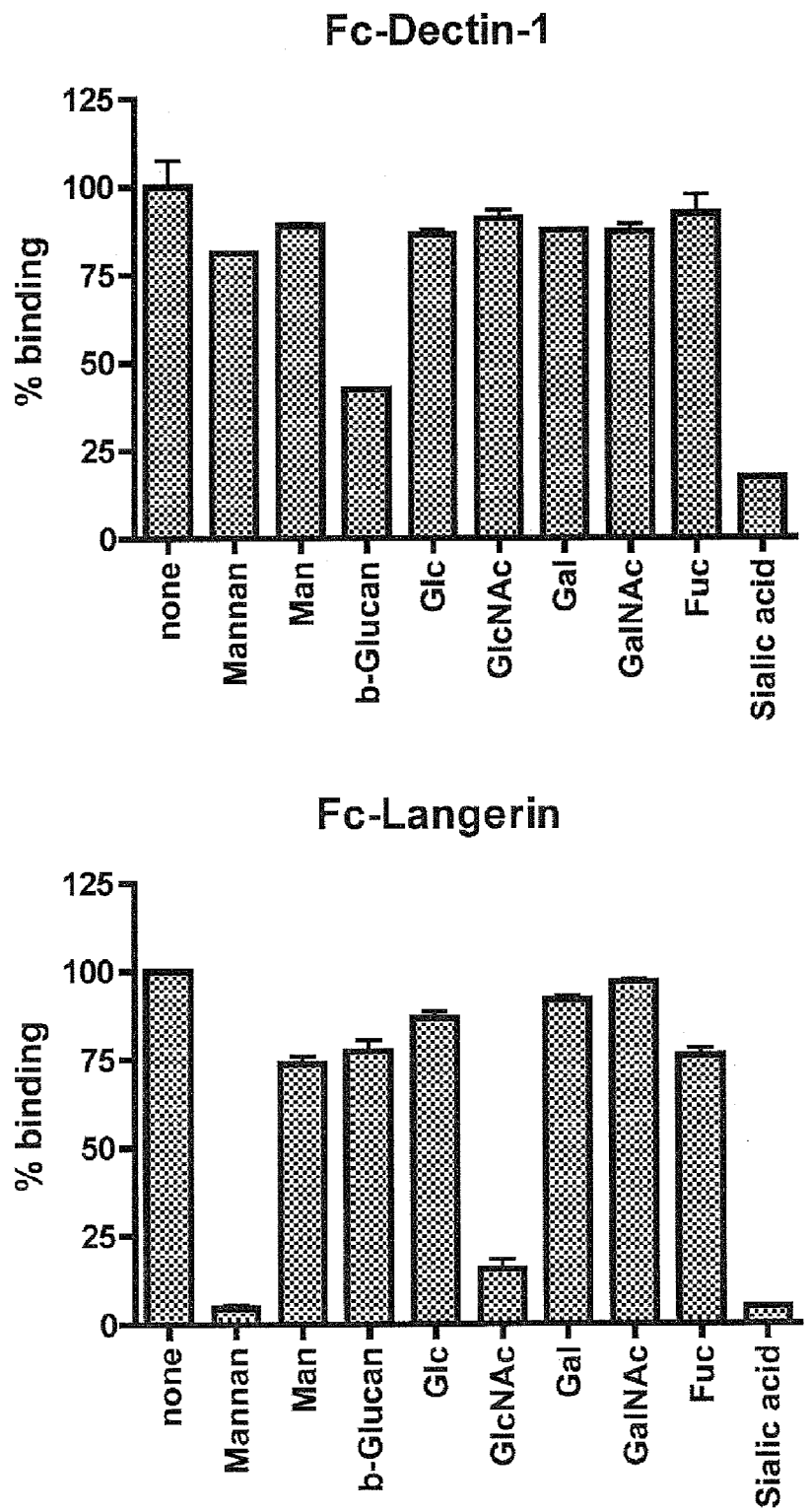
FIG. 7 illustrates graphically the percentage binding of various receptor.Fc fusion proteins to GLPS-F3 in a competition assay with the polysaccharides mannan and β-glucan, and with the monosaccharides D-mannose (Man), D-glucose (Glc), N-acetyl-glucosamine (GlcNAc), D-galactose (Gal), N-acetyl-galactosamine (GalNAc), L-fucose (Fuc) and sialic acid.
Figure 7:
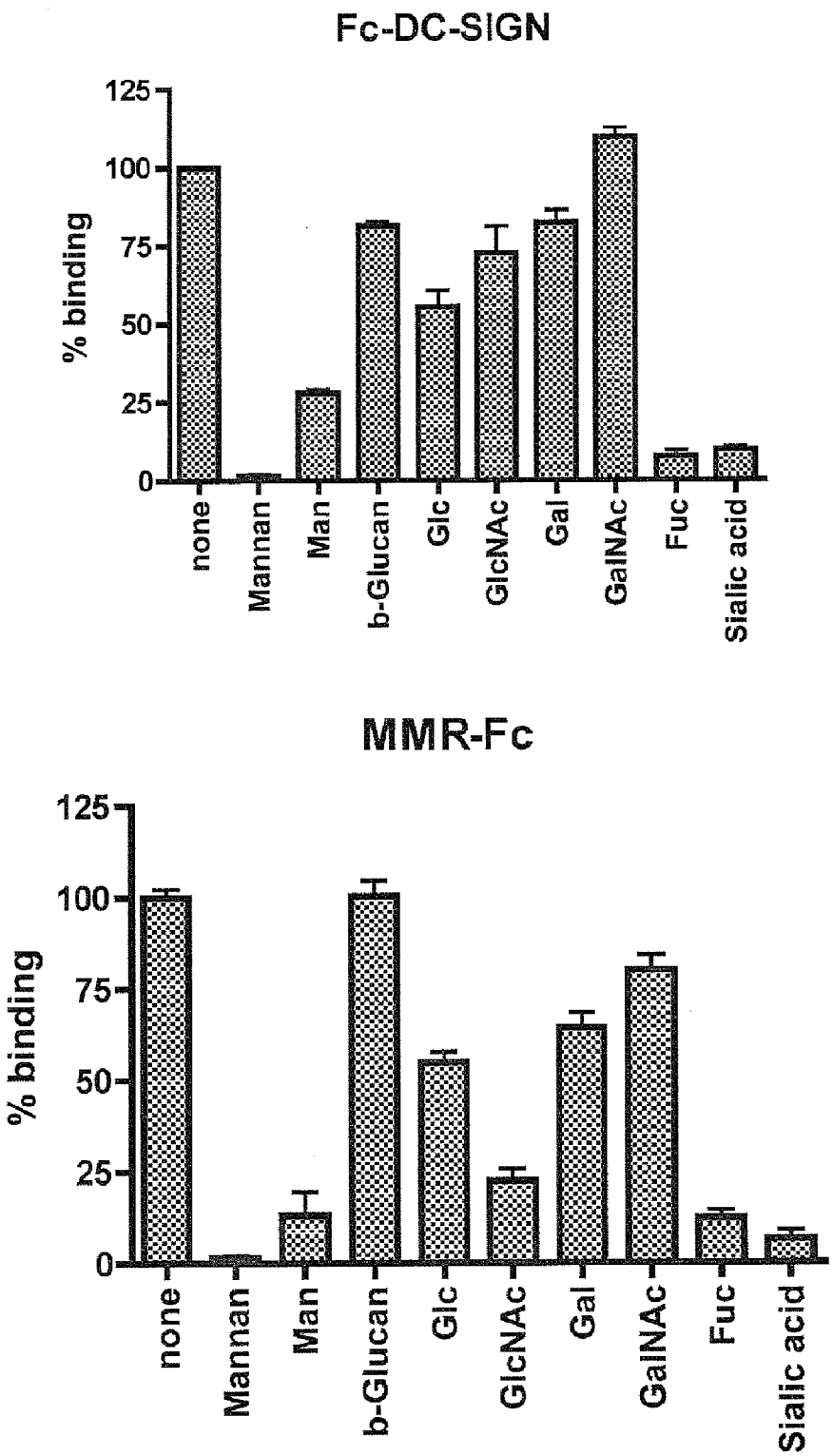
Figure 7:
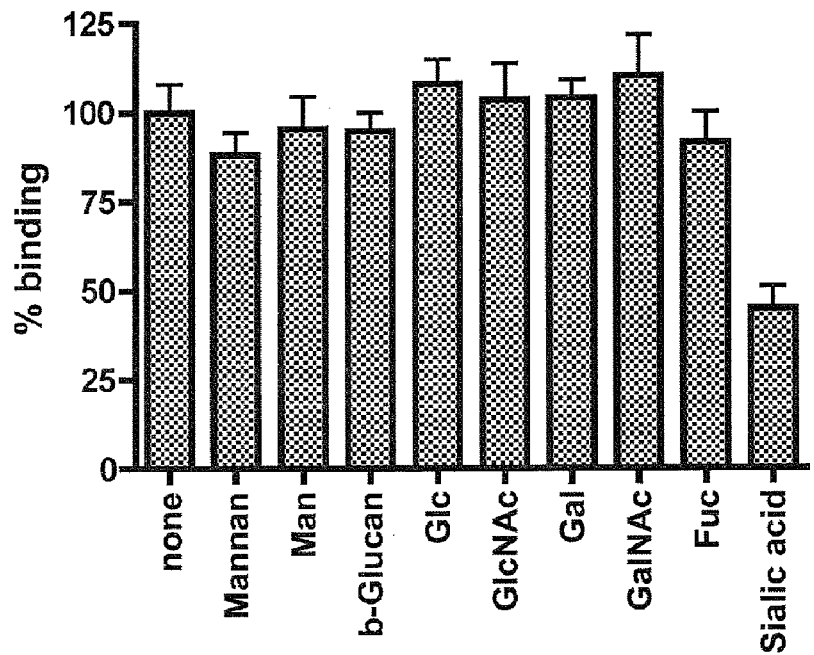
Figure 7:
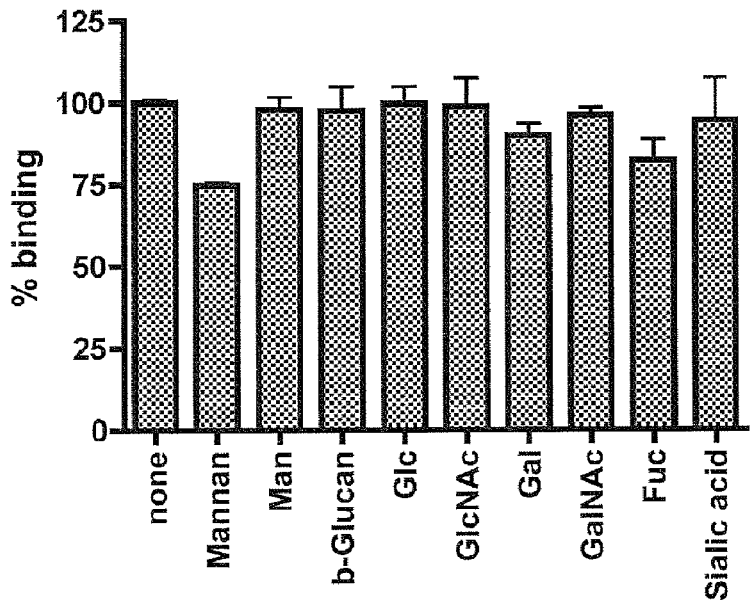
Figure 7:
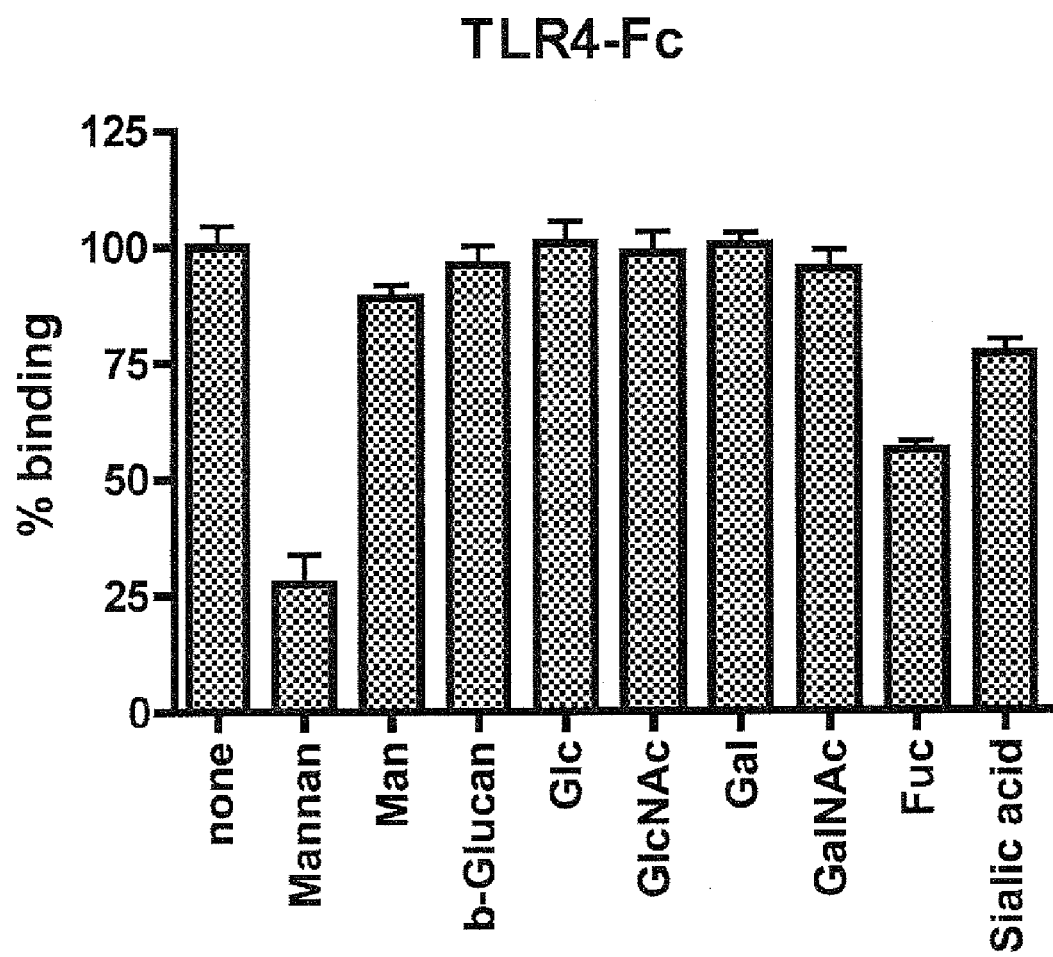

As shown in FIG. 7 (which shows graphically the % binding for each receptor/saccharide combination relative to the binding seen in the absence of saccharide) and Table I (which provides the data from FIG. 7 in tabular form), the interaction between GLPS-F3 and Fc.Dectin-1 could be blocked by β-glucan with 58% inhibition, which is in accordance with published results (Palma et al., J Biol Chem 281:5771-5779 (2006); Willment et al., J Biol Chem 276:43818-43823 (2001)). The addition of sialic acid (83% inhibition) interfered with the binding of Fc.Dectin-1 to GLPS-F3. The interaction between Fc.Langerin and GLPS-F3 was disrupted by mannan, Man and GlcNAc (95%, 26% and 84% inhibition), which are reported as the sugar ligands for Langerin (Stambach & Taylor, Glycobiology 13:401-410 (2002)); sialic acid (95% inhibition) was also observed to interfere with the binding of Fc.Langerin to GLPS-F3. As for the binding of Fc.DC-SIGN to GLPS-F3, mannan, Man, Fuc and sialic acid showed a potent blocking activity (98%, 72%, 92% and 90% inhibition), while Glc and GlcNAc had a weaker effect (45% and 27% inhibition, respectively) in blocking the interaction. Mannan, Man, Glc, GlcNAc, Gal, Fuc and sialic acid blocked the interaction (98%, 87%, 45%, 78%, 36%, 88% and 93% inhibition) between GLPS-F3 and MMR.Fc, an important lectin receptor that is known to bind Man, Fuc, GlcNAc and sialyl Lewis x (sLex) (Letuex et al., J Exp Med 191:1117-1126 (2000); Stahl, Am J Respir Cell Mol Biol 2:317-318 (1990)). The interaction of Fc.CLEC-2 to GLPS-F3 was blocked by the addition of sialic acid (55% inhibition). For Fc.CLEC-6, no obvious blocking was observed among the sugar tested. Notably, mannan and Fuc showed a blocking effect (72% and 44% inhibition, respectively) on TLR4.Fc and GLPS-F3 interaction. The data obtained here was in line with the results reported by the study of sugar ligands for Dectin-1, Langerin, DC-SIGN and MMR. It was also indicated that many lectin receptors could bind to GLPS-F3 with multivalency through different sugar components.

TABLE I

Percentage of binding of innate immunity receptor.

| Sugar | Innate Immunity Receptor | | | | | | |
|---|---|---|---|---|---|---|---|
| | Dectin-1 | Langerin | DC-SIGN | TLR4.Fc | MMR.Fc | CLEC-2 | CLEC-6 |
| none | 100 ± 7.6 | 100 ± 1.0 | 100 ± 0.1 | 100 ± 4.5 | 100 ± 2.2 | 100 ± 8.0 | 100 ± 0.8 |
| mannan | 82 ± 0.2 | 5 ± 0.9 | 2 ± 0.5 | 28 ± 6.3 | 2 ± 0.5 | 88 ± 6.3 | 75 ± 0.8 |
| Man | 89 ± 0.5 | 74 ± 2.1 | 28 ± 1.3 | 89 ± 2.6 | 13 ± 6.4 | 95 ± 9.1 | 98 ± 3.7 |
| b-glucan | 42 ± 0.3 | 77 ± 3.2 | 81 ± 1.4 | 96 ± 4.0 | 100 ± 4.2 | 95 ± 5.1 | 98 ± 7.3 |
| Glc | 86 ± 1.5 | 87 ± 2.0 | 55 ± 5.4 | 101 ± 4.7 | 55 ± 2.9 | 108 ± 6.8 | 100 ± 5.3 |
| GlcNAc | 91 ± 2.6 | 16 ± 2.7 | 73 ± 8.6 | 99 ± 4.7 | 22 ± 3.4 | 103 ± 10.2 | 99 ± 8.5 |
| Gal | 88 ± 0.4 | 92 ± 0.9 | 82 ± 4.0 | 100 ± 2.7 | 64 ± 4.2 | 104 ± 5.1 | 90 ± 3.7 |
| GalNAc | 88 ± 2.6 | 97 ± 0.7 | 110 ± 3.1 | 95 ± 4.1 | 80 ± 4.2 | 110 ± 11.4 | 96 ± 2.4 |
| Fuc | 92 ± 5.2 | 76 ± 1.9 | 8 ± 1.8 | 56 ± 1.9 | 12 ± 2.0 | 91 ± 8.5 | 82 ± 6.5 |
| sialic acid | 17 ± 0.3 | 5 ± 0.3 | 10 ± 1.0 | 77 ± 3.1 | 7 ± 2.4 | 45 ± 6.2 | 94 ± 13.0 |

Fc fusions to GLPS-F3 in the presence of sugar competitors relative to binding seen in absence of sugar competitor.

The systems presented in Examples 7-10 are useful tools for high throughput profiling of not only GLPS, but also other glycoprotein mixtures including many Chinese herb drugs currently in use. By using different surfaces for immobilizing polysaccharides (PVDF and polystyrene), different profiles were obtained for GLPS-F3. This may be due to preferential binding of certain polysaccharides within the mixtures to different surfaces. The results obtained from these two complementary formats provide "fingerprints" of polysaccharide mixtures. These strategies of fingerprinting polysaccharide mixtures can be used, for example, to monitor the contents of herb extracts under different conditions, from different sources, or from different batches. Moreover, the information gathered from the profiles of specific polysaccharide mixtures will be of great importance in understanding the underlying molecular mechanisms of their biological effects in vivo.

Example 11

Detection of the Interaction of DVLR1 (MDL-1) with Dengue Virus

The following examples show how the fusion proteins and methods of the disclosure can be used to identify the innate immunity receptor(s) that interact with a pathogen, and how that information can subsequently be used to determine the downstream effects of pathogen binding to the innate immunity receptor, and also to design therapeutic agents for the treatment of pathogen infection.

Dengue is one of the most important mosquito-borne viral disease affecting humans. Its global distribution is comparable to that of malaria, and an estimated 2.5 billion people live in areas at risk for epidemic transmission. The clinical syndromes after dengue virus (DV) infection include dengue fever (DF) and dengue hemorrhagic fever (DHF)/dengue shock syndrome (DSS). However, the underlying molecular mechanisms leading to DHF and DSS are still not well elucidated.

DC-SIGN is known to mediate DV infection of human dendritic cells (Tassaneetrithep et al., J Exp Med, 2003. 197 (7): p. 823-9). In order to understand the pathogenesis of DV, it is important to determine whether DV can interact with other membrane-bound C-type lectin receptors and C-type-like lectin receptors from dendritic cells, macrophages, natural killer cells, and peripheral blood mononuclear cells (PBMCs). To this end, the extracellular domains of DVLR1 (MDL-1/CLEC5A), Dectin-1, KCR, and DC-SIGN (as a positive control) were fused to the Fc portion of human IgG1. Specifically, primers for DC-SIGN (SEQ ID NO: 17 and SEQ ID NO: 18), DVLR1 (SEQ ID NO: 21 and SEQ ID NO:22), Dectin-1 (SEQ ID NO:25 and SEQ ID NO:26) and KCR (forward: 5'-CAGCCTTGGAGACCTGAGT-3' SEQ ID NO: 37; reverse 5'-TAGCCTACTCTGGCCGC-3' SEQ ID NO:38) were used to generate amplified cDNA fragments. Each forward primer had an extra BamH1 site, and each reverse primer had an extra EcoRI site to facilitate the subcloning of the amplified cDNA into the pcDNA3.1 (Invitrogen) mammalian expression vector containing the human IgG1 Fc portion. The resulting vector was then transfected into 293 FreeStyle cells (Invitrogen) to produce soluble recombinant proteins. All recombinant receptor.Fc fusion proteins were purified by protein A Sepharose beads (Pharmacia) and eluted with 0.1M glycine-HCl (pH0.3).

One µg of each receptor.Fc fusion protein was coated onto microtiter plates overnight at 4° C. DV ($5 \times 10^6$ particles) of strain 16681 (a DEN2 strain) in binding buffer (1% BSA, 2 mM $CaCl_2$, 2 mM $MgCl_2$, 50 mM Tris-HCl pH 7.5, 150 mM NaCl) was then added to the plates and the plates were incubated for 2 hours. After washing non-bound virus, a biotinylated anti-DEN2 envelope protein antibody (Wu et al., J Virol, 2002. 76(8): p. 3596-604) was applied to bind to the virus for 1 hour. Diluted horseradish peroxidase-conjugated streptavidin was then added to the plates, followed by a 1 hour incubation. TMB substrate was then added and the plates were read using an ELISA reader at OD450 nm.

Figure 8A:
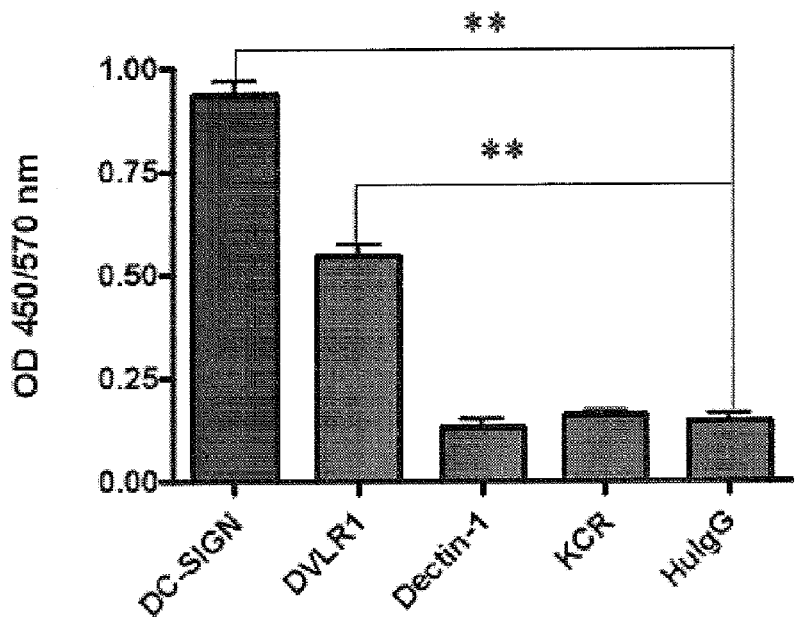
FIG. 8A shows graphically the binding of receptor.Fc fusion proteins to Dengue Virus, in comparison to a human IgG negative control.
Figure 8B:
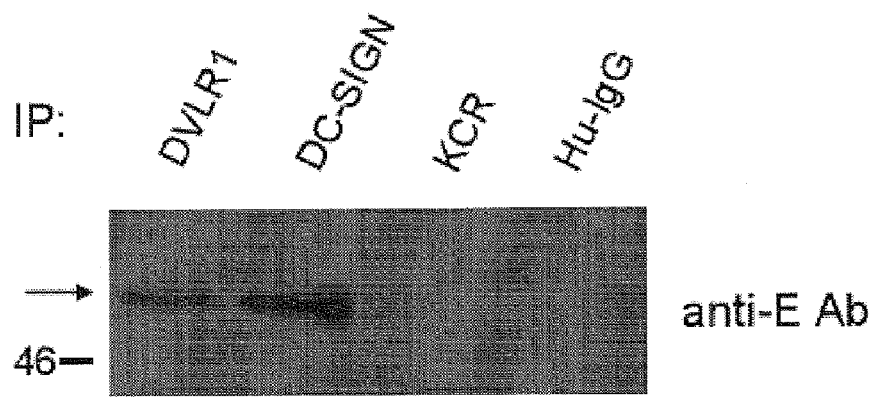
FIG. 8B shows a Western blot of immunocomplexes of Dengue Virus with three receptor.Fc fusion proteins and a human IgG negative control, probed with an antibody against the Dengue Virus E protein.

The results are depicted in FIG. 8A ( indicates p<0.01, * indicates p<0.001 (Student's t test)). The results show that in addition to DC-SIGN (positive control), DV also binds to DVLR1/MDL-1. To confirm this result, immunoprecipitation studies were performed with human IgG1 (negative control), DC-SIGN.Fc, KCR.Fc, and DVLR1.Fc. Specifically, $5 \times 10^6$ Dengue virus particles were incubated with 5 µg of each protein, and then Protein A beads were added. The resulting immunocomplexes were washed, separated by SDS-PAGE, and transferred onto nitrocellulose membrane. The membrane was then probed with biotinylated anti-DEN2 envelope protein antibody and developed with horseradish peroxidase-conjugated streptavidin. The results are shown in FIG. 8B. The results show that only DC-SIGN.Fc and DVLR1.Fc were able to immunoprecipitate DV.

Figure 8C:
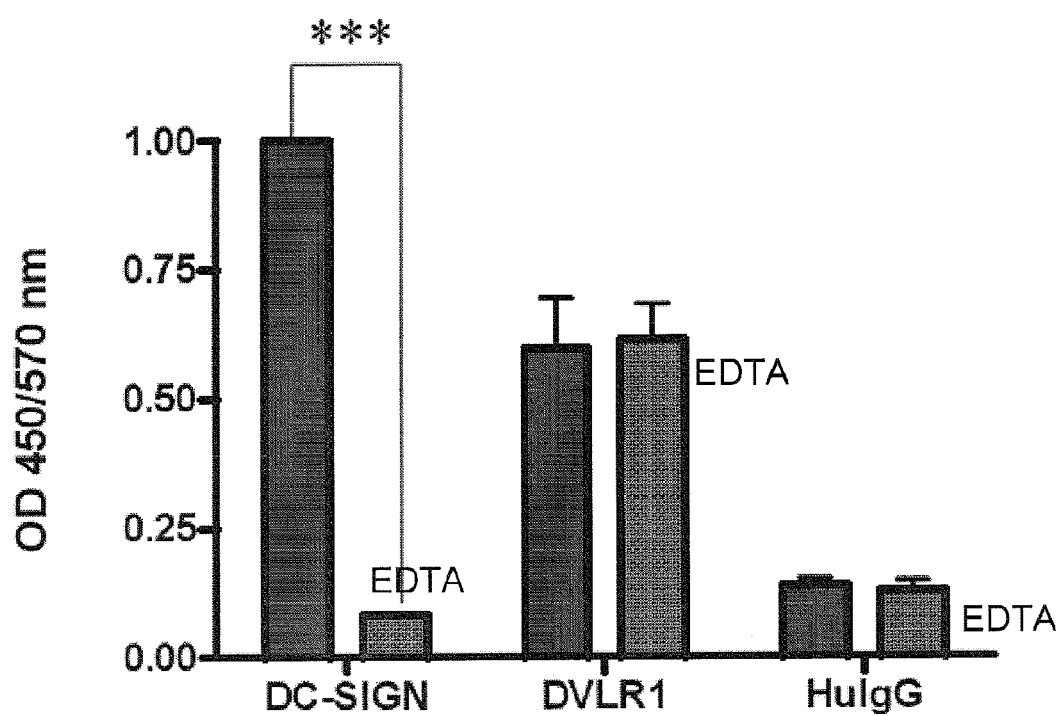
FIG. 8C shows graphically that EDTA inhibits the binding of Dengue Virus to DC-SIGN.Fc fusion protein, but not the binding to DVLR1.Fc fusion protein.

The microtiter plate assay was repeated in the presence of EDTA (10 mM) to chelate $Ca^{2+}$ cations. The results (FIG. 8C) reveal that DVLR1 binding to Dengue virus is $Ca^{2+}$ independent, whereas DC-SIGN binding is $Ca^{2+}$ dependent (*** indicates p<0.001, Student's t test).

Figure 8D:
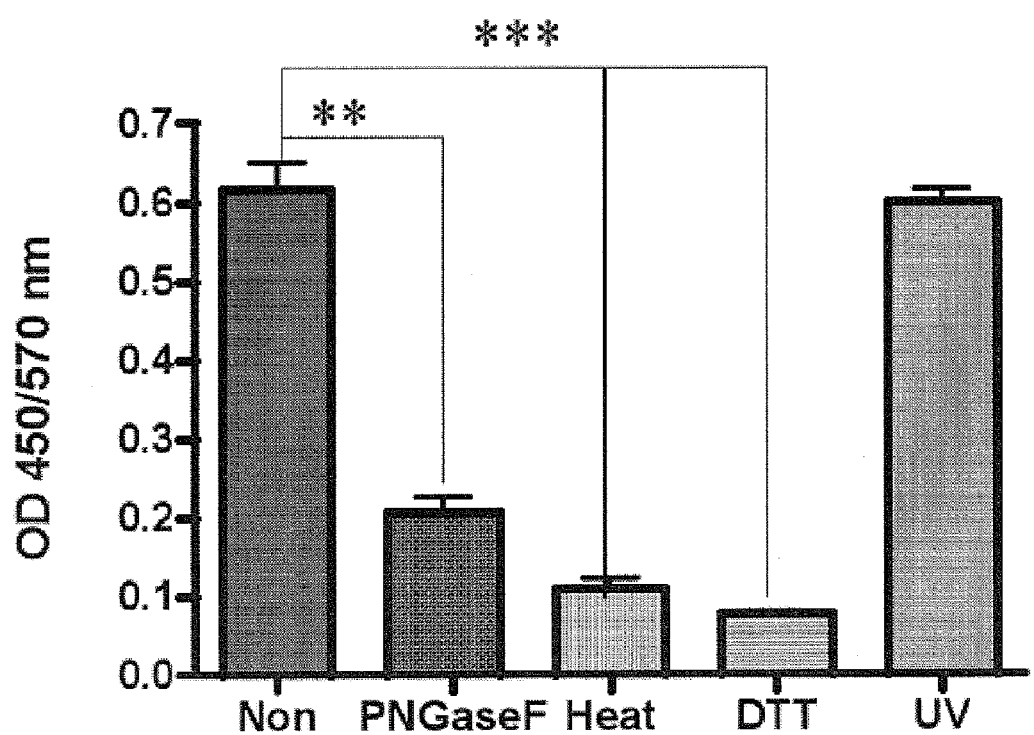
FIG. 8D shows the binding of a DVLR1.Fc fusion protein to Dengue Virus treated with PNGaseF, dithiothreitol (DTT), heat, or UV irradiation, and to untreated Dengue Virus (non).

The microtiter plate assay was also repeated for DVLR1.Fc fusion protein with DV particles ($5 \times 10^6$) that had been 1) preincubated with 500 U of the glycosidase PNGaseF (New England Biolabs, Inc.) overnight at 37° C.; or 2) treated with dithiothreitol (DTT) (0.1M); or 3) incubated at 95° C. for 5 minutes; or 4) UV irradiated for 5 minutes. The results are shown in FIG. 8D (asterisks indicate where the binding affinity of DVLR1.Fc fusion protein is altered by modification of the virus relative to non-treated virus;  p<0.01, * p<0.001, Student's t test). The results indicate that pretreatment of DV with PNGase F inhibited DVLR1.Fc interaction significantly, and that pretreatment with either heat or dithiothreitol almost completely inhibited DVLR1.Fc binding, but not DC-SIGN.Fc binding to DV. This suggests that both the sugar epitope(s) and the three dimensional conformation of DV are important for binding to DVLR1.

In order to evaluate the expression of DVLR1 on immune cells, flow cytometric analysis was performed on human polymorphonuclear (PMN) cells (neutrophils), PBMCs, macrophages, and dendritic cells. PMNs and PBMCs were isolated from the whole blood of human healthy donors by dextran sedimentation as described (Kuan et al., Br. J. Pharmacol., 2005, 145(4):460-468) and standard density gradient centrifugation with Ficoll-Paque respectively (Amersham Biosciences, Piscataway, N.J.). Purified neutrophils were resuspended in phosphate saline buffer (PBS, pH 7.4) with hypotonic lysis of erythrocytes. CD14+ cells were subsequently purified from PBMCs by high-gradient magnetic sorting using the VARIOMACS technique with anti-CD 14 microbeads (Miltenyi Biotec GmbH, Bergisch Gladbach, Germany), then were cultured in complete RPMI-1640 medium (Life Technologies, Gaithersburg, Md.) supplemented with 10 ng/ml human M-CSF (R&D Systems, Minneapolis, Minn.) for 6 days (Chang et al., J. Leukoc Biol, 2004, 75(3):486-494). Dendritic cells (DC) were generated from adherent PBMCs by culture in RPMI 1640 medium supplemented with 10% fetal calf serus, 800 U/ml human GM-CSF (Leucomax; Schering-Plough, Kenilworth, N.J.), and 500 U/ml human IL-4 (R&D Systems) for 6 days (immature DCs). To prepare mature activated DCs, immature DCs were further incubated with gamma-irradiated (5500 rad) CD40 ligand (CD40L)-expressing L cells (DNAX Research Institute, Palo Alto, Calif.) at a ratio of 3:1 for 36 hr (Hsu et al., J. Immunol., 2002, 168(10):4846-4853).

Figure 9A:
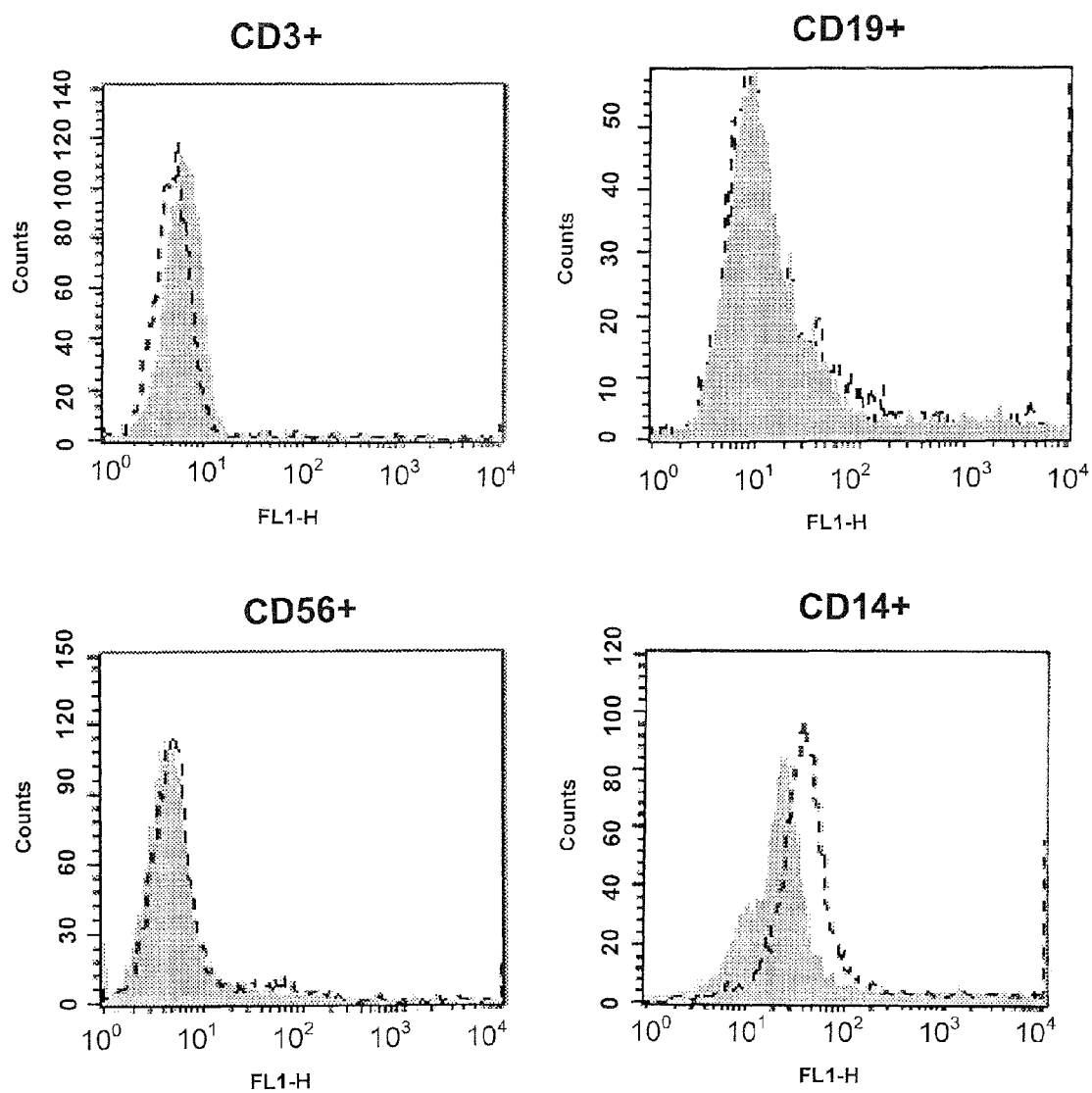
FIG. 9A shows the expression of DVLR1 in various immune cell types by flow cytometry using an anti-DVLR1 antibody. Expression of DVLR1 is indicated where the DVLR1 profile (dotted line trace) does not match the antibody isotype control (shaded area).
Figure 9A:
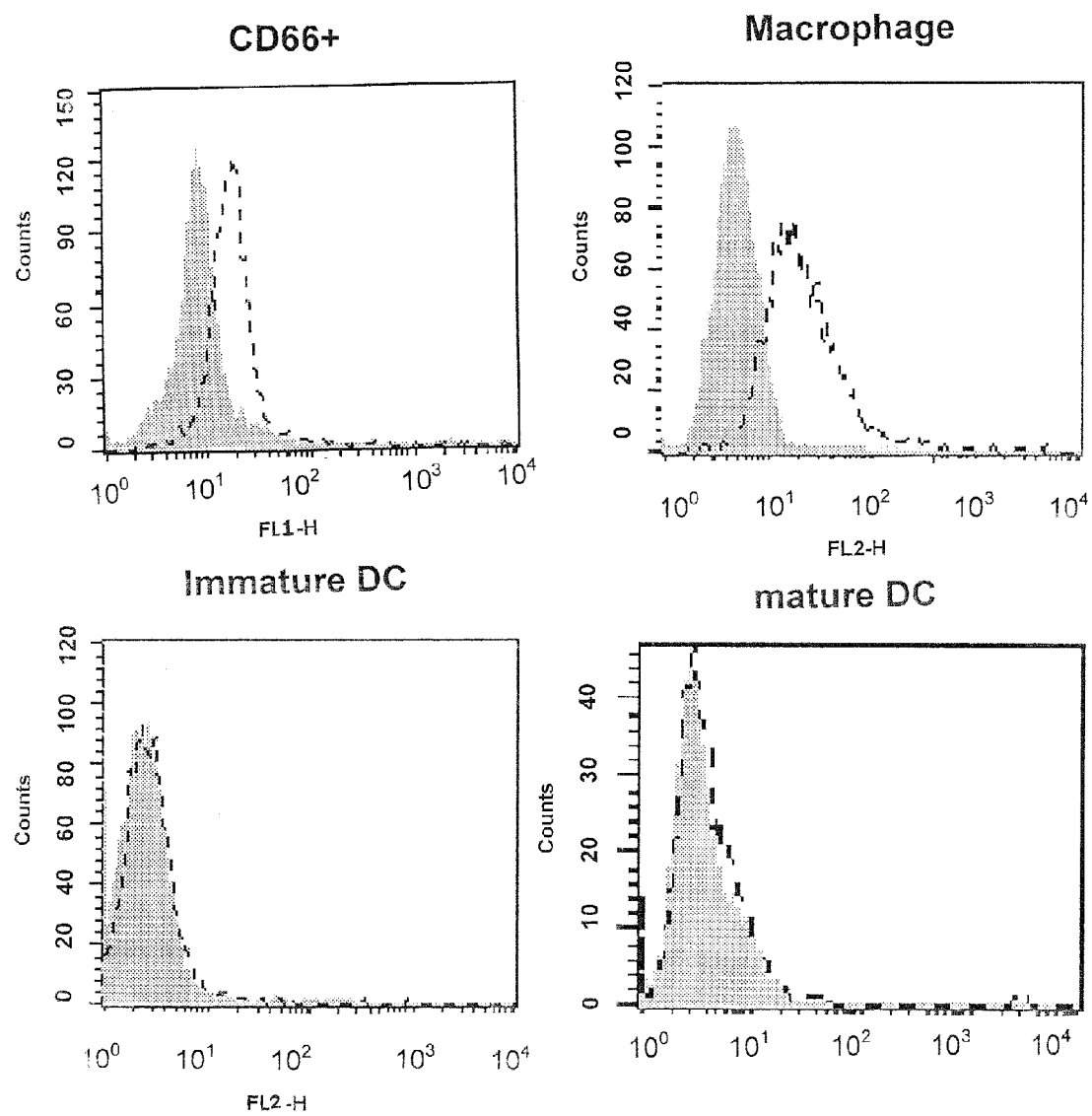
Figure 9B:
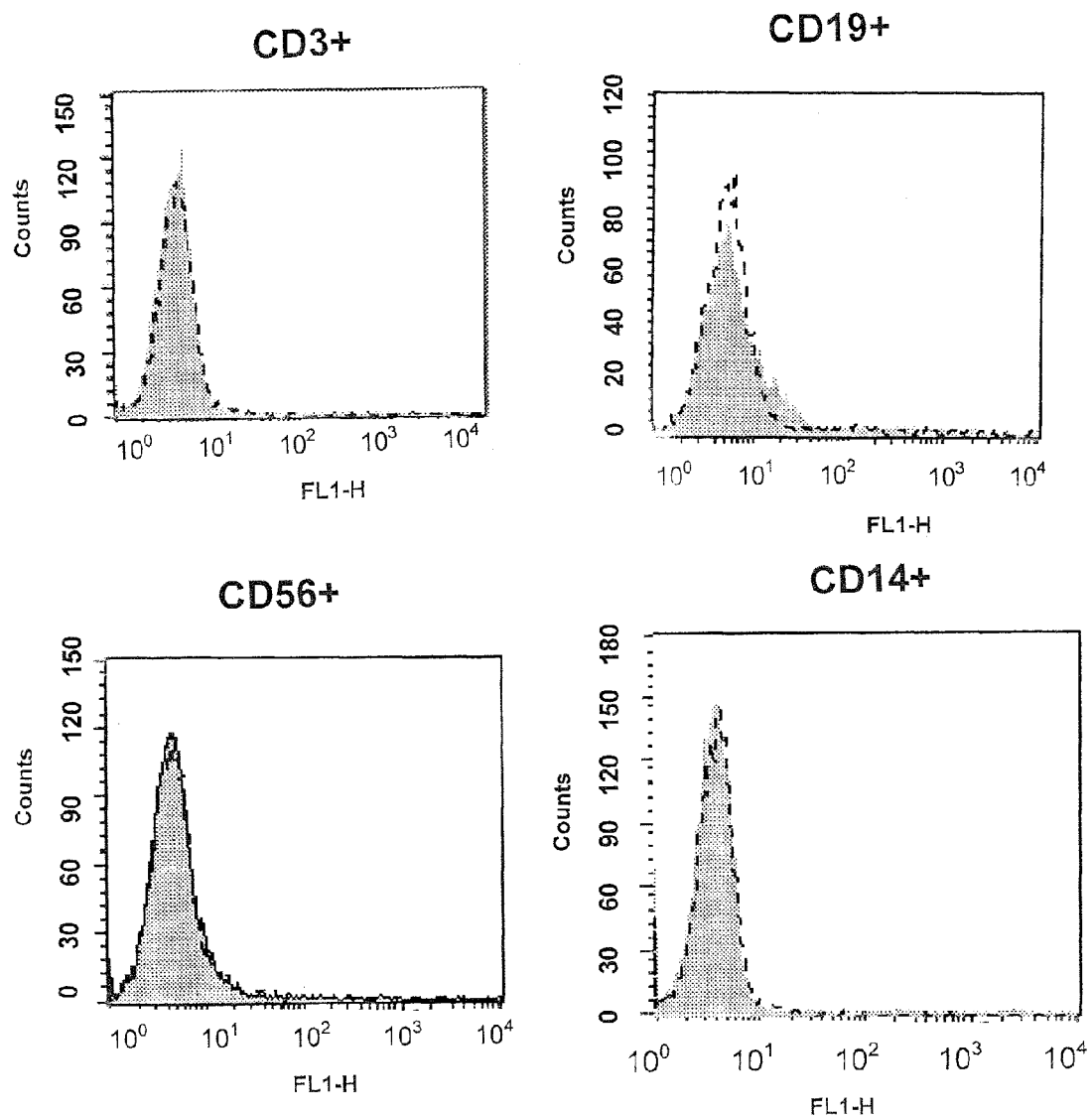
FIG. 9B shows the expression of DC-SIGN in various immune cell types by flow cytometry using an anti-DC-SIGN antibody. Expression of DC-SIGN is indicated where the DC-SIGN profile (dotted line trace) does not match the antibody isotype control (shaded area).
Figure 9B:
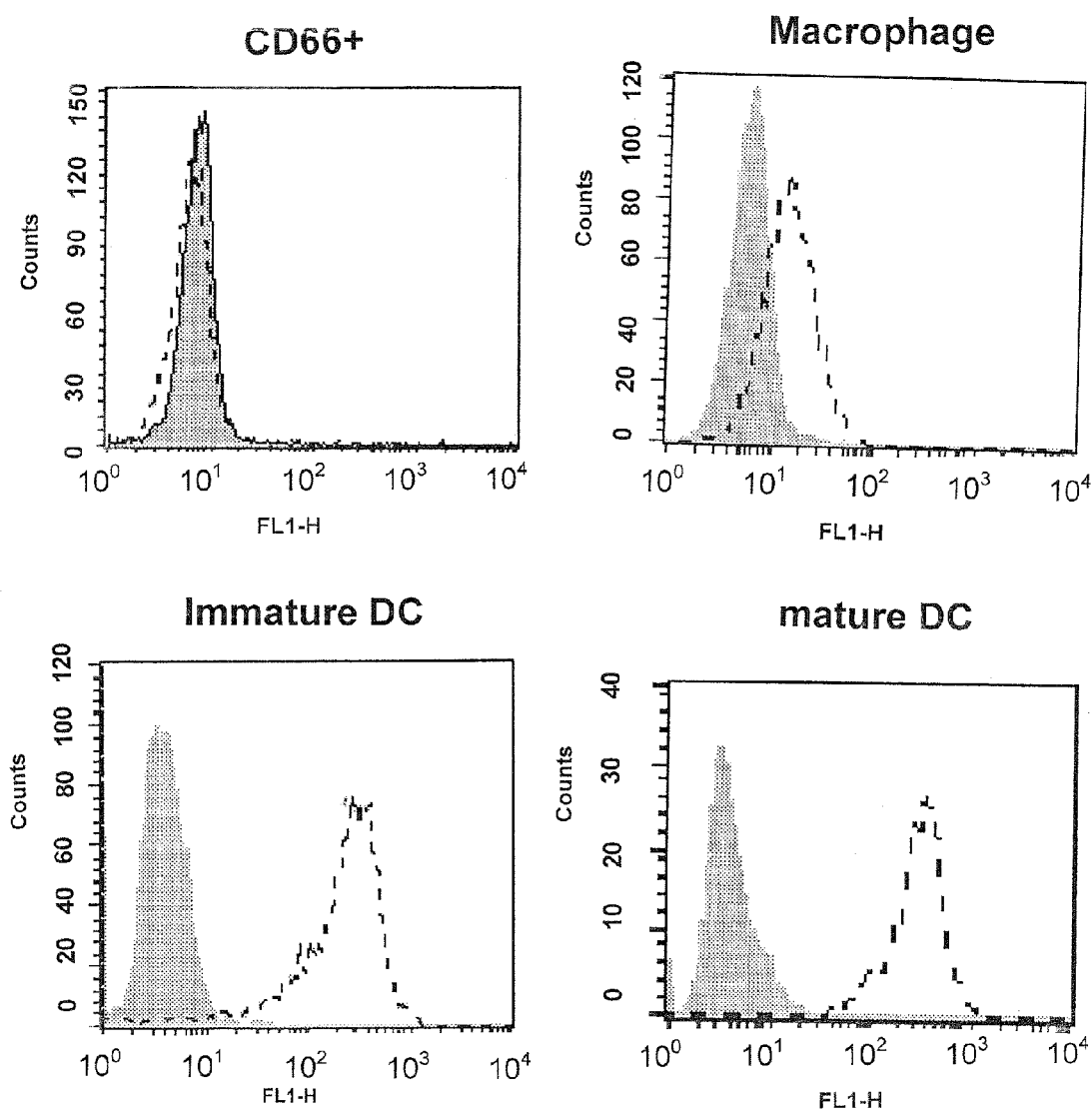

Flow cytometry was performed on the above-mentioned cell types using FITC-conjugated anti-DVLR1 monoclonal antibodies (R&D Systems, Minneapolis, Minn.), or FITC-conjugated anti-DC-SIGN monoclonal antibodies (ED PharMingen), in conjunction with Phycoerythrin (PE)-conjugated anti-CD3, CD19, CD56, CD14, and CD66 antibodies for double staining (BD PharMingen). Matched isotype controls (IgG2b for DVLRI mAb, IgG1 for DC-SIGN; Sigma) were also performed in this surface staining to provide background information. Fluorescence was analyzed by FACS-Calibur flow cytometry (Becton Dickinson) with CellQuest software (Becton Dickinson). CD marker positive cells were gated to determine the expression of DVLR1 or DC-SIGN. The results are shown in FIG. 9A (DVLR1) and FIG. 9B (DC-SIGN) (shaded area represents isotype control). The results indicate that DC-SIGN is mainly expressed on immature dendritic cells, and is weakly expressed on macrophages. The results also indicate that DVLR1 was detected on the surface of CD14+ derived macrophages (MΦ), CD66+ PMNs and CD14+ freshly isolated PBMCs, but not on CD14+ derived immature and mature dendritic cells. This is in accord with previous observations that DVLR1/MDL-1 mRNA is expressed in human monocytes and macrophages, but not in dendritic cells (Bakker et al., Proc. Natl. Acad Sci USA, 1999, 96(17):9792-9796).

The results presented in this example show that the receptor.Fc fusion protein-based methods disclosed herein can be used to determine the identity of the innate immunity receptors that bind to a specific pathogen, such as Dengue virus. This in turn allows one to identify the cell types that interact with the pathogen, and furthermore provides a new target for treatment or prevention of infection by the pathogen. For example, the results disclosed herein suggest that agents that prevent DV from binding to DVLR1 can be used for prophylactic and/or therapeutic purposes. For example, monoclonal antibodies against DVLR1 can be generated by one skilled in the art that prevent the binding of DV to DVLR1. Moreover, since DV is a member of the family Flaviviridae, this result suggests that DVLR1 may interact with other viruses within the same family, for example, viruses within the genus *Flavivirus* (such as West Nile Virus, Japanese encephamyelitis virus (JEV), yellow fever virus, tick-borne encephamyelitis virus) and viruses within the genus *Hepacivirus* (such as Hepatitis C virus). Accordingly, DVLR1 may serve as a therapeutic or prophylactic target for these viruses also. In addition, since DVLR1 is a pattern recognition receptor, DVLR1 may serve as a therapeutic or prophylactic target for other enveloped viruses, including but not limited to influenza virus.

Example 12

Dengue Virus Induced DAP12 Phosphorylaytion is Mediated Via DVLR1

DVLR1/MDL-1 is a type II transmembrane protein comprising 187 aa in length, and it includes a charged residue in the transmembrane region that enables it to pair with DAP12 (DNAX activating protein of 12 kDa) (Bakker et al., Proc. Natl. Acad Sci USA, 1999, 96(17):9792-9796). DAP12 is a disulfide-linked, homodimeric transmembrane protein with a minimal extracellular domain, a charged aspartic acid in the transmembrane domain and an ITAM (immunoreceptor tyrosine-based activation motif) in its cytoplasmic tail. Because DV binds to DVLR1 on CD14+ macrophages, and because DAP12 has an ITAM, it was of interest to determine whether DV can induce DAP12 phosphorylation in CD14+ macrophages. Accordingly, CD14+ macrophages were infected with DV using the a slight modification of the method disclosed in Chen et al, J. Virol. 2002, 76(19):9877-9887. Briefly, terminal differentiated macrophages were washed once with incomplete RPMI medium to remove fetal calf serum in culture medium. The cells were then infected with DV at different multiplicities of infection (MOI). The virus was incubated with the cells in serum-free RPMI at 37° C. for 2.5 h to permit viral adsorption. The culture plates were gently agitated every 30 min for optimal virus-cell contact. Thereafter, the unabsorbed viruses were removed by washing the cell monolayers twice with serum-free RPMI and then once with incubation, the cell-free supernatants were harvested separately and stored in aliquots at −80° C. until assayed for infectious-virus production and cytokine secretion (see Example 13). Infectious virus titers were determined by a plaque forming assay on BHK-21 cells. Plaques were counted by visual inspection at 7 days after crystal violet overlay to determine the number of plaque-forming units (PFU) per mL of supernant (Lin et al., J. Virol., 1998, 72(12): 9729-9737). To detect intracellular DV antigens, infected cells were fixed with 1% paraformaldehyde and permeabilized with 0.1% saponin, followed by staining with NS3 mAb (Lin et al., J. Virol., 1998, 72(12):9729-9737) or matched isotype control (IgG1; Sigma). After incubation for 1 h, PE-conjugated goat F(ab)' anti-mouse IgG secondary was added for fluorescence detection and fluorescence was analyzed by FACSCalibur flow cytometry with CellQuest software.

Figure 10A:
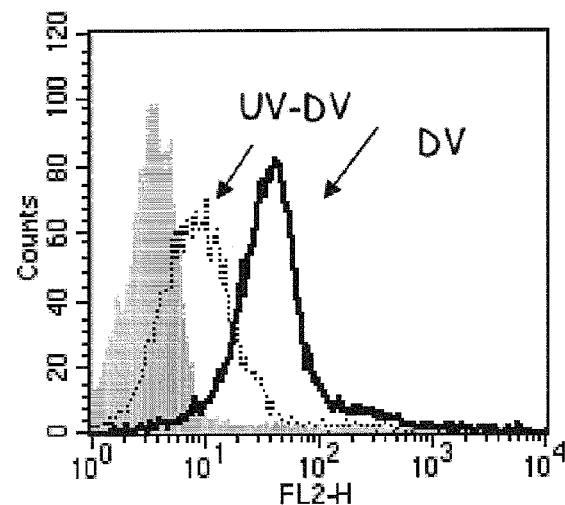
FIG. 10A shows flow cytometry analysis of the expression of NS3 protein using an anti-NS3 antibody in CD14+ macrophages contacted with live or UV irradiated (UV-DV) Dengue Virus, in comparison to a matched antibody isotype control (shaded area).
Figure 10B:
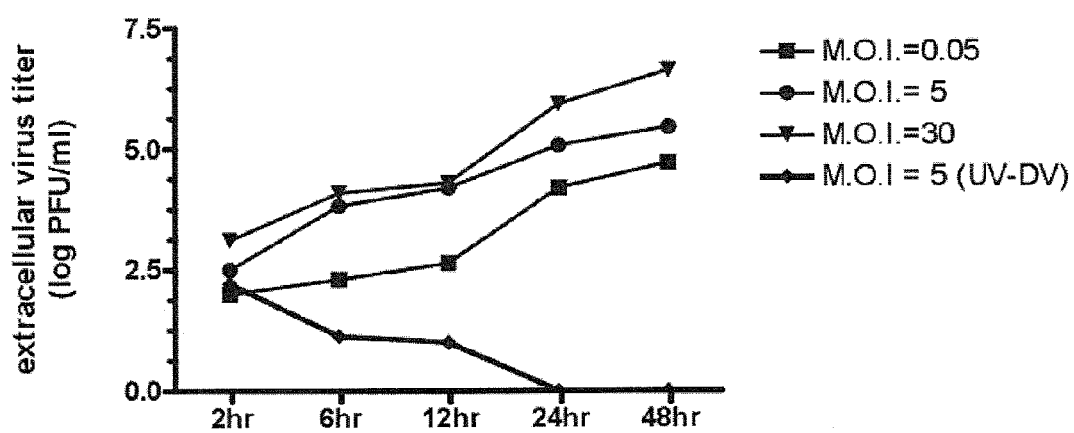
FIG. 10B shows graphically extracellular Dengue virus titers over time for CD 14+ macrophages infected with Dengue Virus at different multiplicities of infection (MOI) or with UV irradiated Dengue Virus.

The results are shown in FIG. 10A-D. At 48 h after infection at MOI=5, DV non-structural protein 3 (NS3) was detected by flow cytometry in the cytosol of macrophages (FIG. 10A; gray histogram is antibody isotype control). The extracellular virus titer was measured at various times following infection, and revealed that virus particles were released to culture supernatant when macrophages were infected with live DV, but not with UV-irradiated DV (UV-DV; 254 nm irradiation for 15 minutes on ice at 5 to 10 cm distance) (FIG. 10B).

DAP12 phosphorylation was studied 2 hours after infection at varying MOIs (MOI=0.05-30, 2 h after infection), and also at a fixed MOI (MOI=5) over a time course (2-48 h after infection). Specifically, for detection of phospho-DAP12, macrophages were stimulated with DV for the appropriate amount of time at the appropriate MOI and then lysed in lysis buffer (50 mM Tris-HCl [pH7.5], 150 mM NaCl, 1% Triton X-100, 0.1% SDS, 5 mM EDTA, 10 mM NaF, 1 mM sodium orthovanadate, and proteinase inhibitor cocktail tablet [Roche]). Equal amount of total cell extracts were immunoprecipitated with DAP12 rabbit polyclonal antibody (Santa Cruz Biotechnology Inc, CA) and protein A sepharose (Amersham Biosciences AB) for 4 h at 4° C. After incubation, the immunocomplex was washed three times and separated by SDS-PAGE, followed by transferring onto nitrocellulose membrane and probed with anti-phosphotyrosine antibody (4G10; Upstate Biotechnology, Inc). Immunoblots were developed using HRP-conjugated second antibody and enhanced chemiluminescence (Amersham). For reprobing, the membrane was stripped with a strong re-probe kit (Chemicon) and blotted with DAP12 antibody.

Figure 10C:
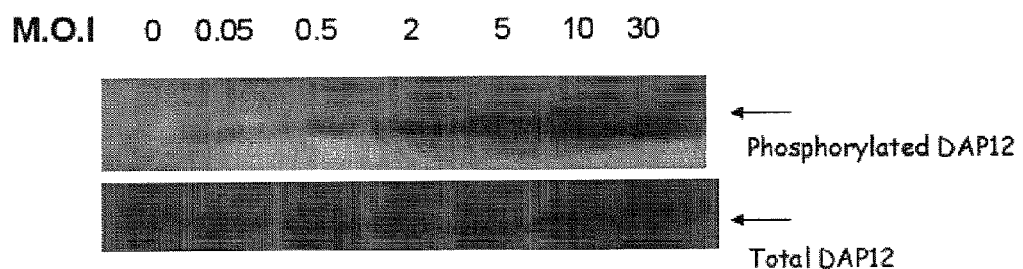
FIG. 10C shows an immunoblot illustrating total DAP12 and phosphorylated DAP12 in CD14+ macrophages infected with Dengue virus at different MOIs.
Figure 10D:
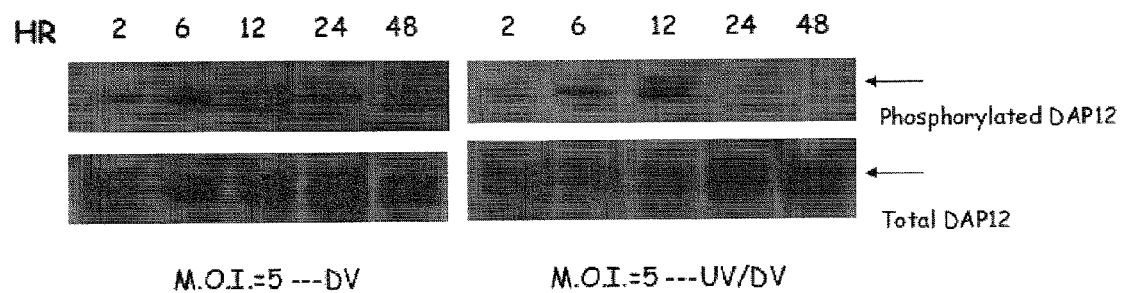
FIG. 10D shows an immunoblot illustrating total DAP12 and phosphorylated DAP12 in CD14+ macrophages infected with Dengue virus at different times following infection with live Dengue virus or UV irradiated Dengue virus at MOI=5.

The results obtained at various MOIs are shown in FIG. 10C, and the time course experiment results are shown in FIG. 10D. The results show that at 2 h after DV infection, the intensity of DAP12 phosphorylation increased as the MOI was raised from MOI=0.05, reaching a peak when MOI=5 (FIG. 10C). DAP12 phosphorylation was detected at 2 h after DV infection, peaked at 12 h, and lasted for at least 48 h (FIG. 10D). Even though UV-DV could not replicate in CD14+ macrophages and had no activity in a plaque assay (FIG. 10B), DAP12 was also phosphorylated at 2 h and phosphorylated DAP12 remained detectable at 12 h, even though the intensity is much weaker than that induced by live DV (FIG. 10D; UV-DV). This suggests that DV-induced DAP12 phosphorylation has two phases: phase I (in the first 6 h) is replication-independent, while phase II (after 12 h) is replication-dependent.

To confirm that DAP12 phosphorylation was via DVLR1, RNA interference (RNAi) with short hairpin RNA (shRNA) was used to inhibit the expression of DVLR1 in CD14+ macrophages and DAP12 phosphorylation was assayed as above. Specifically, the coding region of human DVLR1 was targeted with the following DVLR1 siRNA:

5'-TTGTTGGAATGACCTTAT-3'    SEQ ID NO: 39

This stretch was adapted with loop sequence (TTCAA-GAGA) from Brummelkamp et al., Science, 2002, 296(5567): 550-553, to create an shRNA. The polymerase III terminator stretch used here was TTTTTT. The shRNA was cloned into the pLL3.7 gene silencing vector (Rubinson et al., Nat. Genet., 2003, 33(3):401-406) which contained loxp sites, a CMV (cytomegalovirus) promoter driving expression of enhanced green fluorescent protein (EGFP), and a U6 promoter with downstream restriction sites (HpaI and XhoI). A DC-SIGN shRNA construct was also constructed by subcloning the shRNA contained in the construct pSUPER-siDC-SIGN (Tassaneetrithep et al., supra) into pLL3.7 vector digested with HpaI/XhoI. The constructs were electroporated into macrophages using the Amaxa kit (Gaithersburg, Md.) according manufacturer's specifications. Briefly, macrophages ($6 \times 10^6$) were harvested as described above and resuspended in 100 μL of nucleofactor solution. After the addition of siRNA (5 μg) or vector control, cells were electroporated using Amaxa program Y-001 and allowed to recover for 16 h. The efficiency of DVLR1 and DC-SIGN silencing was analyzed 24 hrs after transfection by immunoblotting using anti-DVLR1 and DC-SIGN monoclonal antibodies (R&D Systems), respectively.

Figure 11:
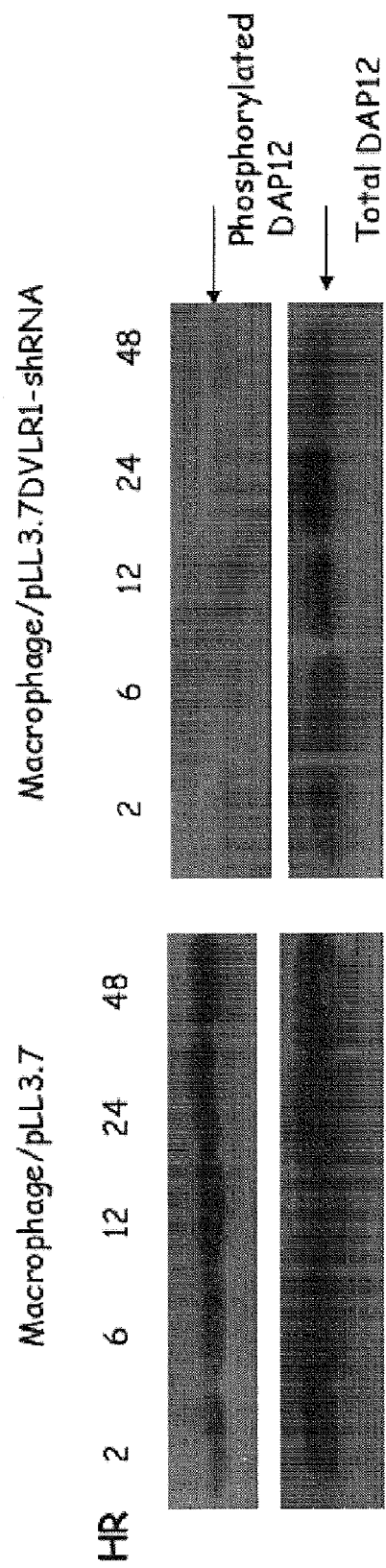
FIG. 11 shows an immunoblot illustrating total DAP12 and phosphorylated DAP12 in CD14+ macrophages electroporated with pLL3.7 vector (control) or with DVLR1-shRNA prior to infection with Dengue virus.

The results are shown in FIG. 11. CD14+ macrophages electroporated with the control vector pLL3.7 or with DC-SIGN-shRNA did not show a reduction in DAP12 phosphorylation after DV infection. By contrast, DAP12 phosphorylation decreased dramatically in CD14+ macrophages electroporated with DVLR1-shRNA prior to DV infection. Therefore, it was concluded that DV-induced DAP12 phosphorylation occurs via DVLR1.

Example 13

Figure 12A:
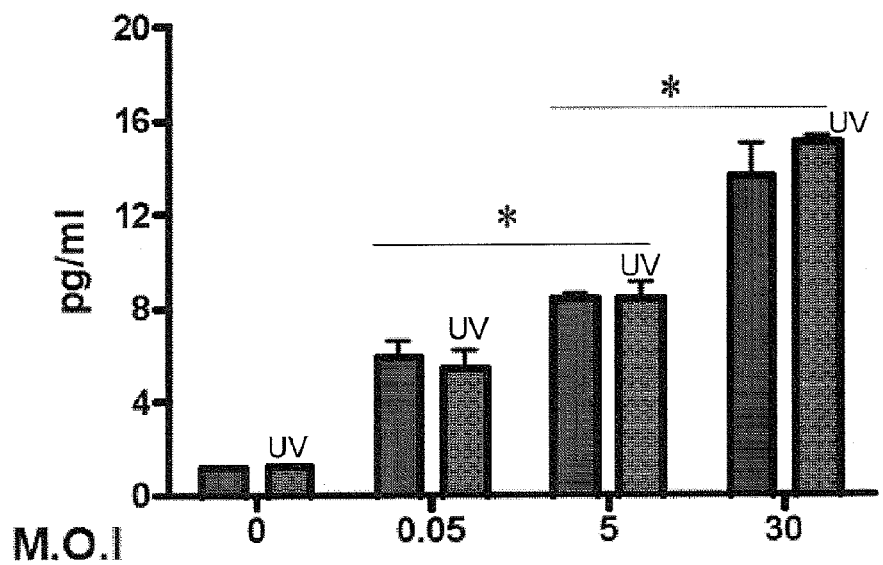
FIG. 12A shows the secretion of TNF-α at 6 hours after infection of CD14+ macrophages with live or UV-irradiated Dengue Virus at the specified MOIs.
Figure 12B:
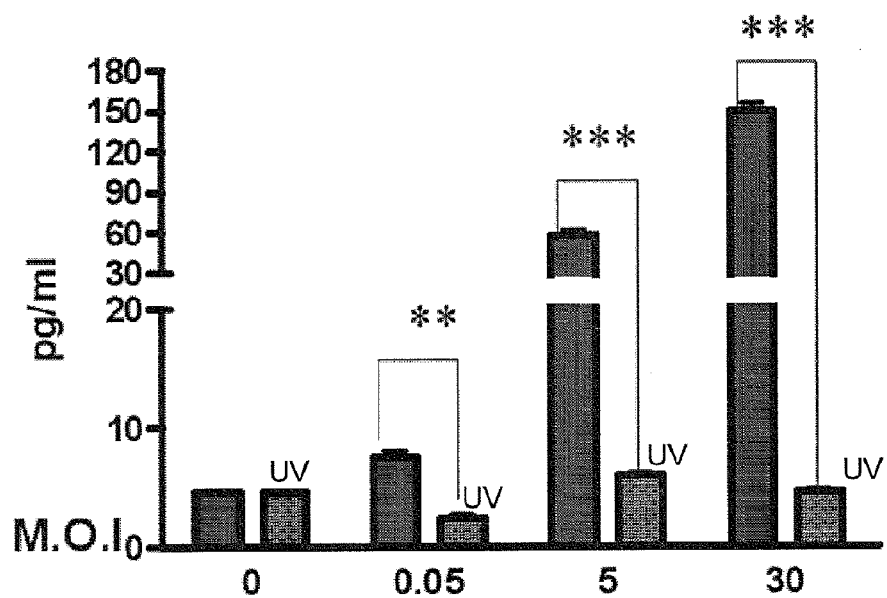
FIG. 12B shows the secretion of TNF-α at 12 hours after infection of CD14+ macrophages with live or V-irradiated Dengue Virus at the specified MOIs.
Figure 12C:
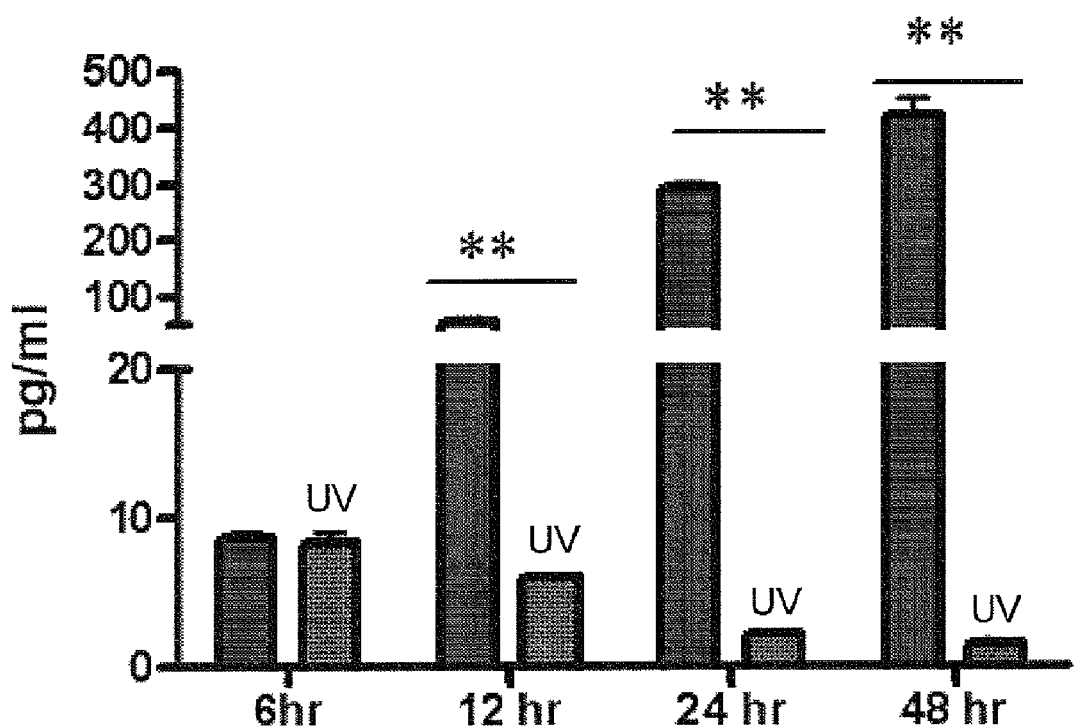
FIG. 12C shows time course measurements of the secretion of TNF-α following infection of CD14+ macrophages.

DVLR1 is Involved in DV-Mediated TNF-α Release, but not Entry to CD14+ Macrophages Upon DV infection, CD14+ macrophages secrete pro-inflammatory cytokines and chemokines, including tumor necrosis factor alpha (TNF-α), alpha-interferon (IFN-α), MIP-1α, and IL-8 (Chen et al, supra). The levels of TNF-α in culture supernatant were measured in DV-infected CD14+ macrophages using a commercial ELISA kit. Measurements were made at different MOIs and at different times post-infection for both live DV and UV-DV. The results are shown in FIG. 12A-C (error bars represent the standard error from the mean of triplicates, and asterisks indicate statistically different levels of cytokine production; *=p<0.05; =p<0.01; *=p<0.001). The results show that at 6 hours post infection, both live DV and DV-UV had similar effects on TNF-α secretion at MOIs ranging from 0.05-30 (FIG. 12A). At 12 hours post infection, TNF-α secretion increased in a dose dependent (increasing MOI) manner only for live DV. For UV-DV infected cells at 12 hours post infection, TNF-α levels remained the same at all MOIs (FIG. 12B). FIG. 12C shows a time course measurement of TNF. The results show that when infected with live DV at MOI=5, TNF-α secretion increased rapidly from 6 h (8 pg/ml) to 12 h (85 pg/ml), and peaked at 48 h (350 pg/ml). When incubated with UV-DV, however, TNF-α secretion decreased from 8 pg/ml (at 6 h) to 5 pg/ml (at 12 h). This suggests that the initial response (at 6 h) is independent of virus replication, while the later phase of TNF-α secretion (after 12 h) correlates with DV replication.

Figure 13A:
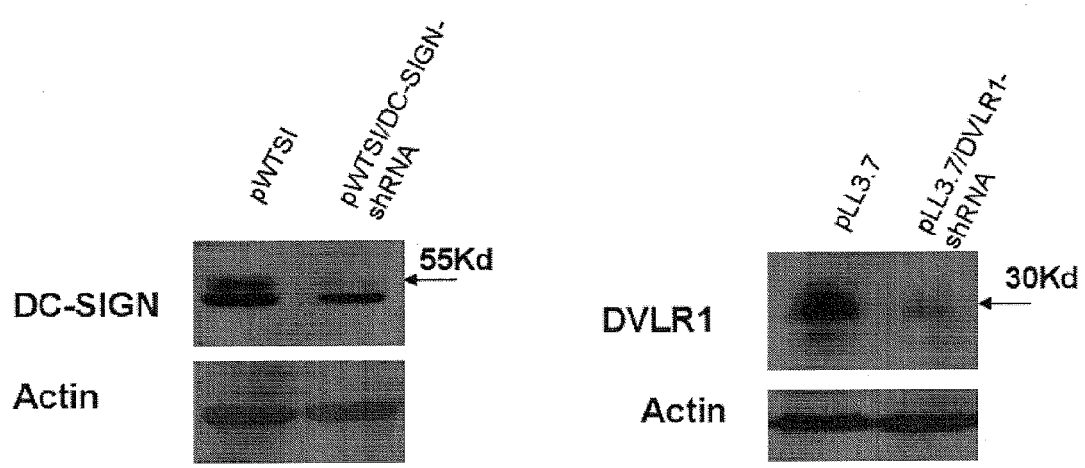
FIG. 13A shows the expression of DC-SIGN and DVLR1 by Western blot in CD14+ macrophages transfected with DC-SIGN-shRNA or DVLR1-shRNA, or with vector controls (pWTSI and pLL3.7).
Figure 13B:
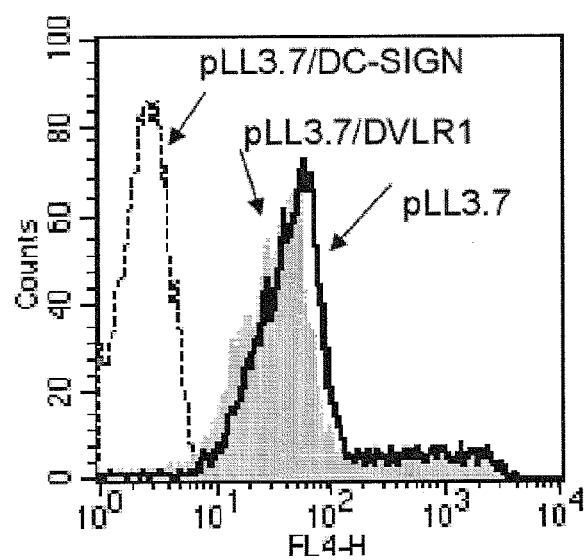
FIG. 13B shows flow cytometry analysis of NS3 expression (using anti-NS3 antibody) in CD14+ macrophages electroporated with DC-SIGN-shRNA, DVLR1-shRNA, or pLL3.7 vector control prior to infection with Dengue virus. The shaded area is an isotype control for the NS3 antibody.
Figure 13C:
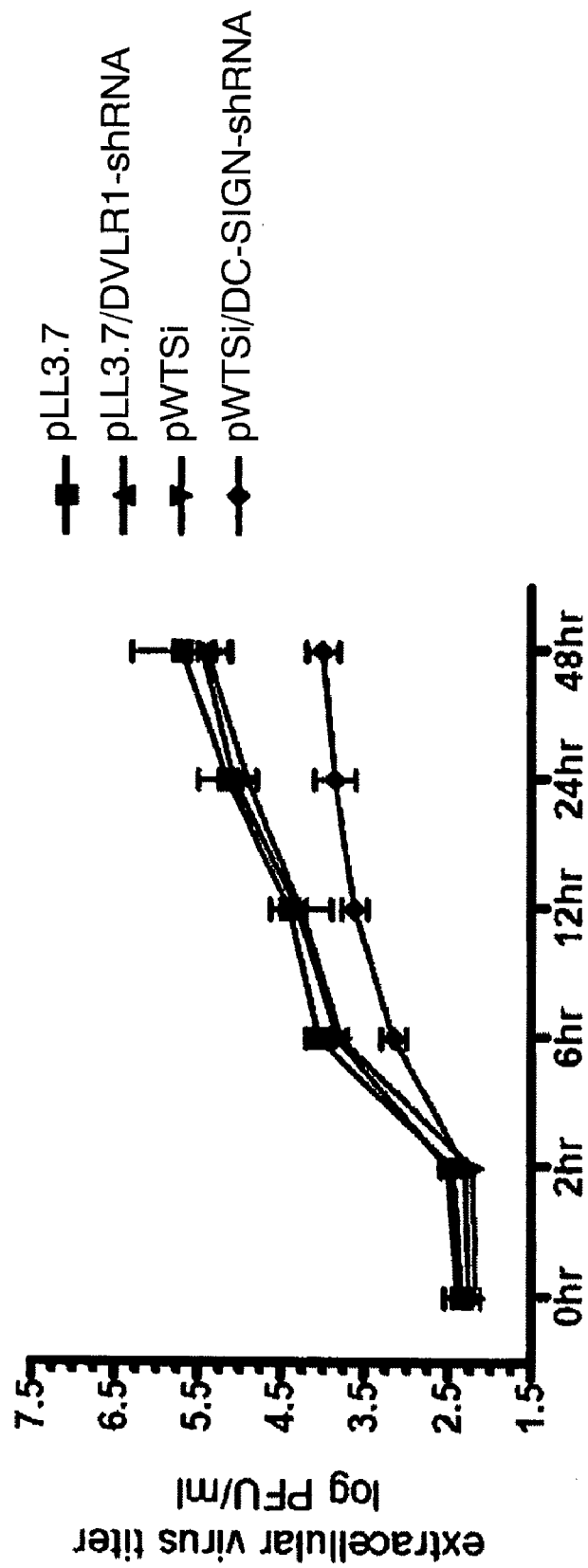
FIG. 13C illustrates a time course analysis of virus titer in the supernatant of CD14+ macrophages electroporated with DC-SIGN-shRNA, DVLR1-shRNA, or vector controls, prior to infection with Dengue virus at t=0.

DC-SIGN has previously been shown to interact with DV in order to mediate virus entry into dendritic cells. Using the RNAi methodology and reagents of the prior examples, the effect of DC-SIGN-shRNA and DVLR1-shRNA on NS3 expression in DV-infected CD14+ macrophages was investigated. FIG. 13A shows that DC-SIGN-shRNA and DVLR1-shRNA can knock down their respective proteins (pWTSI and pLL3.7 are no insert controls). FIG. 13B depicts the results of flow cytometry analysis and illustrates that only DC-SIGN-shRNA could attenuate DV NS3 expression in CD14+ macrophages. This result was confirmed using immunofluorescence confocal microscopy using anti-DS3 antibodies. FIG. 13C illustrates real time PCR analysis of virus titer in the supernatant of cells electroporated with the shRNA constructs. The results indicate that only DC-SIGN-shRNA is capable of reducing virus titer in the supernatant of DV-infected cells.

Example 14

Figure 14A:
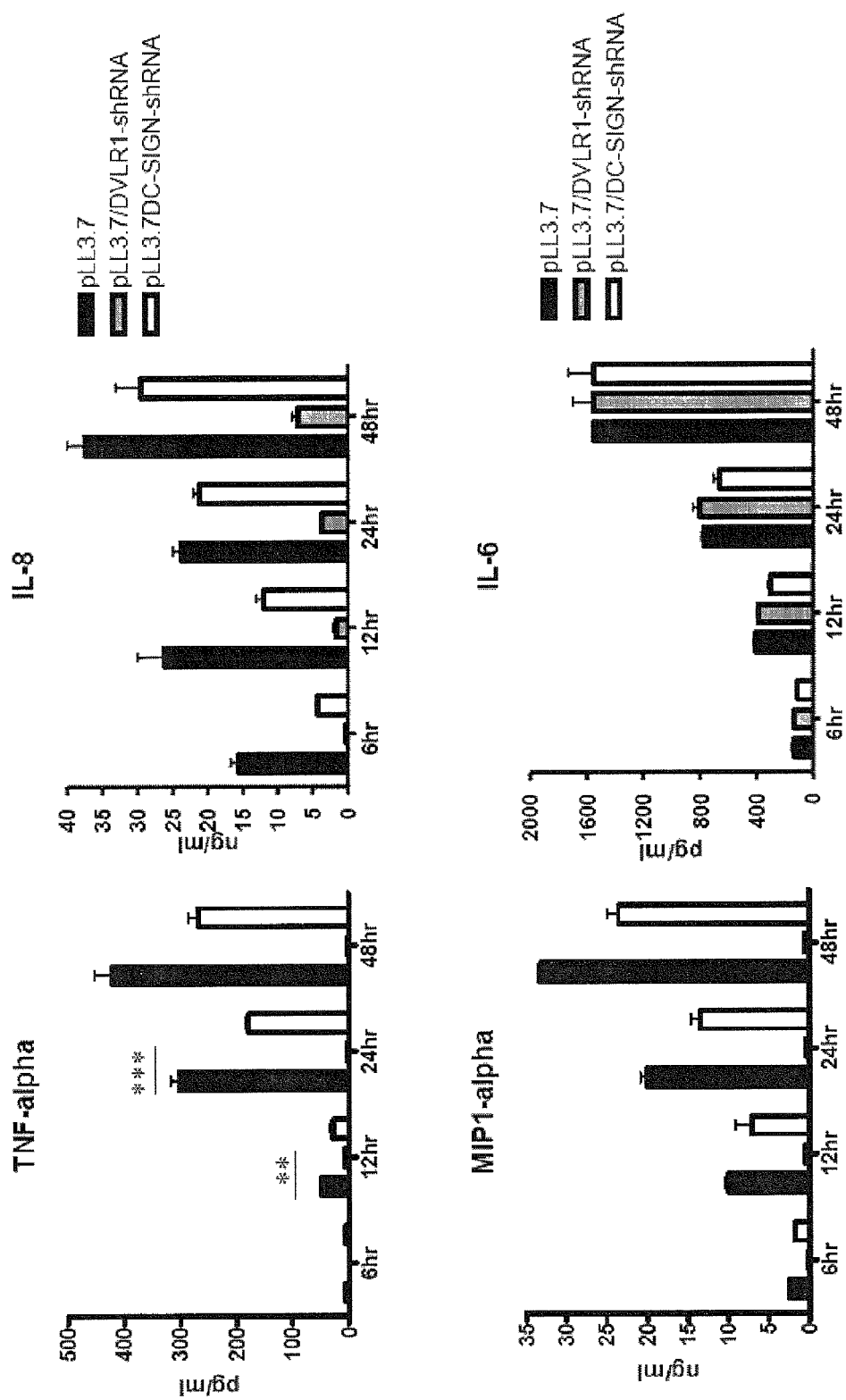
FIG. 14A shows a time course analysis of the secretion of various cytokines by CD14+ macrophages that were electroporated with DC-SIGN-shRNA, DVLR1-shRNA, or vector controls prior to infection with Dengue virus at t=0.
Figure 14B:
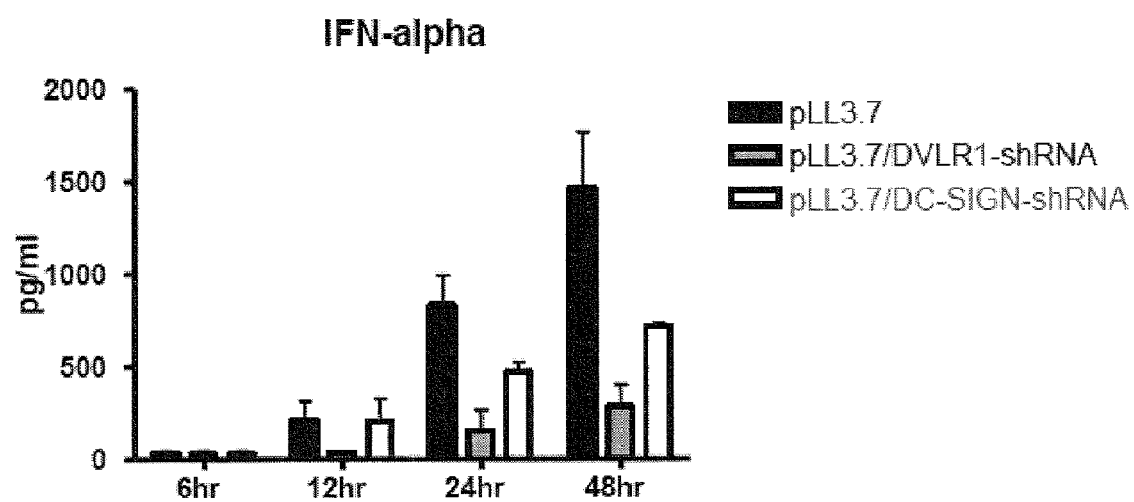
FIG. 14B shows a time course analysis for the cytokine IFN-α under the same conditions.

DVLR1 is Involved in DV-Induced Proinflammatory Cytokine Release from CD14+ Macrophages The cytokine release profile for CD14+ macrophages infected with DV (MOI=5) was evaluated using ELISA after knock down of DVLR1 and DC-SIGN according to the methods of the preceding examples (2.5 h transfection). In the first 12 h, DC-SIGN-shRNA did not affect the secretion of TNF-α, MIP-1α, IFN-α, IL-6, or IL-8. See FIG. 14A-B (error bars represent the standard error from the mean of triplicates, and asterisks indicate statistically significant differences compared to control experiments; *=p<0.05; =p<0.01; *=p<0.001). After 48 h, DC-SIGN-shRNA had a mild inhibitory effect (less than 20%) on TNF-α, MIP-1α, IFN-α, and IL-6 secretion; IL-8 secretion was not affected. Since DC-SIGN is involved in virus entry and replication, this observation suggests that initial cytokine secretion (first 12 h) is independent of DV replication. In contrast, knock down of DVLR1 dramatically suppressed (p<0.005) the secretion of TNF-α, MIP-1α, IFN-α, IL-8, but not of IL-6. This suggests that DVLR1 is responsible for DV-induced cytokine release from CD14+ macrophages. Accordingly, therapeutic agents that prevent the binding of DV to DVLR1 will be useful for preventing the deleterious effects of DV-induced cytokine release in humans. For example, monoclonal antibodies that prevent DVLR1 interaction with DV will be useful for preventing or treating DV-induced Dengue shock syndrome (DSS) or Dengue haemorrhagic fever (DHF).

Example 15

Antagonistic Anti-DVLR1 Monoclonal Antibodies (mABS) Abolish Inflammatory Cytokine Release by DV Serotypes 1,2,3, and 4

Figure 15:
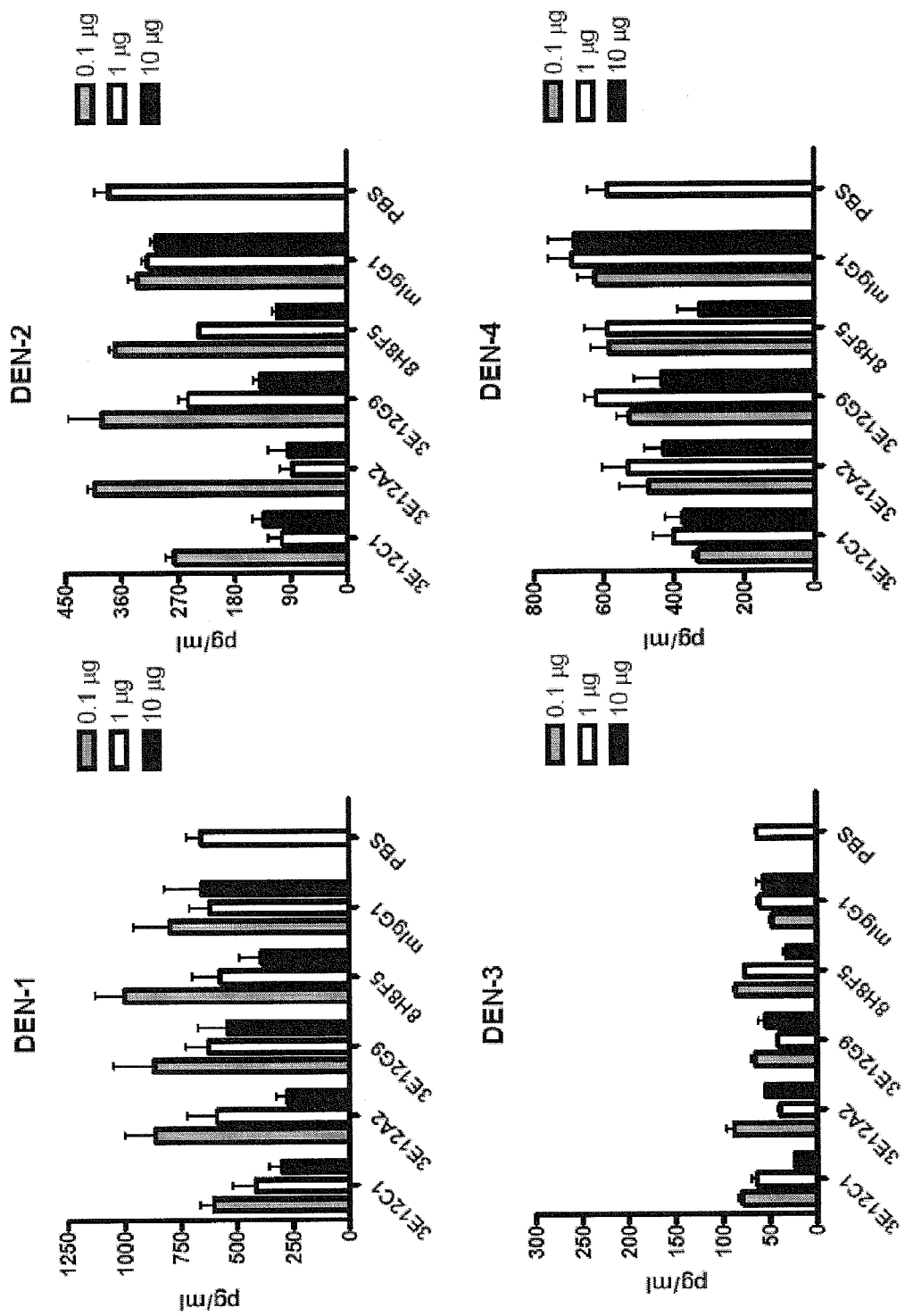
FIG. 15 shows ELISA measurements of TNF-α secreted into culture supernatants by CD14+ macrophages infected with Dengue virus and treated with the specified monoclonal antibody against DVLR1 at the specified concentrations.

Monoclonal antibodies against DVLR1 were generated using standard techniques. Briefly, mice were immunized with DVLR-1.Fc fusion protein, and hybridomas were formed by fusing splenocytes from the mice with P3/NSI/1-Ag4-1 [NS-1] myeloma cells (ATCC TIB-18). Among the mAbs generated, clone 9B12, the subclones of 3E12 (clones 3E12A2, 3E12C1, 3E12G9), and clone 8H8F5 suppressed TNF-α release from macrophages after infection with DEN1 (strain 766733A), DEN2 (strain PL046), DEN3 (strain H-87), and DEN4 (strain 866146A) in a dose-dependent manner. See FIG. 15 which shows ELISA measurements of TNF-α secreted into culture supernatants by CD14+ macrophages infected with DV. In accordance with standard nomenclature, each antibody is referred to via the clone number of the hybridoma that secretes it. Hence, the disclosure also provides the hybridomas that secrete the abovementioned monoclonal antibodies.

The results demonstrate that anti-DVLR1 antibodies will serve as useful therapeutic agents for preventing proinflammatory cytokine release from DV-infected CD14+ macrophages in humans. In particular, but not exclusively, the monoclonal antibodies of this Example, or fragments thereof, or antibodies (or fragments thereof) that bind to the same epitopes as the antibodies of this Example, may be formulated as pharmaceutical compositions and then administered for the treatment or prophylaxis of DV infection in humans, according to the methods provided herein.

Deposit of Materials

The foregoing written specification is considered to be sufficient to enable one skilled in the art to practice the invention. The present invention is not to be limited in scope by the hybridomas deposited, since the deposited embodiments are intended to illustrate only certain aspects of the invention and any antibodies that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that they represent. Indeed, various modifications of the invention in addition to those shown and described herein will become apparent to those skilled in the art from the foregoing description and fall within the scope of the appended claims.

What is claimed is:

1. A method of inhibiting Dengue virus-mediated secretion of proinflammatory cytokines from a macrophage, comprising contacting the macrophage with an antibody that specifically binds to the extracellular domain of Dengue Virus Lectin Receptor 1 (DVLR1) and prevents binding of Dengue virus to DVLR1.

2. The method of claim 1, wherein the antibody is a monoclonal antibody.

3. The method of claim 1, wherein the antibody is a humanized antibody.

4. The method of claim 1, wherein the antibody is a receptor binding antibody fragment.

* * * * *